United States Patent
Humphrey

(10) Patent No.: US 9,956,083 B2
(45) Date of Patent: May 1, 2018

(54) INSTRUMENTS AND TECHNIQUES FOR ORIENTING PROSTHESIS COMPONENTS FOR JOINT PROSTHESES

(71) Applicant: SHOULDER OPTIONS, INC., Waxhaw, NC (US)

(72) Inventor: C. Scott Humphrey, Eagle, ID (US)

(73) Assignee: Deltoid, LLC, Eagle, ID (US)

(*) Notice: Subject to any disclaimer, the term of this patent is extended or adjusted under 35 U.S.C. 154(b) by 0 days. days.

(21) Appl. No.: 14/586,677

(22) Filed: Dec. 30, 2014

(65) Prior Publication Data

US 2015/0250601 A1 Sep. 10, 2015

Related U.S. Application Data

(60) Provisional application No. 61/921,593, filed on Dec. 30, 2013, provisional application No. 61/928,399, filed on Jan. 16, 2014.

(51) Int. Cl.
*A61F 2/40* (2006.01)
*A61F 2/46* (2006.01)
(Continued)

(52) U.S. Cl.
CPC ........ *A61F 2/4014* (2013.01); *A61B 17/1637* (2013.01); *A61B 17/1684* (2013.01);
(Continued)

(58) Field of Classification Search
CPC .. A61F 2/40; A61F 2/4003; A61F 2002/4011; A61F 2/4014; A61F 2002/4037
See application file for complete search history.

(56) References Cited

U.S. PATENT DOCUMENTS 4,261,062 A 4/1981 Amstutz et al.
4,865,605 A 9/1989 Dines et al.
(Continued)

FOREIGN PATENT DOCUMENTS

EP 2473139 A2 7/2012
EP 2604226 A1 6/2013
(Continued)

OTHER PUBLICATIONS

"Optimizing glenosphere position and fixation in reverse shoulder athroplasty, Part Two: The three-column concept", C. Scott Humphrey, M.D., James D. Kelly, II, M.D. and Tom R. Norris, M.D., Boise, ID, and San Francisco, CA Copyright © 2008 by Journal of Shoulder and Elbow Surgery Board of Trustees: doi: 10.1016/j.jse.2008.05.038 http://www.ncbi.nlm.nih.gov/pubmed/18541444.
(Continued)

*Primary Examiner* — Christopher D Prone
*Assistant Examiner* — Suba Ganesan
(74) *Attorney, Agent, or Firm* — McNees Wallace & Nurick LLC

(57) ABSTRACT

The present invention is directed to a modular assembly for an arthroplasty in a long bone and methods for achieving an anatomically accurate reconstruction. A modular arthroplasty assembly includes the components of: a convertible offset coupler bounded on a first side by an implant surface adapted to receive an implant component, and bounded on an opposite second side by a bone anchor engagement surface, prosthesis component and a bone anchor configured to be inserted in bone and adapted for engagement with the convertible offset coupler. Together, the components of the system, including the array of selectable engagement orientations of the components, enables adaptation to the existing anatomy of the patient and the ability to most closely achieve the native anatomy of the healthy shoulder joint so (Continued)

as to provide the patient with the most natural use of the joint. The system also provides a solution for reverse arthroplasty and conversion from anatomically correct to reverse that avoids a boney procedure on revision and minimizes humeral distalization.

18 Claims, 68 Drawing Sheets

(51) Int. Cl.
   *A61B 17/16*   (2006.01)
   *A61F 2/30*    (2006.01)
   *A61B 17/17*   (2006.01)

(52) U.S. Cl.
   CPC .......... *A61F 2/4003* (2013.01); *A61F 2/4059* (2013.01); *A61F 2/4081* (2013.01); *A61F 2/4657* (2013.01); *A61B 17/1778* (2016.11); *A61F 2/4684* (2013.01); *A61F 2002/305* (2013.01); *A61F 2002/3054* (2013.01); *A61F 2002/30253* (2013.01); *A61F 2002/30332* (2013.01); *A61F 2002/30433* (2013.01); *A61F 2002/30607* (2013.01); *A61F 2002/30614* (2013.01); *A61F 2002/30878* (2013.01); *A61F 2002/4022* (2013.01); *A61F 2002/4029* (2013.01); *A61F 2002/4037* (2013.01); *A61F 2002/4044* (2013.01); *A61F 2002/4077* (2013.01); *A61F 2002/4085* (2013.01)

(56) References Cited

U.S. PATENT DOCUMENTS

| | | | |
|---|---|---|---|
| 4,919,670 A | 4/1990 | Dale et al. | |
| 5,370,703 A | 12/1994 | Willert et al. | |
| 5,489,309 A | 2/1996 | Lackey et al. | |
| 5,702,457 A | 12/1997 | Walch et al. | |
| 6,187,050 B1 | 2/2001 | Khalili et al. | |
| 6,197,062 B1 | 3/2001 | Fenlin | |
| 6,508,840 B1 | 1/2003 | Rockwood, Jr. et al. | |
| 6,514,287 B2 | 2/2003 | Ondrla et al. | |
| 6,537,321 B1 | 3/2003 | Horber | |
| 6,673,115 B2 | 1/2004 | Resch et al. | |
| 6,679,916 B1 | 1/2004 | Frankle et al. | |
| 6,699,289 B2 | 3/2004 | Iannotti et al. | |
| 6,719,799 B1 | 4/2004 | Kropf | |
| 6,783,549 B1 | 8/2004 | Stone et al. | |
| 6,790,234 B1 | 9/2004 | Frankle | |
| 6,942,699 B2 | 9/2005 | Stone et al. | |
| 7,044,973 B2 | 5/2006 | Rockwood et al. | |
| 7,175,663 B1 | 2/2007 | Stone | |
| 7,448,530 B1 | 11/2008 | Winikoff | |
| 7,462,197 B2 | 12/2008 | Tornier et al. | |
| 7,621,961 B2 | 11/2009 | Stone | |
| 7,648,530 B2 | 1/2010 | Habermeyer et al. | |
| 7,819,923 B2 | 10/2010 | Stone et al. | |
| 7,854,768 B2 | 12/2010 | Wiley et al. | |
| 7,879,275 B2 | 2/2011 | Smith et al. | |
| 7,922,769 B2 | 4/2011 | Deffenbaugh et al. | |
| 7,959,680 B2 | 6/2011 | Stone et al. | |
| 7,981,161 B2 | 7/2011 | Choi et al. | |
| 8,048,161 B2 | 11/2011 | Guederian et al. | |
| 8,062,376 B2 | 11/2011 | Shultz et al. | |
| 8,080,063 B2 | 12/2011 | Ferrand et al. | |
| 8,236,059 B2 | 8/2012 | Stone et al. | |
| 8,246,687 B2 | 8/2012 | Katrana et al. | |
| 8,287,600 B2 | 10/2012 | Angibaud | |
| 8,317,871 B2 | 11/2012 | Stone et al. | |
| 8,419,798 B2 | 4/2013 | Ondrla et al. | |
| 8,454,702 B2 | 6/2013 | Smits et al. | |
| 8,506,638 B2 | 8/2013 | Vanasse et al. | |
| 8,512,410 B2 | 8/2013 | Metcalfe et al. | |
| 8,529,629 B2 | 9/2013 | Angibaud et al. | |
| 8,545,511 B2 | 10/2013 | Splieth et al. | |
| 8,608,805 B2 | 12/2013 | Forrer et al. | |
| 8,663,335 B2 | 3/2014 | Katrana et al. | |
| 8,845,742 B2 | 9/2014 | Kusogullari et al. | |
| 8,920,508 B2 | 12/2014 | Iannotti et al. | |
| 2001/0041940 A1* | 11/2001 | Pearl ........................ A61F 2/40 623/19.14 |
| 2004/0059424 A1 | 3/2004 | Guederian et al. | |
| 2004/0225367 A1 | 11/2004 | Glien et al. | |
| 2005/0107882 A1 | 5/2005 | Stone et al. | |
| 2005/0288791 A1 | 12/2005 | Tornier et al. | |
| 2006/0009852 A1 | 1/2006 | Winslow et al. | |
| 2007/0142918 A1 | 6/2007 | Stone | |
| 2007/0198094 A1 | 8/2007 | Berelsman et al. | |
| 2007/0225818 A1 | 9/2007 | Reubelt et al. | |
| 2007/0225821 A1 | 9/2007 | Reubelt et al. | |
| 2008/0140211 A1* | 6/2008 | Doubler ............... A61F 2/4014 623/19.14 |
| 2009/0192621 A1 | 7/2009 | Winslow et al. | |
| 2010/0087927 A1 | 4/2010 | Roche et al. | |
| 2011/0035013 A1 | 2/2011 | Winslow et al. | |
| 2011/0053160 A1 | 3/2011 | Ali et al. | |
| 2011/0054624 A1 | 3/2011 | Iannotti | |
| 2012/0109321 A1 | 5/2012 | Stone et al. | |
| 2012/0130498 A1 | 5/2012 | Long | |
| 2012/0130499 A1 | 5/2012 | Long | |
| 2012/0179262 A1 | 7/2012 | Metcalfe et al. | |
| 2012/0179263 A1 | 7/2012 | Metcalfe et al. | |
| 2012/0209392 A1 | 8/2012 | Angibaud et al. | |
| 2012/0221111 A1 | 8/2012 | Burkhead, Jr. et al. | |
| 2012/0253467 A1 | 10/2012 | Frankle | |
| 2013/0090736 A1 | 4/2013 | Katrana et al. | |
| 2013/0150972 A1 | 6/2013 | Iannotti et al. | |
| 2013/0173007 A1 | 7/2013 | Duport | |
| 2013/0178943 A1 | 7/2013 | Duport | |
| 2013/0245775 A1 | 9/2013 | Metcalfe | |
| 2013/0261629 A1 | 10/2013 | Anthony et al. | |
| 2013/0261750 A1 | 10/2013 | Lappin | |
| 2013/0261755 A1 | 10/2013 | Anthony et al. | |
| 2013/0325131 A1* | 12/2013 | Roche ....................... A61F 2/40 623/19.13 |
| 2014/0025173 A1 | 1/2014 | Cardon et al. | |
| 2014/0236304 A1* | 8/2014 | Hodorek .................. A61F 2/40 623/19.14 |

FOREIGN PATENT DOCUMENTS

| | | |
|---|---|---|
| EP | 2672929 A2 | 12/2013 |
| EP | 2689750 A1 | 1/2014 |
| WO | 03005933 A2 | 1/2003 |
| WO | 2011073169 A1 | 6/2011 |
| WO | 2012109245 A2 | 8/2012 |
| WO | 2012125704 A2 | 9/2012 |
| WO | 2013148229 A1 | 10/2013 |

OTHER PUBLICATIONS

"Evolution of the Reverse Total Shoulder Prostheses", Reza Jazayeri, M.D., and Yong W. Kwon, M.D. Ph.D. Bulletin of the NYU Hospital for Joint Diseases 2011; 69(1):50-5 http://www.ncbi.nlm.nih.gov/pubmed/21332439.

* cited by examiner

INSTRUMENTS AND TECHNIQUES FOR ORIENTING PROSTHESIS COMPONENTS FOR JOINT PROSTHESES

RELATED APPLICATIONS

This application claims the benefit of the filing date of U.S. Provisional Patent Applications No. 61/921,593 filed Dec. 30, 2013, and No. 61/928,399 filed Jan. 16, 2014.

FIELD

The disclosure relates to the field of joint replacement, and more particularly total shoulder arthroplasty using prosthetic components to achieve anatomical and reverse, and revision arthroplasty.

BACKGROUND

Anatomic and Non-Anatomic Shoulder Replacement

In the field of shoulder arthroplasty, there are two general and somewhat competing points of view regarding the state of the patient's anatomy. From the point of view of some clinicians, it is desirable to aim for restoration of the native anatomy through use of prosthetic shoulder components that are shaped in a manner that is anatomically correct, particularly with regards to the shape of the prosthetic humeral head. For others, the higher objective is to aim for adapting and balancing the existing soft tissues, particularly the rotator cuff and musculature, with the shape and orientation of the replacement humeral head, even if the shape of the prosthetic head is not anatomically correct.

Shoulder arthroplasty typically requires removal of the entire head of the humerus bone, commonly at or below the anatomical neck, to accommodate insertion of a prosthesis, typically in the form of a head-bearing elongated shaft (referred to herein as a stem), into the diaphysis of the humerus, and in alternate approaches a stemless system includes a cage or other support structure that is not elongate. The head portion of the prosthesis provides an articulation surface that cooperates with an opposing articulation surface, the glenoid, which is on the boney portion of the scapula. In some instances, the head and stem of the prosthesis are unitary, while in other instances, the head and stem are provided as discrete components that are engageable by a variety of means, such as a male taper and female receiver. Within the art, there is a wide array of choices with respect to stem features, in terms of length, width, taper, and dimensions, as well as shape and texture. Likewise, there is a wide array of choices with respect to humeral head shape, dimensions, pitch, and the like.

Stemless shoulder prostheses are also known in the art. Such prostheses are offered currently in Europe commercially, and are under investigation in the United States. The stemless systems are considered anatomically accurate by nature due to the generally greater ease of component positioning as compared with systems that use stems. The stemless systems utilize spherical humeral heads in all variations. The stemless systems are particularly desirable because they involve less invasive boney operations, and because the surgical technique itself is not as technically demanding, since the final position of the prosthetic head is not constrained by the long axis of the bone due to the short length of the prosthesis. Fixation is offered in a variety of keeled, caged, caged-pegged configurations. However, poor bone quality presents concern for long-term durability of stemless arthroplasty, and poor bone quality is considered a contraindication for use of a stemless prosthesis. This limits the utility of stemless implants typically to patients who are young, since elderly patients—who are most often in need of joint replacement—often have osteopenic bone, and are thus excluded from the possibility of stemless shoulder arthroplasty.

The anatomic approach involves restoration of the humeral head to its pre-diseased state, with utilization of spherical humeral head components with proportional diameter and thickness. In contrast, the non-anatomic approach involves humeral head replacement with soft-tissue balancing of the rotator cuff utilizing spherical humeral head components of varying thicknesses. Generally within the art, reverse shoulder arthroplasty is considered non-anatomic shoulder replacement because the native glenoid side of the shoulder is converted to a sphere to mimic the humerus (glenosphere), while the humeral side is converted to mimic a glenoid (typically through replacement of the humeral head with a cup shaped implant).

Desired features of anatomic implants include replication of humeral neck angle, version, and posterior and medial offset. In the current art, stemmed arthroplasty systems are the most prevalent, and essentially all stemmed arthroplasty systems use spherical humeral heads. The conventional belief is that roughly one-third of a sphere is considered to be the most anatomically correct shape of the current offerings. Regardless of head size, the ratio of the head height to the radius of curvature is about 3:4. Clinical outcomes in patients who have received anatomically correct prostheses are generally regarded as superior when compared to soft-tissue balancing techniques using non-anatomically shaped (i.e., anatomically incorrect) prostheses.

Whether or not an implant is anatomically correct, some implants in the art are designed to be usable in either a standard to a reverse configuration. Typically within the art, convertible implants allow the surgeon to convert by removing the standard prosthetic head from the stem, and replacing the head with a cup (to mimic the glenoid) (examples within the art include convertible shoulder arthroplasty systems by Biomet, Zimmer, Tornier, Exactech). With such prostheses, the cup sits on top of the bone cut rather than being recessed within the bone. A disadvantage of this technique and prosthesis design is that the humerus becomes overlengthened or distalized, predisposing the patient to nerve stretch injury, joint stiffness, and acromial fracture. Thus, while these convertible systems offer the benefit of a less invasive reoperation, the trade off is increased risk of surgical complications and inferior biomechanical outcomes, all of which are due to the increased height of the implant that result from placement of the cup above the bone cut. This is particularly true with respect to reverse shoulder revisions when compared to primary reverse shoulder arthroplasty that is achieved with a reverse-specific implant where the cup is recessed into the proximal humerus bone (examples within the art of primary reverse shoulder arthroplasty systems include those by DJO Surgical, DePuy, and Tornier). Arm lengthening, nerve palsies, joint instability, impingement, joint stiffness, acromial fractures, and difficulty with prosthesis conversion that ultimately leads to stem extraction and bone fracture are all examples of undesirable clinical outcomes resulting from current convertible and primary arthroplasty systems.

Most reverse shoulder arthroplasty systems are designed to deliberately shift the rotational center of the joint in order to take what is believed to be best advantage of the remaining musculature by tensioning the deltoid to compensate for loss of rotator cuff function. The approach yields a distal shift of the arm/humerus (i.e., towards the direction of the patient's feet). This distal shift is achieved through an increase in the overall length of the humerus through the height of the implant beyond the cut line of the humeral head. While there are perceived advantages to this approach, known problems that come with increased distalization of the arm include 1) acromial scapular fracture, and 2) nerve injury from the stretch on the nerves. Indeed, while some experts may tout the advantages of increasing deltoid tension, others report that " . . . an increase in passive tension of the deltoid on the acromion, can lead to fatigue, stress, or complete fracture [Hamid N, et al. Acromial Fracture After Reverse Shoulder Arthroplasty. Am J Orthop. 2011. 40(7): E125-E129]. Werner et al reported a 7.3 incidence of scapular fracture in revision cases, and a 6.3% incidence during primary arthroplasty [Werner C M, et al. Treatment of painful pseudo-paresis due to irreparable rotator cuff dysfunction with the Delta III reverse-ball-and-socket total shoulder prosthesis. J Bone Joint Surg Am. 2005.87:1476-86]. Others have reported a 7.7% incidence of neuropraxia during revision reverse shoulder arthroplasty [Total Reverse Shoulder Arthroplasty: European Lessons and Future Trends. Seebauer L. Am J Orthop. 2007. 36(12 Supplement): 22-28.]. The high incidence of nerve injury is probably due to the stretch on the brachial plexus nerves that occurs as the humerus is lengthened. Especially in patients with stiff, contracted shoulders, it is not advisable to over-lengthen the arm. In view of these undesirable clinical effects that derive from the mechanical lengthening of the bone, there is a need to provide an arthroplasty system that is specifically designed to avoid distalization.

Yet another challenge in the art is the absence of anatomically correct head articulation surfaces. It is know that the native anatomical shape of the humeral head is not spherical, but elliptical (i.e., where the cross section of the humeral head has a radius of curvature in the superior to inferior dimension that is greater than the radius of curvature of the cross section in the anterior to posterior dimension). Recent research has shown that a prosthetic humeral head having a cross sectional shape adjacent to the bone cut that is elliptically-shaped and a generally spherical center point would theoretically allow a patient to have improved shoulder range of motion and function postoperatively. However, because the center of rotation of the humeral head is offset from the long axis of the humeral bone, it has been impractical for any shoulder implant company to create a prosthesis with an elliptically-shaped prosthetic humeral head. Merely coupling an elliptically-shaped head with a traditional stemmed prosthesis design would present difficulties accounting for the surgeon's need to simultaneously achieve the proper head size, correct rotational orientation of the elliptical head, and the proper amount of superior to inferior and anterior to posterior offset relative to the stem.

Moreover, in many shoulder surgeries, only the humeral portion of the joint is replaced while the native glenoid is left intact, presenting a challenge of matching the articulating surface of the head prosthetic with the native articulating surface of the glenoid. This challenge is not present in total arthroplasty, where both the humeral and the glenoid portions are replaced with prosthetics. Ideally, a shoulder arthroplasty system would provide a wide range of head choices and offsets to most precisely match the patient's native anatomy. With such a system, a near perfect match could be achieved in a hemi-arthroplasty, and in if the system were modular, could be adapted in a revision to provide an ideal match if the shoulder is converted to either a total arthroplasty or to a reverse shoulder arthroplasty. The current art does not provide such modular systems, thus, to accomplish the desirable offsets with traditional stem designs, whether using spherical or elliptical heads, it would be necessary to stock an essentially infinite inventory of prosthetic heads and/or stems with variable offsets for achieving the desired shape, size and positioning, which is, of course, economically impractical.

Another challenge in joint replacement is the general requirement for complete implant removal in the instance where a corrective or revision surgery is needed with a primary arthroplasty system. A common feature among the shoulder arthroplasty devices in the art is that they are typically designed for a single use, and typically cannot be repurposed in a later surgery on the same patient. That is to say that any post implantation procedure which the patient may require due to further bone or soft tissue deterioration, such as a revision or conversion to a reverse configuration, typically requires a bony procedure wherein all or a portion of the implanted prosthesis must be removed from bone in order to allow implantation of a new device. It is well known that in a percentage of initial shoulder arthroplasty cases, the patient will require revision surgery due to device failure, infection, or further degeneration of the bone or soft tissues of the joint. In some specific situations, the revision will require conversion of the humeral side of the joint from a standard implant to a reverse implant. It is desirable, though typically not possible, to avoid any bony procedure during revision cases because there is a high risk of humeral fracture and/or bony destruction when the surgeon attempts to remove a well-fixed humeral component from the humerus. It is desirable to advance the art with devices that achieve structural stability of an implant within the bone while retaining the ability to remove the device without bone fracture or catastrophic loss of bone during removal.

The objective of implant stability is addressed, in the context of long bones, through implant length, proximal diameter, and material selection and surface treatment that can enhance bony ingrowth on the implant. In the art of shoulder arthroplasty, there are a variety of short-stemmed and stemless devices that have implant surface features that encourage bony ingrowth and implant dimensions that are intended to achieve stability. While these features are helpful to encourage securement within bone, they are developed based on averages within a broad patient population, for example in terms of proximal humerus head and diaphysis dimensions, and contribute to some of the other challenges of arthroplasty in that they provide only a limited range of possible device configurations and features for achieving bony fixation. And it is a well known problem that removal of a prosthesis component that is well fixed in the bone is made more difficult when the structural features of implant components limit the surgeon's ability to apply surgical instruments such as an osteotome to free the prosthesis from the bone, especially in the metaphyseal and diaphyseal regions. It is the very structural elements that provide the opportunity for enhanced fixation that also lead to significant bone damage and loss in the likely event that a revision is needed. The art presently lacks arthroplasty implants with features that enable achievement of bony fixation and enable removal of components for revision to minimize bone loss while enabling the repurposing of the primary implants for alternate use.

A need exists to provide a humeral prosthesis that is designed to be modular and adaptable to enable a closer approximation of native anatomical fit for a broader range of patients rather than a patient population. Further, there is a need for a device that mitigates the problems associated with height position of a prosthesis in the humerus bone at the time of the index procedure and/or a revision surgery so that distalization of the humerus is avoided if conversion to a reverse shoulder arthroplasty is required. And there is a need for devices that are optimized for proximal bony ingrowth and distal (diaphyseal) stability to achieve short and long term device stability while retaining the ability to revise and possibly remove the implant without catastrophic bone effects. While some devices and device features exist within the art that are designed to protect against humeral bone loss in revision surgeries, there remains a need for a system that enables replacement or conversion of a humeral prosthesis without the requirement for bony procedure or at least minimal need for removal of implant from within the bone. To address needs in the art, including the several needs identified, this disclosure provides a system that is modular and convertible and optimized achieve closer approximation of a patient's native anatomy, including avoidance of arm distalization, avoidance of surgery-related bone loss, while enabling a wider range of options for matching anatomy on during the index procedure as well as during surgical revision.

SUMMARY

This disclosure is directed to components, systems, and methods for shoulder arthroplasty. In particular, the disclosure provides solutions for achieving anatomically correct hemi and total arthroplasty and reverse arthroplasty, in primary and revision surgery. In particular, the disclosure provides solutions for addressing the challenges faced when a standard shoulder arthroplasty requires revision surgery, including revision from standard to reverse shoulder arthroplasty wherein the orientation of the humeral head and glenoid are switched from their typical anatomical orientation. And this disclosure provides solutions currently lacking in the art that would enable a surgeon to achieve revision arthroplasty without risk of substantial humeral bone loss or fracture, among other benefits. This disclosure also provides solutions for achieving an optimized anatomical match of an arthroplasty system to a patient's anatomy. Surgical methods and techniques are provided for achieving placement of arthroplasty components, and for selecting and optimizing anatomical positioning of components to best match a patient's native anatomy.

According to the instant disclosure, a variety of implant embodiments are disclosed as well as techniques for selecting implant components to achieve a close replication of the native anatomy of a patient receiving primary native or reverse orientation shoulder arthroplasty, as well as revision. Thus, embodiments are provided that create a more anatomic suite of standard and stemless implants that are more biomechanically sound both at the time of primary standard total arthroplasty, hemi-arthroplasty and reverse shoulder arthroplasty surgery, as well as during revision surgery.

As further described herein, some of the benefits of the disclosed implants and techniques pertain to a "convertible offset coupler" or "coupler" which is alternately referred to herein as a "metaphyseal shell" in the context of shoulder arthroplasty systems, and which functions in some aspects to position and retain an implant component, such as, for example, a humeral head or a cupped reverse prosthesis (a "concave cup" or "concave poly cup") for replicating a glenoid feature on humeral bone. In some exemplary embodiments, this metaphyseal shell is positioned by countersinking in bone, such as the cut humeral head bone in the case of shoulder arthroplasty, in a region that is proximate to or within the metaphysis (wide portion of the long bone between the epiphysis—head—and the diaphysis—the shaft). In other embodiments, this metaphyseal shell is positioned partially within the bone or on the cut surface of the bone for cases in which achieving anatomical match in a patient necessitates increased height on the superior aspect of the humerus.

Advantageous features of the metaphyseal shell that are described further herein include: an eccentric engagement feature or coupler on the back or inferior (bone facing) side, such as a standard taper coupler (Morse-taper in some embodiments), that is selected for engagement with a bone stem, plug or cage (selected in size for anatomical match with the metaphyseal/diaphyseal portions of the long bone) to replicate and achieve native or normal humeral posterior and medial offset. And, on its top or superior (articulation surface facing) side, a seat, such as a recess, that is adapted to accept both humeral head and humeral cup (reverse prosthesis) components. The metaphyseal shell addresses the mechanical challenge of orientation of spherical and most particularly non-spherical humeral head components using the coupler to achieve any anatomically desired offset in either or both the inferior/superior axis and anterior/posterior, and selecting for placement using instrumentation as described herein to achieve optimal anatomical alignment of the prosthetic articulation surface relative to the humeral bone.

In an exemplary embodiment according to this disclosure, a modular arthroplasty assembly includes the components of: (a) a convertible offset coupler bounded on a first side by an implant surface adapted to receive an implant component, and bounded on an opposite second side by a bone anchor engagement surface ("metaphyseal shell") (b) an prosthesis component selected from one of a humeral head ("head") and a cupped reverse prosthesis ("cup"), and (c) a bone anchor configured to be inserted in bone and adapted for engagement with the convertible offset coupler ("stem" or "plug").

According to the various embodiments, the modular system for long bone arthroplasty provides prosthesis, anchor and coupler components that are engageable to provide an arthroplasty assembly wherein the position of the prosthesis component can be varied rotationally around a shared central engagement axis with the coupler component, the position of the anchor component relative to the coupler component can be varied in two dimensions on a plane that is perpendicular to the central engagement axis of the coupler and prosthesis components by selecting the coupler component from an array comprising a plurality of coupler components that include variably positioned anchor engagement features. In accordance with the invention, each of at least two of the plurality of coupler components comprises at least one anchor engagement feature that is off-center from a center point of the coupler component, and the off-center engagement feature on each of the at least two coupler components is at a different distance in at least one dimension that is perpendicular to the central engagement axis. In use, when the coupler and anchor components are recessed into bone, the assembly achieves alignment of the bone articulation surface of the prosthesis component with the bone that is anatomically similar to a native long bone.

In the various embodiments, the stem and the metaphyseal shell are each adapted with at least or one another of a male insert and a female receiver channel (such as a Morse type taper), and optionally one or more of a pin or setscrew or other fastener to achieve engagement there between. In some embodiments, the metaphyseal shell bears on a lateral peripheral edge a surface feature that is adapted to enhancing boney ingrowth. In various embodiments, the implant surface of the metaphyseal shell and the engagement surface of the prosthesis articulating surface component have reciprocal engagement features for fixing engagement there between.

In one embodiment of a head, the head and the metaphyseal shell are each adapted with at least one or another of a male insert and a female receiver channel (such as a Morse type taper) for engagement there between. In one embodiment of a cup, the cup and the metaphyseal shell are each adapted with at least one or another of snap fit tooth engagement features for engagement there between. In some embodiments, the metaphyseal shell includes engagement features that allow engagement and fixation with each of the head and cup prostheses. In other embodiments, a metaphyseal shell is adapted with one or the other of head and cup prosthesis engagement features. Optionally, in some embodiments, the system comprises a modular diaphyseal stabilizer attachable to the distal end of the stem and selected to match the inner diameter of the diaphysis. Together, the components of the system, including the selectable engagement orientations of the components, enables adaptation to the existing anatomy of the patient and the ability to most closely achieve the native anatomy of the healthy shoulder joint so as to provide the patient with the most natural use of the shoulder.

In various embodiments, the methods include surgical techniques for preparation for and implantation of the modular arthroplasty assembly, wherein one or both the humeral stem and the metaphyseal shell are completely or partially recessed within the humeral bone. In particular embodiments, the surgical techniques for revision surgery involving previously implanted modular arthroplasty assembly enable modular adjustment, removal and replacement of the prosthesis component without substantial compromise or removal of humeral bone. In some embodiments, the surgical techniques provided herein enable conversion of a shoulder joint from native to a reverse configuration.

In various embodiments, the methods include surgical techniques for implantation of the modular arthroplasty assembly wherein the metaphyseal shell is completely or partially recessed within the humeral bone. According to the various embodiments, placement of one or both the humeral stem and the metaphyseal shell within the bone (i.e., below the cut line) allow a greater range of options with respect to establishing the desired center of rotation in the shoulder joint. It is known in the art and deemed desirable by some to distalize the humerus during a reverse shoulder arthroplasty procedure, putatively because greater height in the humeral implant distalizes the humerus and puts increased tension on the deltoid muscle to compensate for lost rotator cuff function. However, there are clinical and mechanical disadvantages to this distalization. Unfortunately, these disadvantages are not easily avoided with implant systems in the art, particularly in the case of current convertible systems, because of the increased height of the humeral implants from the extension of the stem and other components above the bone cut line of the humerus. The current disclosure, in various embodiments, provides an modular and convertible arthroplasty system that is low profile, having a substantial reduction of implant height as compared with what is know in the art. These embodiments are desirable for avoidance of distalization, particularly in reverse arthroplasty, enabling the surgeon to avoid mechanical and clinical problems associated with the rotational center of the joint, and enabling the use of other options for achieving soft tissue function to replace the rotator cuff.

Further, in accordance with some exemplary embodiments, the countersunk position of the metaphyseal shell below the bone cut allows the surgeon to achieve a more anatomical configuration than other systems can achieve at time of primary or revision surgery. In particular, the position and features of the metaphyseal shell enable substitution of articulation surface prostheses, and as needed, removal of the shell during a revision. In some embodiments, removal of the shell enables replacement with a shell having an alternate offset to enable maximum flexibility for achieving desired anatomical structure in a revision surgery.

To facilitate removal from bone, the metaphyseal shell has a lateral edge that is in some exemplary embodiments roughened or porous coated to achieve bony ingrowth for reliable fixation, while the bottom of the metaphyseal shell is smooth to prevent bony coupling in some embodiments, thus allowing for greater ease of removal from bone should that be necessary in a later procedure. Taking advantage of the convertibility, and ease of selection of head/cup implant components, the metaphyseal shell allows for minimal bone removal or manipulation at time of revision/conversion. And, as further described herein, the use of the metaphyseal shell trial with marking features enables precise and virtually unlimited increments of offset adjustability, eliminating need for large inventory of prosthetic heads and cups. The options for adjustability are particularly wide when the metaphyseal shell is used in combination with a suite of stems that are size and shape adapted for a wide range of patient anatomy.

Thus, as compared to other systems in the art, the disclosed system enables achievement of a more anatomically accurate joint replacement aimed at reducing clinically adverse consequences. And the metaphyseal shell with its eccentric taper enables a wider range of selection of head/cup orientation without compromise of height, neck angle, version, and posterior and medial offset. This offset function, together with the anatomical benefits thereby attained, finally solves a vexing challenge in the art. That is, provision for truly adaptable and convertible, anatomically accurate implants—a challenge that has been heretofore addressed, inadequately at best, with either expansive prosthetic head inventory and/or adjustable systems that sacrifice one or more of the anatomically desirable implant features such as component height, neck angle, version, and posterior and medial offset.

This disclosure describes various exemplary convertible implant components and systems, convertible shoulder prosthesis systems, and methods for implantation of these. While the description below sets forth details of features of the modular arthroplasty assembly, one of skill will appreciate that the features may also be shared by other system components, such as those that are used to determine implant size and positioning, generally referred to as trials. Moreover, the features and elements as described herein for the shoulder and humerus may be readily adapted for use in the context of other long bones.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

DETAILED DESCRIPTION

Figure 1:
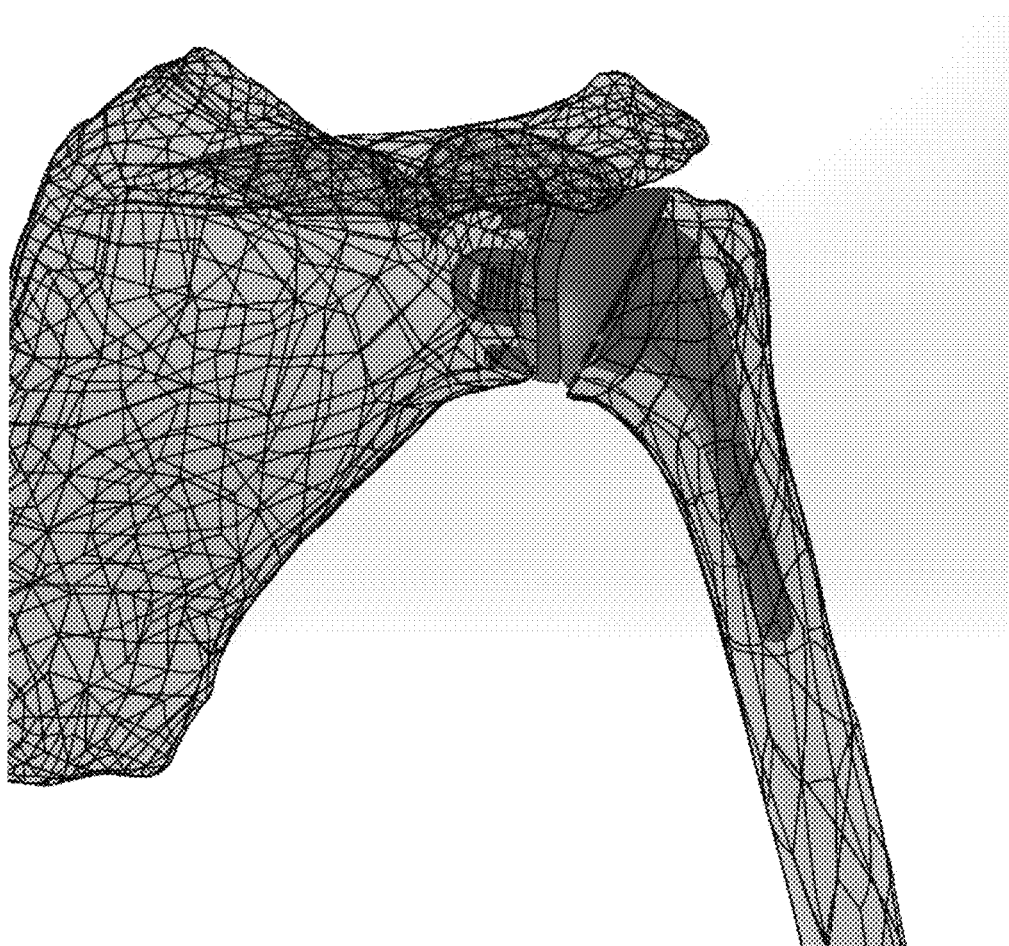
FIG. 1 shows a side view of an embodiment of a modular arthroplasty assembly with a stem ("anchor component"), assembled in the context of shoulder bone.

This disclosure describes exemplary embodiments in accordance with the general inventive concepts and is not intended to limit the scope of the invention in any way. Indeed, the invention as described in the specification is broader than and unlimited by the exemplary embodiments and examples set forth herein, and the terms used herein have their full ordinary meaning.

The general inventive concepts are described with occasional reference to the exemplary embodiments and the exemplary embodiments depicted in the drawings. Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts.

Modular and Convertible Shoulder Arthroplasty Components, Systems and Methods

Convertible Modular Arthroplasty Assembly

In various embodiments, a modular arthroplasty assembly is provided, and includes implant components, instruments, trial components including broaches, trial convertible offset couplers, and trial humeral head and trial cupped reverse prosthesis components, sizers, bits and guides, and fixation elements including adapters, screws, pins and wires. Further, in various embodiments, techniques for determining implant features and for achieving implantation of modular arthroplasty assemblies are provided.

Referring now to the drawings, FIG. 1 shows a side view of an embodiment of a modular arthroplasty assembly with a stem, assembled in the context of shoulder bone.

Figure 2:
FIG. 2 shows alternate perspective views of an embodiment of a modular arthroplasty assembly with a stem in the context of bone.
Figure 4:
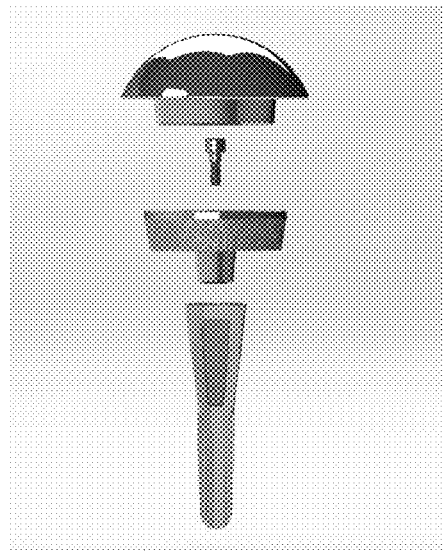
FIG. 4 shows alternate back, front, perspective and side views of an embodiment of a modular arthroplasty assembly with a stem, showing an articulation surface in the form of a spherical head, a frustoconical shaped metaphyseal shell ("coupler component") and shell-stem locking pin, and stem.
Figure 4:
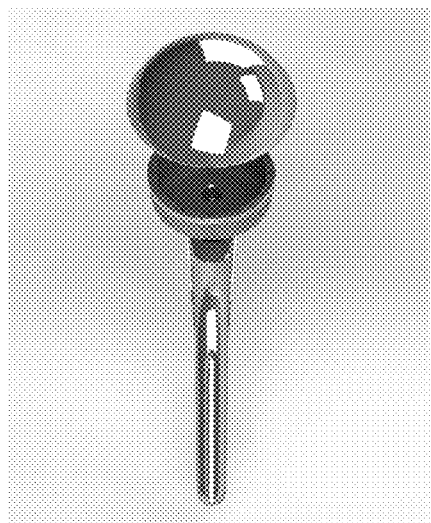
Figure 4:
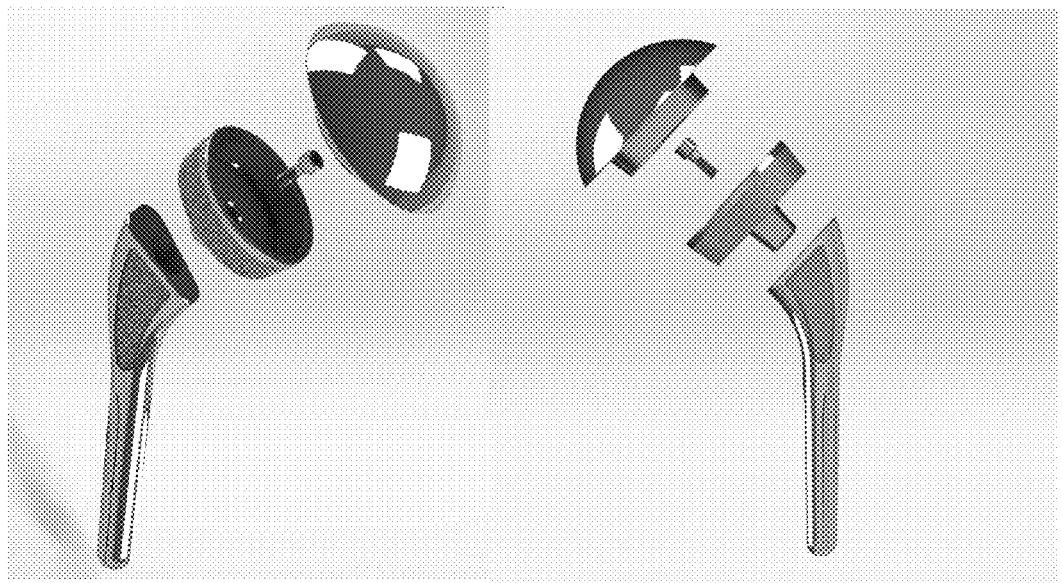

In various embodiments, the modular arthroplasty assembly includes (a) an convertible offset coupler (also referred to herein as a "coupler component" and alternately a "metaphyseal shell") bounded on a first side by an implant surface adapted to receive an implant component, and bounded on an opposite second side by a bone anchor engagement surface, (b) an prosthesis component selected from one of a humeral head and a cupped reverse prosthesis (also referred to herein as a "prosthesis component" and alternately "head" and "cup," respectively), and (c) a bone anchor configured to be inserted in bone and adapted for engagement with the convertible offset coupler (also referred to herein as a "anchor component" and alternately "stem" or "plug"). As shown in FIG. 1, the implant component is a spherical shaped humeral head. FIG. 2 shows alternate perspective views of an embodiment of a modular arthroplasty assembly with a stem and spherical head in the context of bone, and FIG. 4 shows alternate back, front, perspective and side views of an embodiment of a modular arthroplasty assembly with a stem, showing an articulation surface in the form of a spherical head, a metaphyseal shell and shell-stem locking pin, and stem.

Figure 3:
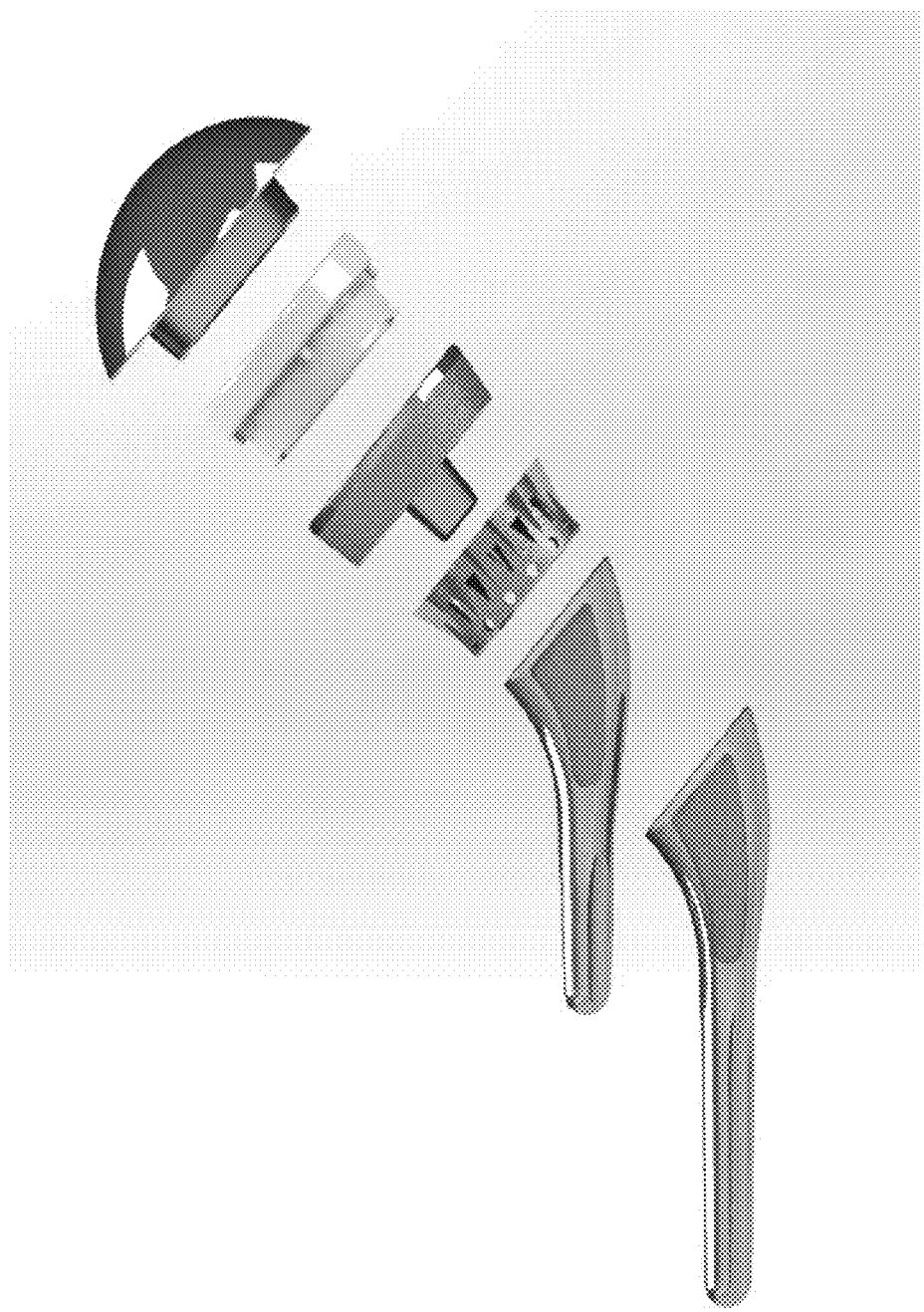
FIG. 3 shows an exploded side view of an embodiment of a modular arthroplasty assembly with a stem, showing alternate stem lengths and alternate embodiments of an articulation surface ("prosthetic component") in the form of a spherical head and a concave poly cup.

It will be appreciated that for each of the possible components of the modular arthroplasty system, at least one or more size, shape and offset options are available, and are selected from an array of sizes of heads (spherical and non-spherical), stems and plugs (of varying length, diameters, and width and depth dimensions, and metaphyseal shells of various sizes (diameters) and offsets and engagement features for prostheses components. FIG. 3 shows an exploded side view of an embodiment of a modular arthroplasty assembly with a stem, showing representative alternate stem lengths and representative alternate articulation surfaces in the form of a spherical head and a concave poly cup. Of course a wide range of possible combinations of components is available in accordance with the disclosure, and may be selected from the specific embodiments of arrays as disclosed herein and from embodiments that are within the scope of the disclosure though not specifically described in the specification and drawings.

While the above described drawings and the majority of other drawings herein depict embodiments of the modular implant system that comprise stemmed arthroplasty systems, it will be understood and appreciated by one of ordinary skill in the art that other arthroplasty systems are know, as described elsewhere in this disclosure, and that the modular system may be adapted to providing stemless systems for implanting prosthetic devices. FIG. 7-FIG. 10 show alternate views of such stemless systems, which encompass the use of bone anchors in the form of short plugs, stems, and cages (generically referred to herein as "plugs") with a variety of surface features and anchors and the like. These stemless systems may be provided in monolithic forms that are adaptations to allow for complete excision from bone in the event of revision surgery, and in alternate forms as modular systems in which one or all of the prosthesis articulation surfaces, metaphyseal shells, and anchors may be removed for revision surgery. Plugs for stemless uses may be solid, hollow and may include screws, anchors, suture holes and surface features for optimizing press fit engagement within the metaphyseal bone and optionally at least a portion of the canal of the diaphysis. In contrast to stems as described further herein, and which are intended for insertion of their distal portions within the diaphyseal canal and press-fit of their proximal portions within the metaphysis, stemless plug embodiments are press fit within the metaphysis without reliance on any stabilizing and anti-rocking protective function of the distal portion of a stem.

Convertible Offset Coupler (Metaphyseal Shell)

Figure 5:
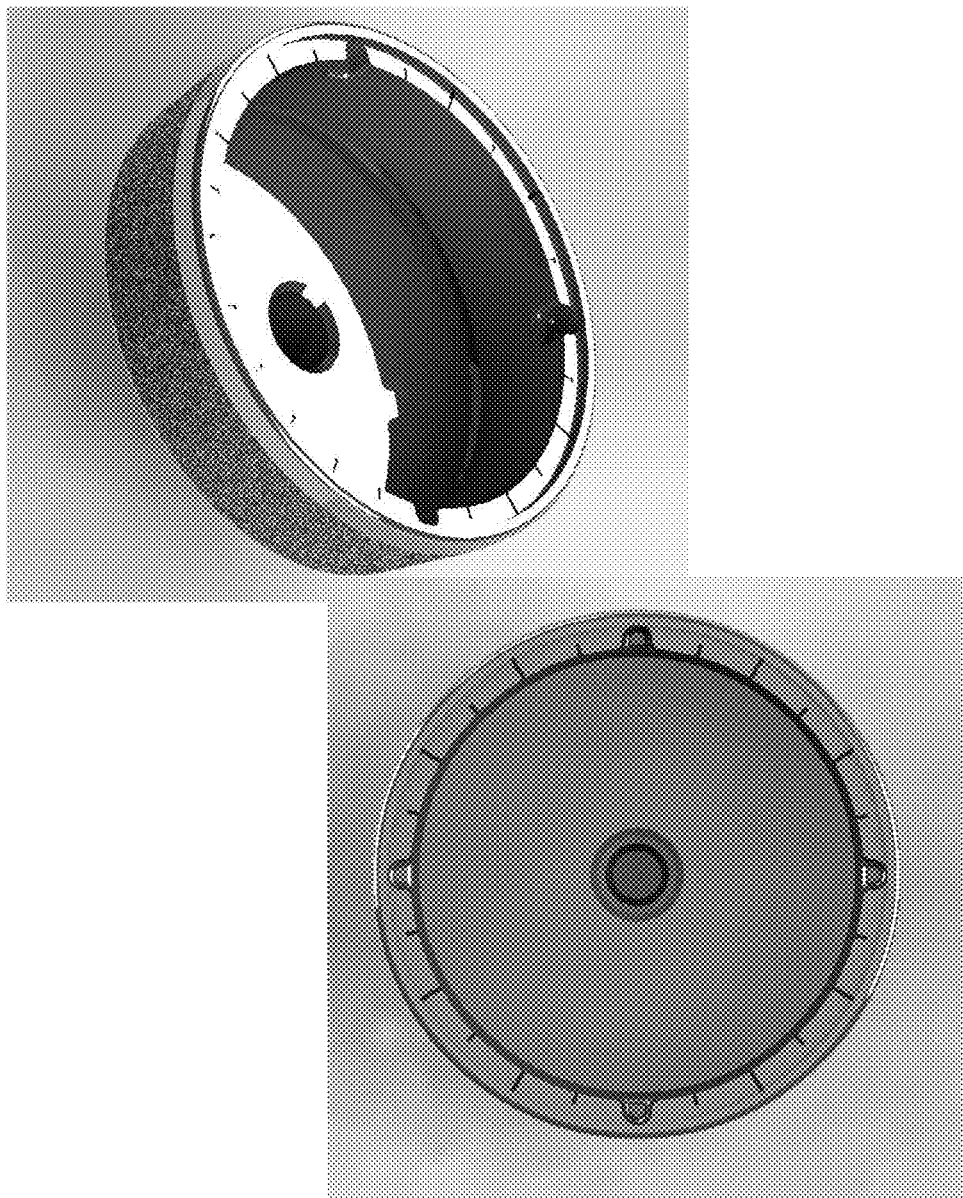
FIG. 5 shows alternate perspective and top views of an embodiment of a metaphyseal shell.
Figure 6:
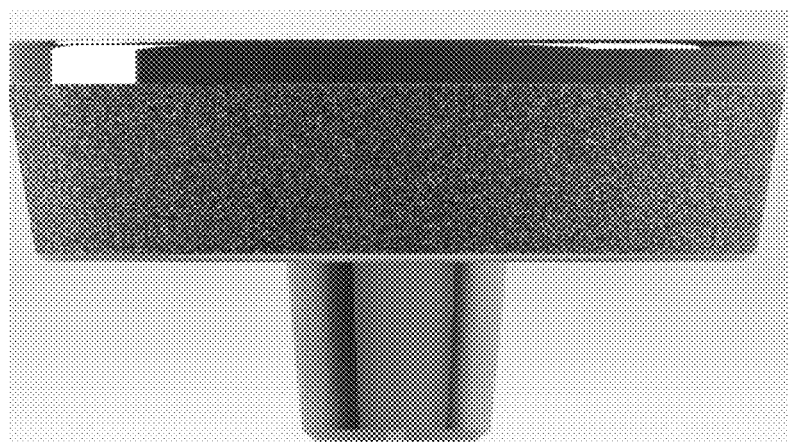
FIG. 6 shows alternate side and cross-sectional perspective views of an embodiment of a metaphyseal shell.
Figure 6:
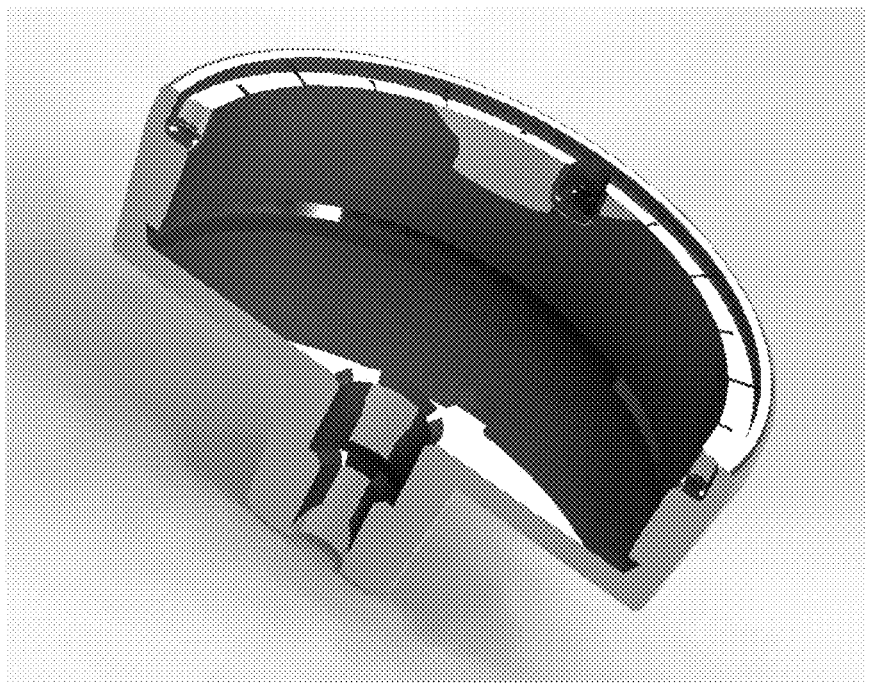
Figure 7:
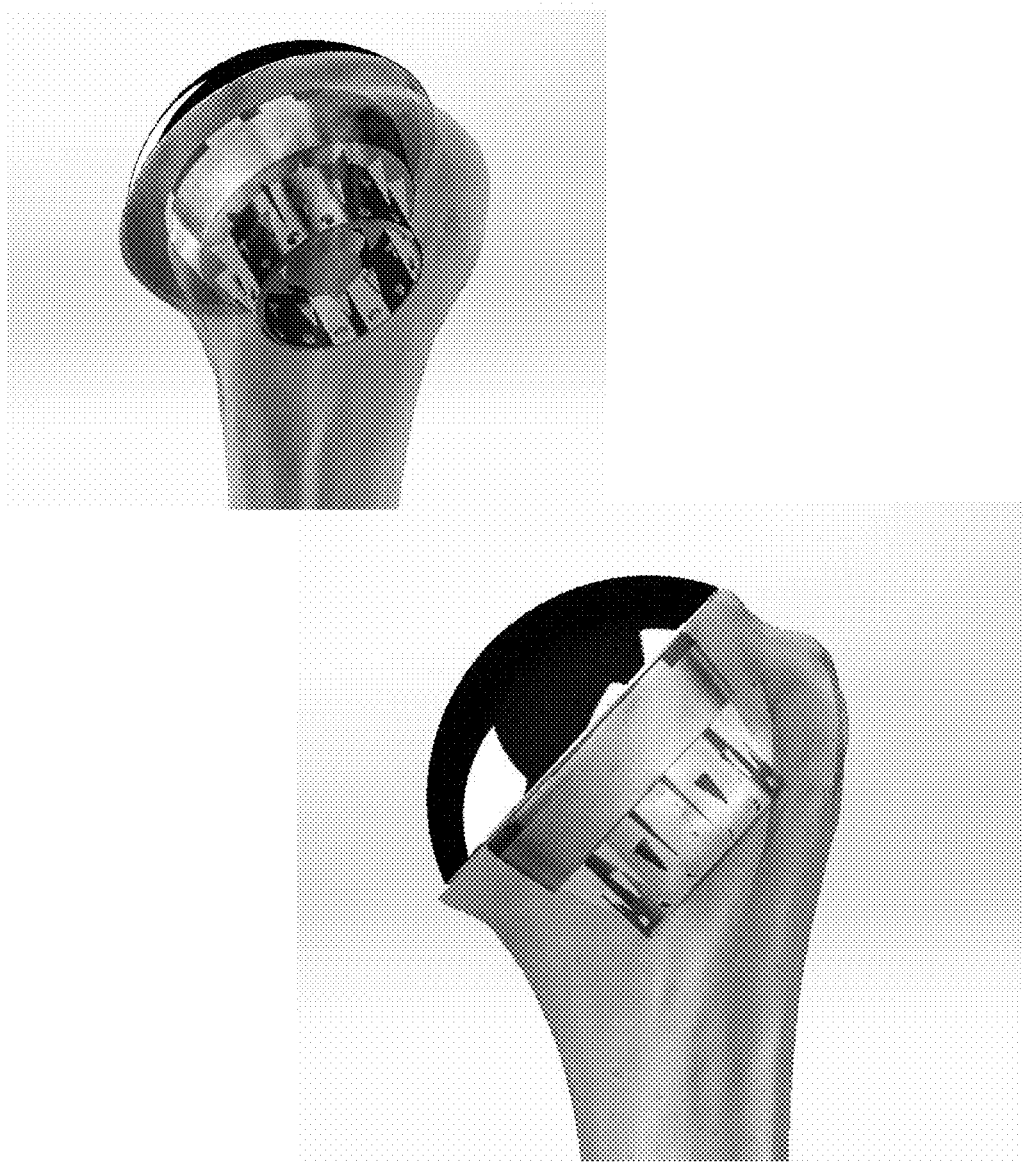
FIG. 7 shows alternate perspective views of an embodiment of a stemless arthroplasty assembly with a plug (alternate embodiment of an "anchor component" in the form of a cage) with an articulation surface in the form of a spherical head, assembled in the context of bone.
Figure 8:
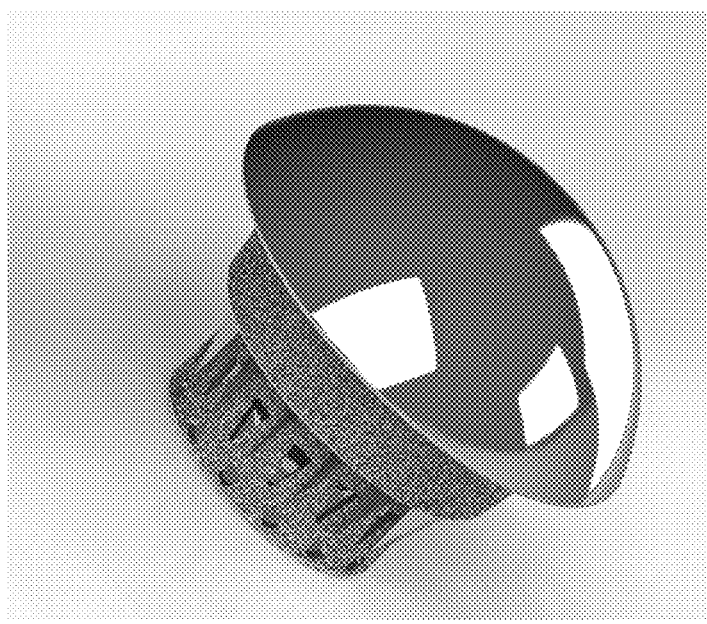
FIG. 8 shows perspective views of two alternate embodiments of a stemless arthroplasty assembly with a plug, each with an articulation surface in the form of a spherical head.
Figure 8:
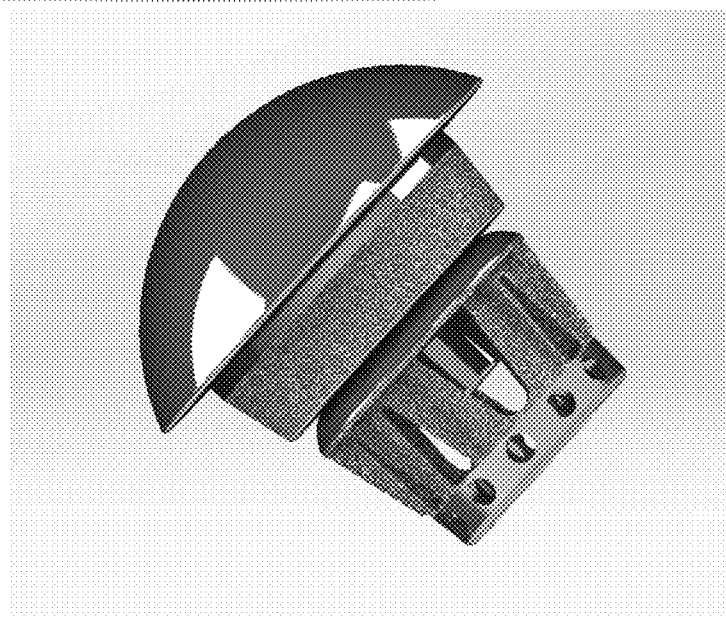
Figure 9:
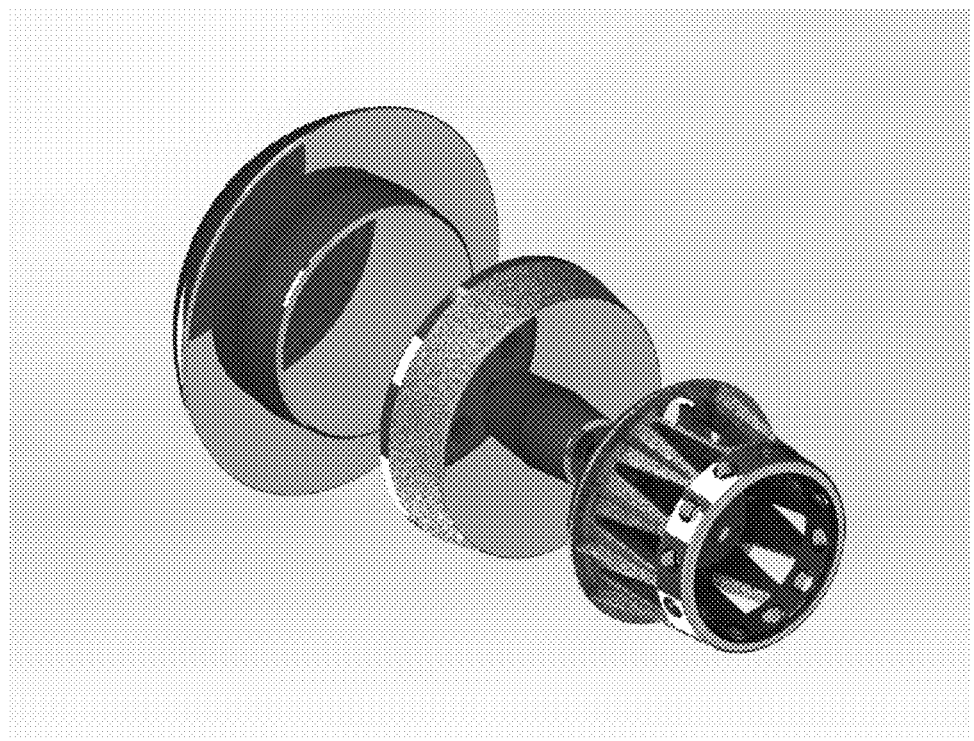
FIG. 9 shows an exploded perspective view of an embodiment of a modular stemless arthroplasty assembly with a plug with an articulation surface in the form of a spherical head.
Figure 10:
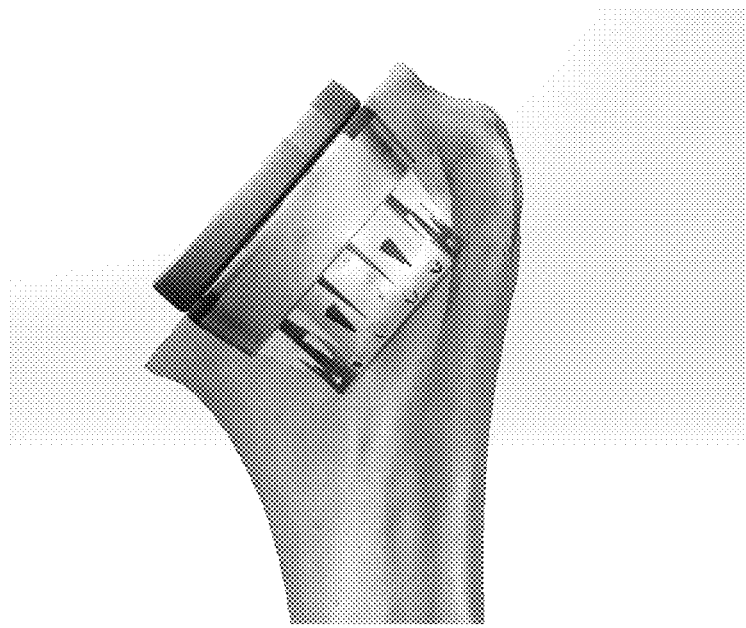
FIG. 10 shows alternate views of an embodiment of a stemless arthroplasty assembly with a plug and with an articulation surface in the form of a concave poly cup, assembled in the context of bone and alone.
Figure 10:

Referring again to the drawings, FIG. 5 and FIG. 6 show a representative embodiment of a metaphyseal shell in accordance with the disclosure. In various embodiments, the overall shape of the metaphyseal shell is generally cylindrical, with an outer surface and dimensions that are adapted for insertion at least partially within humeral bone and is bounded on a first side by an implant surface adapted to receive an implant component, and on an opposite second side by a bone anchor engagement surface. In some embodiments, the metaphyseal is adapted with at least or one another of a male insert and a female receiver channel (such as a Morse type taper), on one or both opposing sides, and optionally adapted to receive one or more of a pin or setscrew or other fastener to achieve engagement with at least one of the prosthesis component and the bone anchor.

In some embodiments, the metaphyseal shell bears on a lateral peripheral edge a surface feature that is adapted to enhancing boney ingrowth. Accordingly, in some embodiments, all or a portion of the outer surface of the metaphyseal shell may be adapted with surface texturing to encourage bone ingrowth or ongrowth. In addition, the stem engagement surface may be adapted with surface texturing to enhance engagement therebetween. In various embodiments, the metaphyseal shell includes at least one engagement feature that allows engagement and fixation with each of the head and cup prostheses. In some embodiments, a metaphyseal shell is adapted with two or more head and cup prosthesis engagement features. In other embodiments, a metaphyseal shell is adapted with one or the other of head and cup prosthesis engagement features.

Figure 11:
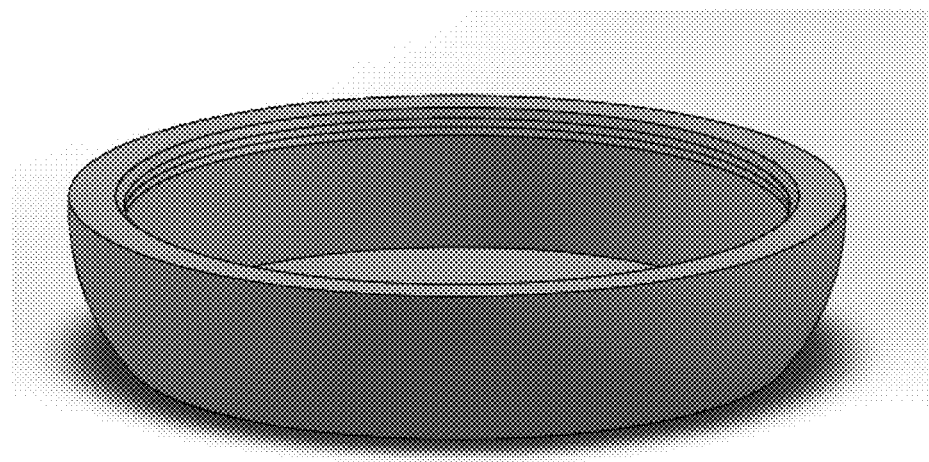
FIG. 11 shows a side view and a side view in cross section of an embodiment of a metaphyseal shell having a frusto-hemispherical shape.
Figure 11:
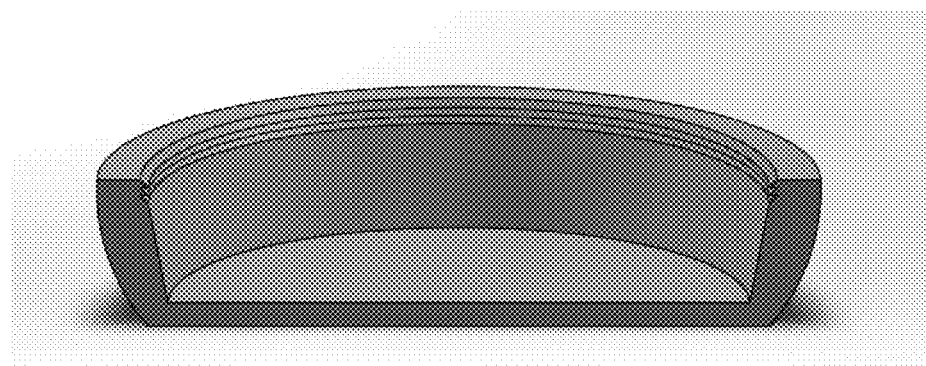
Figure 12:
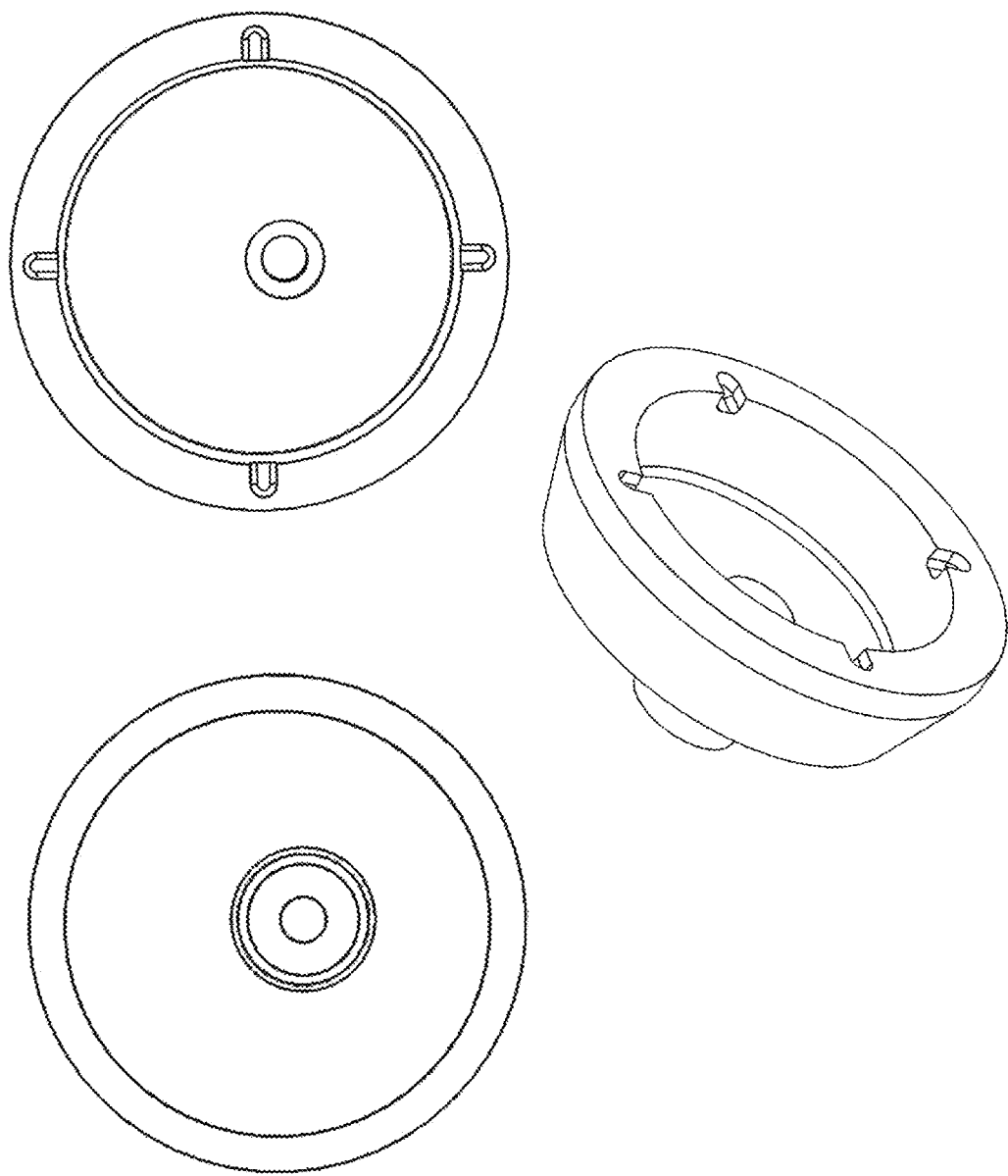
FIG. 12 shows a top view and a side view of an embodiment of a metaphyseal shell.
Figure 13:
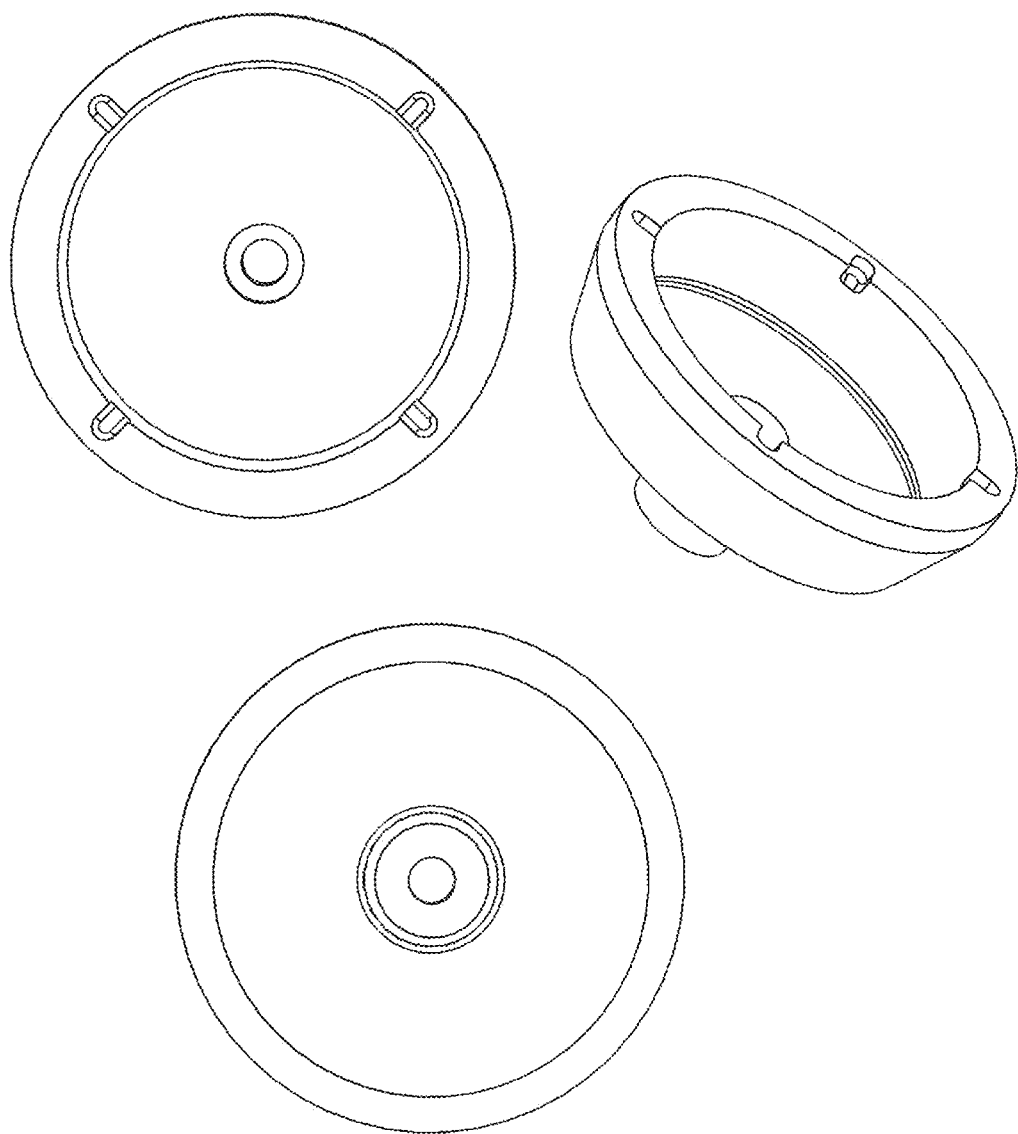
FIG. 13 shows a top view and a side view of an alternate embodiment of a metaphyseal shell.

Referring again to the drawings pertaining to the metaphyseal shell, FIG. 11-FIG. 15 show alternate views of a representative embodiment of a metaphyseal shell from the perspectives of the top (essentially superior surface), bottom (essentially inferior surface), side (essentially lateral surface) and side cross section. Referring now to FIG. 12, which shows various views, including a bottom view of an embodiment of a metaphyseal shell, in some embodiments, as depicted in the drawings, the metaphyseal shell includes a feature adapted for engagement with a bone anchor (stem or plug). As shown in the depicted embodiment, the engagement feature is in the form of a standard or Morse taper. According to various embodiments, the taper feature may be of varying length, and may be cylindrical or tapered. In various embodiments, the position of the insert on the engagement surface may be varied. For example, the insert may be centered, or it may be offset from the center at any of desirable selected positions to allow adaptability to the relative positioning of the engaged stem and metaphyseal shell.

Figure 15:
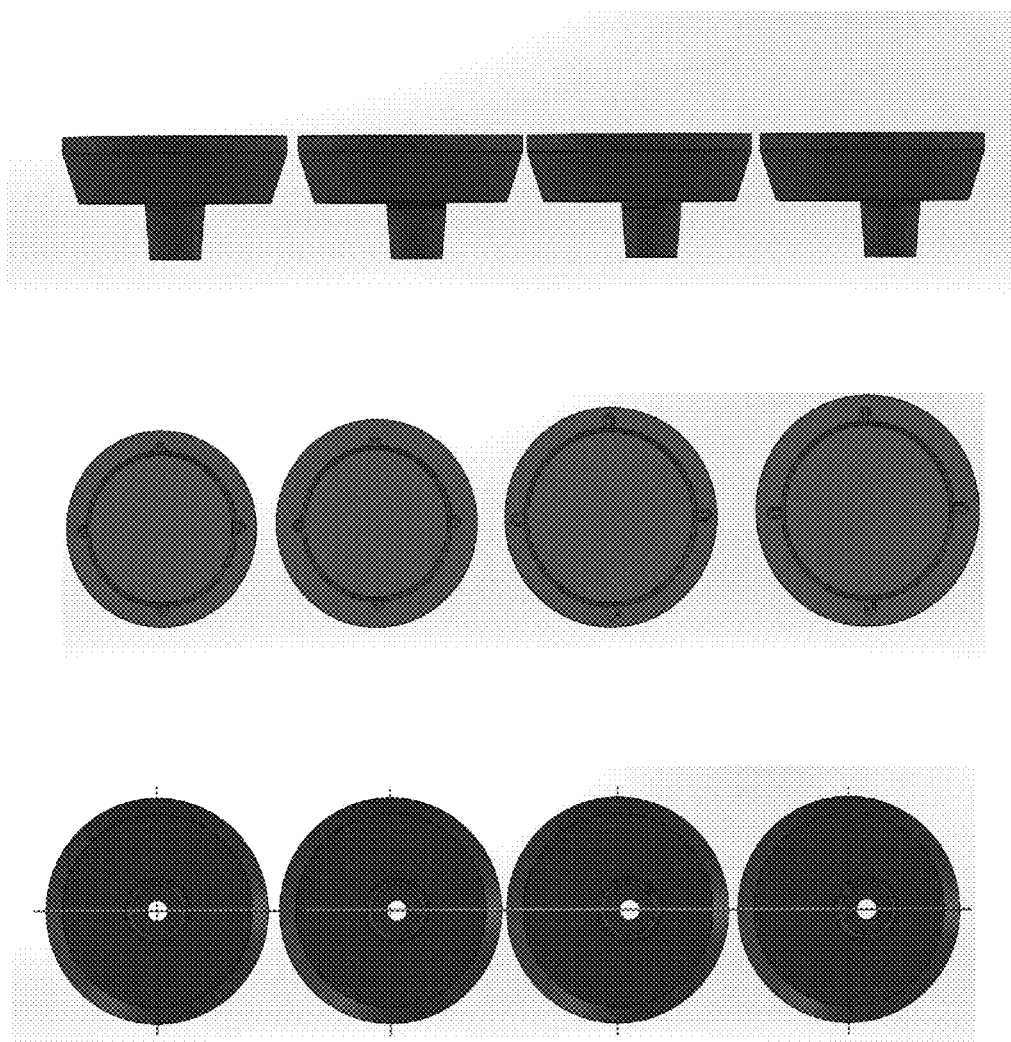
FIG. 15 shows an array of sizes of a representative embodiment of a metaphyseal shell shown from the side, the top and the bottom.

Referring now to FIG. 15, which shows an array of sizes of a representative embodiment of a metaphyseal shell shown from the side, the top and the bottom, the position of the anchor engagement feature may vary to provide an array of shells for selection to provide a customized fit and engagement for a head or cup prosthesis. In the various embodiments, a metaphyseal shell with an offset for engagement with an anchor is selected from offsets ranging in mm and increments thereof from 0 to 20 mm, and includes 0, 1, 2, 3, 4, 5, 6, 7, 8, 9, 10, 11, 12, 13, 14, 15, 16, 17, 18, 19, 20. In some representative embodiments, the range of offset may be from 0 to 10, and in some specific embodiments, the offset may be from 0 to 6. Referring again to the drawings, FIG. 15 shows an exemplary set of shells representing offsets of 0, 1, 2, and 3 mm. It will be appreciated that any range of offsets may be provided, and that series of offsets on shells of different diameters and heights, as described herein below, may be provided. In use, in a representative example of a modular arthroplasty system, as depicted in the drawings, a shell is selected for its height, diameter, and engagement feature offset using tools for offset measurement as described further herein below. The selected shell is placed in the bone, its male taper engaged with the female taper of the stem; a set screw is inserted through the taper to engage the metaphyseal shell with the stem to secure the implant system in preparation for engagement with the head or cup prosthesis.

Figure 14:
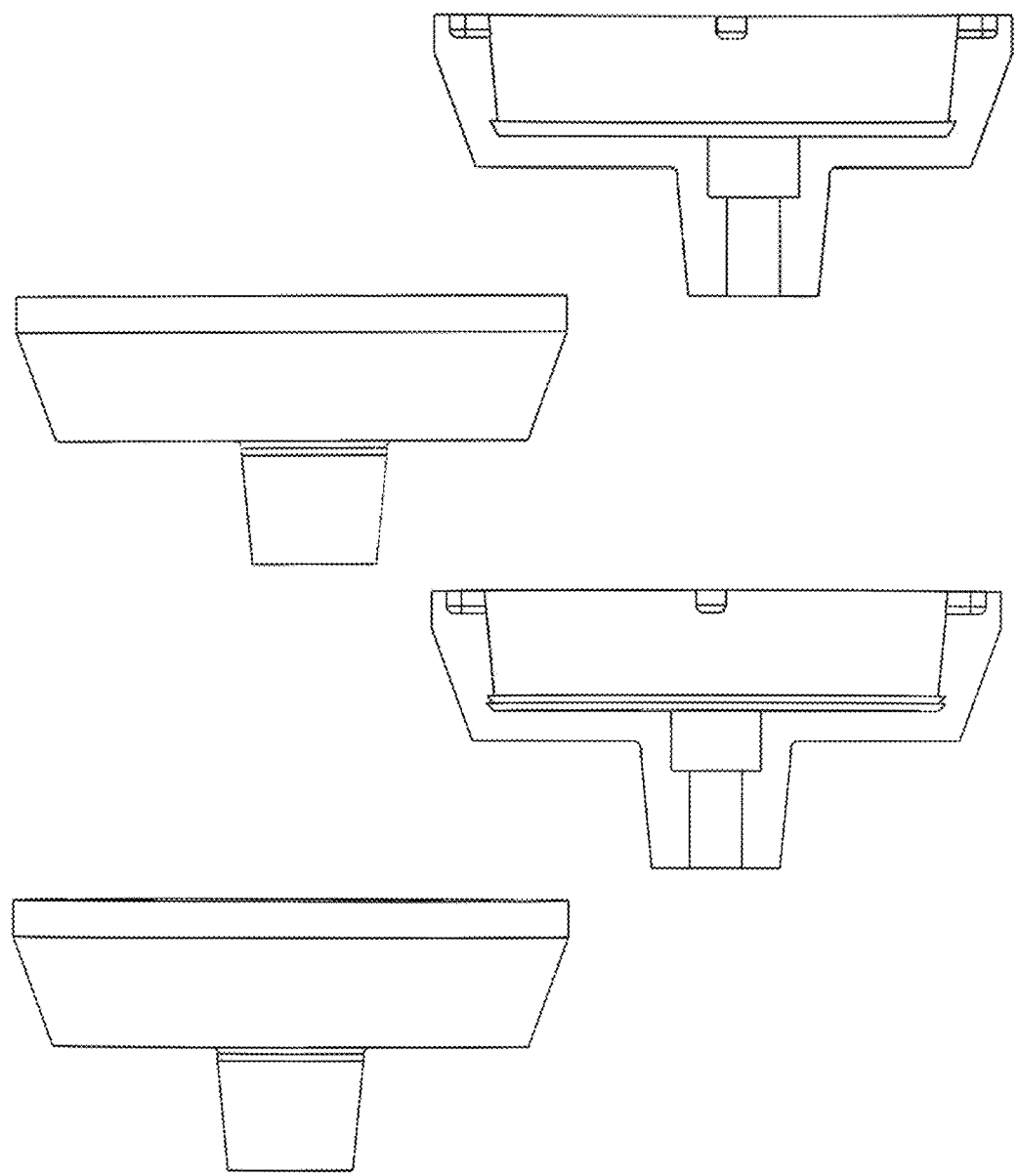
FIG. 14 shows a side view and a side view in cross section of an embodiment of a metaphyseal shell, and a side view and a side view in cross section of an alternate embodiment of a metaphyseal shell.
Figure 17:
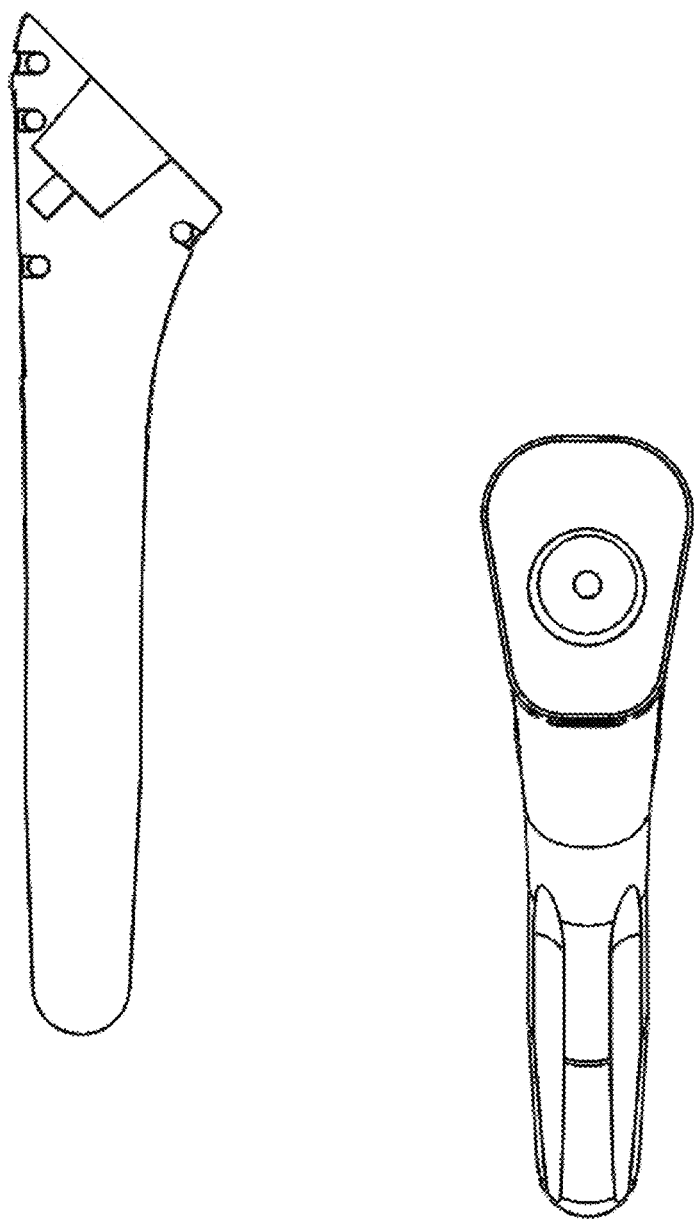
FIG. 17 shows a side view of an embodiment of a diaphyseal stem, in longitudinal cross section, and a front view of an embodiment of a diaphyseal stem, in cross section along a plane that is parallel to the proximal face.
Figure 18:
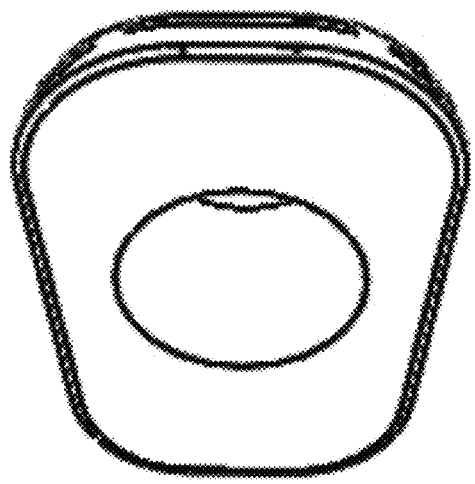
FIG. 18 shows a top view of an embodiment of a diaphyseal stem, and a bottom view of an embodiment of a diaphyseal stem.
Figure 18:
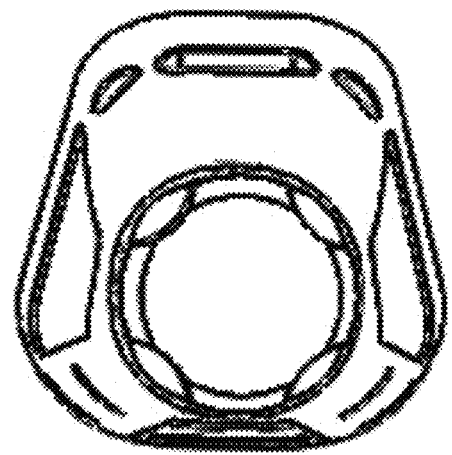

As described herein, fixed engagement between the shell and anchor is achieved using a fixation element, such as, for example, a screw, set screw or other fastener. Referring now to FIG. 14 which shows side views of alternate embodiments of a metaphyseal shell, including in cross section, the shell is adapted with threading in a bore through the anchor engagement taper, the bore being threaded for receipt of a screw. A corresponding bore in the anchor, as shown in FIG. 17, is adapted for concentric alignment with the through bore in the shell and likewise can receive a screw. As shown in FIG. 4, a threaded locking pin or screw is passed via threaded engagement through the two bores to secure and fix the stem and shell together. It will be appreciated that the use of supplemental engagement means between the shell and the anchor components is optional, and that in some embodiments the supplemental engagement means is not present, while in other embodiments, alternate supplemental engagement means may be used. It will be appreciated by one of skill in the art that a variety of fixation elements may be used to achieve fixation, including screws having continuous as well as variable threading and other engagement means such as snap fit pins, expandable screws and other fixation means known in the art. Likewise, the dimensions of such elements may vary in order to meet the length and diameter requirements of the shell and stems to be engaged. The examples shown herein are representative and are not limiting.

Referring again to FIG. 15, an array of sizes of a representative embodiment of a metaphyseal shell is shown from the side, the top, and the bottom. It will be appreciated by one of skill in the art that the specific dimensions of metaphyseal shells may vary, depending on the bone receiving the shell. In the case of the humerus, the representative sizes of shell include a shell height (superior to inferior, or proximal to distal in the sense of articulation surface to bone surface) of about 10 mm, which tapers proximal to distal in the manner of a Morse taper for enhanced engagement with the bone. Representative FIG. 12 and FIG. 14 show this taper feature as a generally frustoconical shape. Of course, in alternate embodiments, such as shown in FIG. 11, the shape may be frustohemispherical, or may have another shape that is either cylindrical with flat sides or another shape with curved sides similar to those shown in FIG. 11. The peripheral profile of the shell will influence the surgical technique for preparing bone, and as such, the techniques shown in this disclosure and as depicted in the drawings may vary in order to prepare bone for receiving such alternate metaphyseal shell shapes.

Referring again to FIG. 15, in accordance with the representative array, the metaphyseal shells vary in diameter from about 30 to 45 mm, more particularly from 34 to 40 mm, and in some specific embodiments include sizes that are 34, 36, 38 and 40 mm in diameter, respectively. Of course other sizes and incremental portions thereof are possible, and can range from 5 mm to more than 100 mm in diameter depending on the subject. Thus, shells may be provided in heights ranging in mm increments and fractions thereof from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100, and in diameters in mm increments and fractions thereof from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100.

Referring again to the drawings, FIG. 12 also shows perspective and top views of an embodiment of a metaphyseal shell. The depicted metaphyseal shell comprises an prosthetic implant engagement surface that is opposite from the stem engagement surface, and is adapted to receive various modular prosthesis components, such as a convex humeral head having a circular cross sectional shape or an elliptical shape whose purpose is to articulate with a native glenoid or prosthetic glenoid, or alternatively a concave cup whose purpose is to articulate with a glenosphere, thus enabling the system to be used for either an anatomically correct shoulder prosthesis or alternatively a reverse shoulder configuration. In some embodiments, as shown in FIG. 12, and further detailed in FIG. 14, the metaphyseal shell is adapted with a substantially cylindrical recess to receive insertion of a mating structure on the prosthesis. So as to enable modularity, the implant surface comprises at least one possible engagement feature, and in some embodiments two or more different engagement features, each of which features is adapted for engagement with different engagement structures on matable cups and heads.

Figure 30:
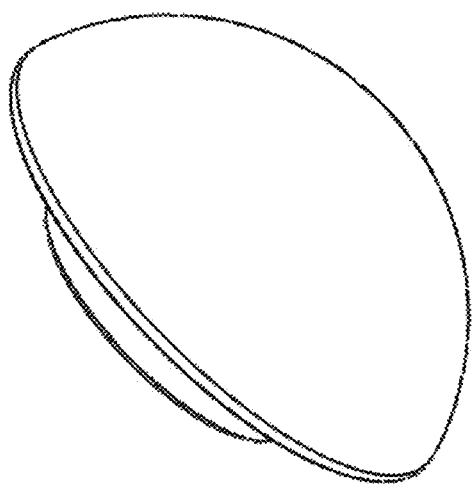
FIG. 30 shows a perspective view of an embodiment of a prosthesis articulation surface in the form of a spherical head, and a side view of an embodiment of a prosthesis articulation surface in the form of a spherical head, in cross section.
Figure 30:
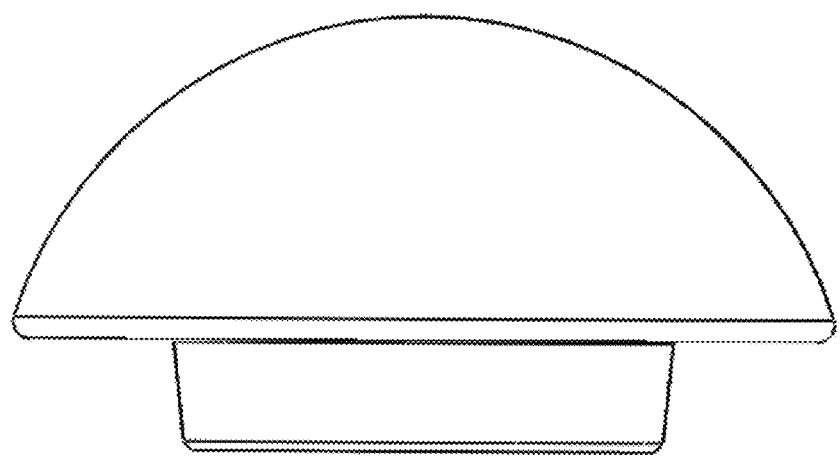
Figure 31:
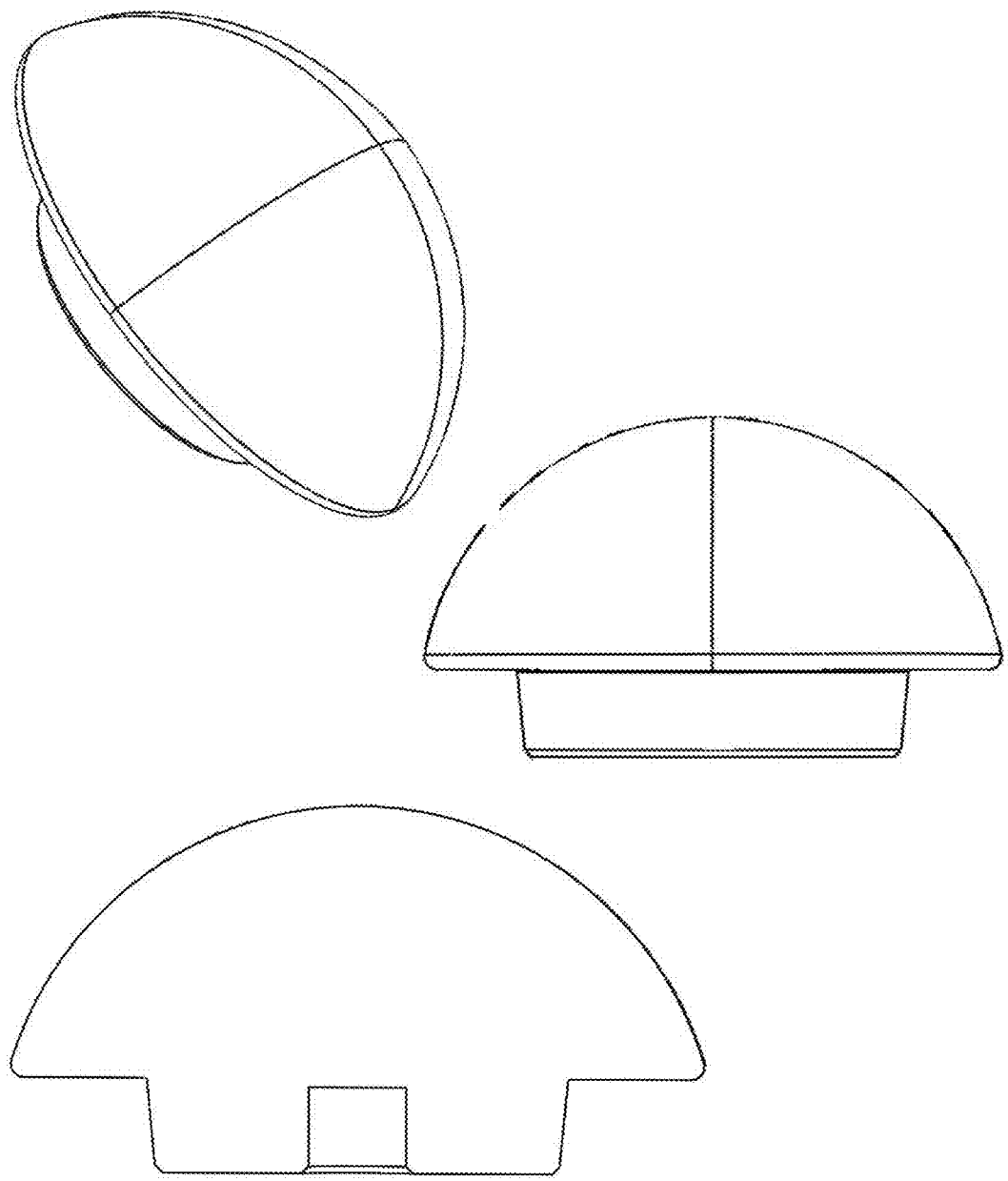
FIG. 31 shows a perspective view of an embodiment of a prosthesis articulation surface in the form of an elliptical head, a side view of an embodiment of a prosthesis articulation surface in the form of an elliptical head, and a side view in cross section.

As depicted, one engagement means is a taper, such as a Morse taper, adapted to mate with a corresponding structure on a prosthesis component, such as the tapers shown on representative prosthesis heads shown in FIG. 30 and FIG. 31. In accordance with the representative array of shells shown in FIG. 15, the dimensions of the engagement features, including the representative taper feature, may vary in length and diameter, and in general, the dimensions of these features can range from 5 mm to more than 100 mm. Thus, shells may be provided with engagement means, such as a taper, in heights and in greater and lesser diameters ranging in mm increments and fractions thereof from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to 100 mm.

Figure 39:
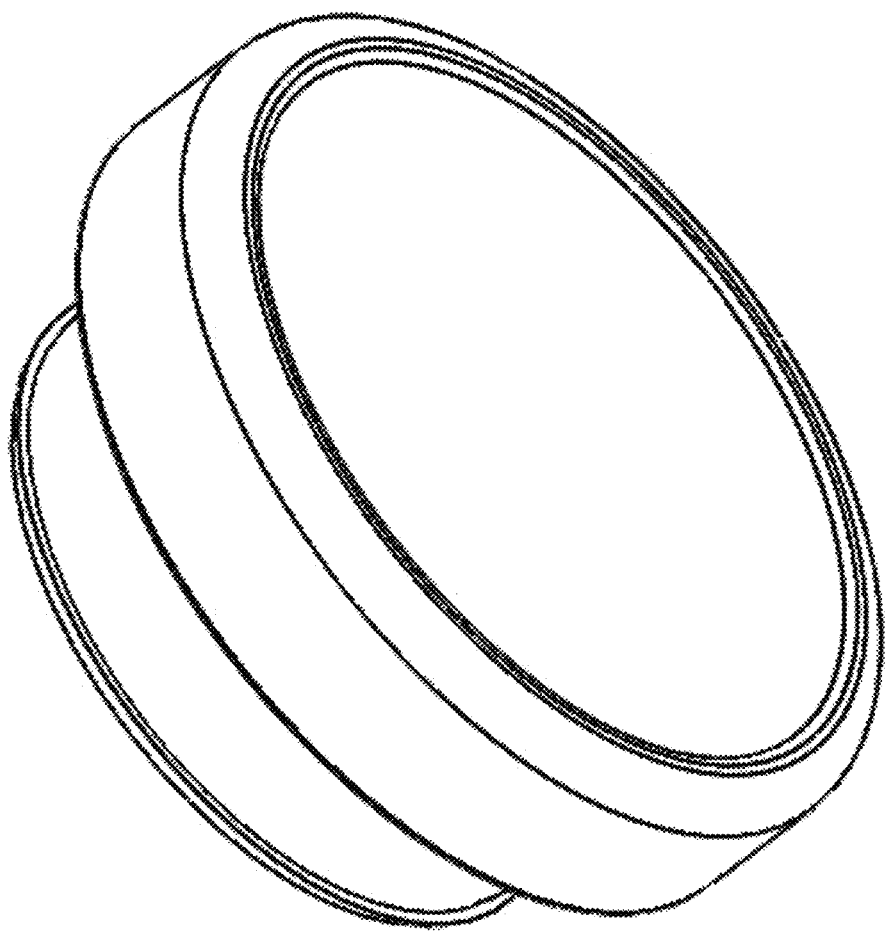
FIG. 39 shows a perspective view of an embodiment of a prosthesis articulation surface in the form of a concave poly cup.
Figure 40:
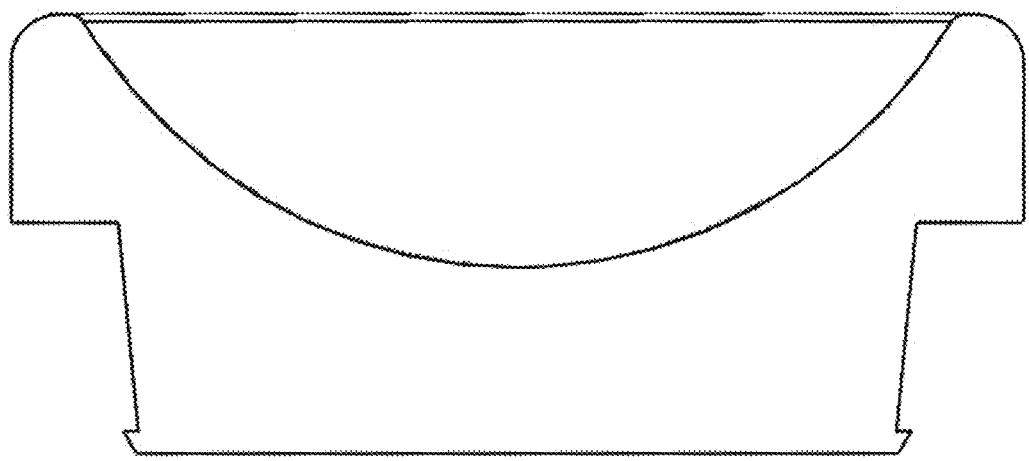
FIG. 40 is a side view of an embodiment of a prosthesis articulation surface in the form of a concave poly cup, in cross section.
Figure 41:
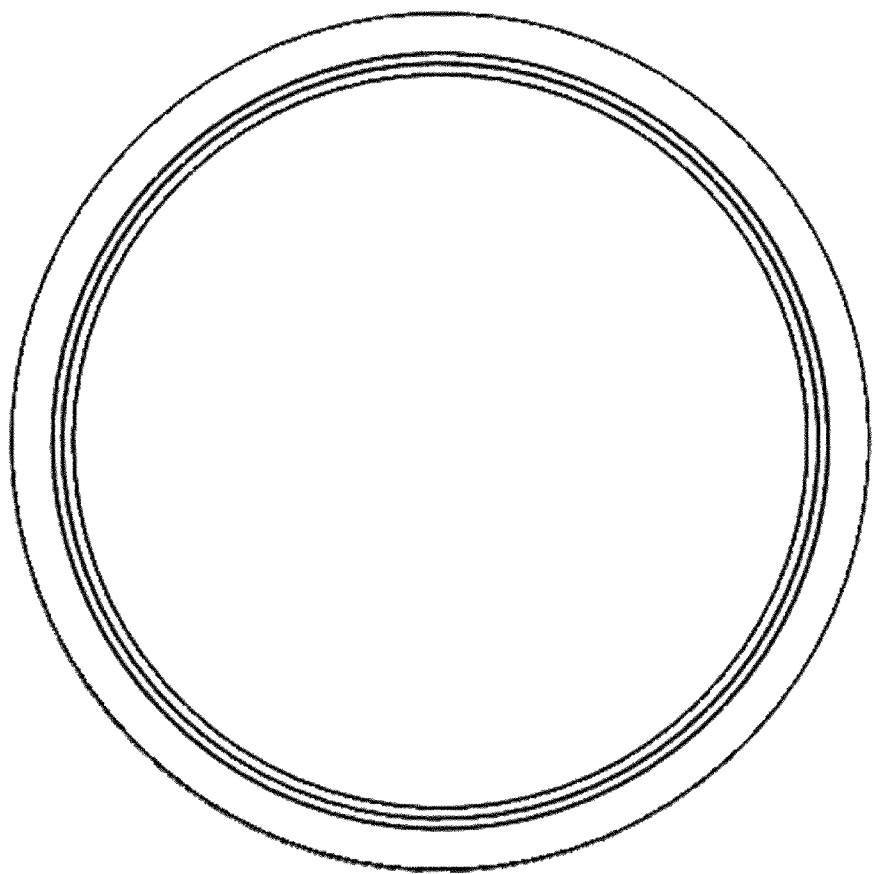
FIG. 41 is a top view of an embodiment of a prosthesis articulation surface in the form of a concave poly cup.
Figure 42:
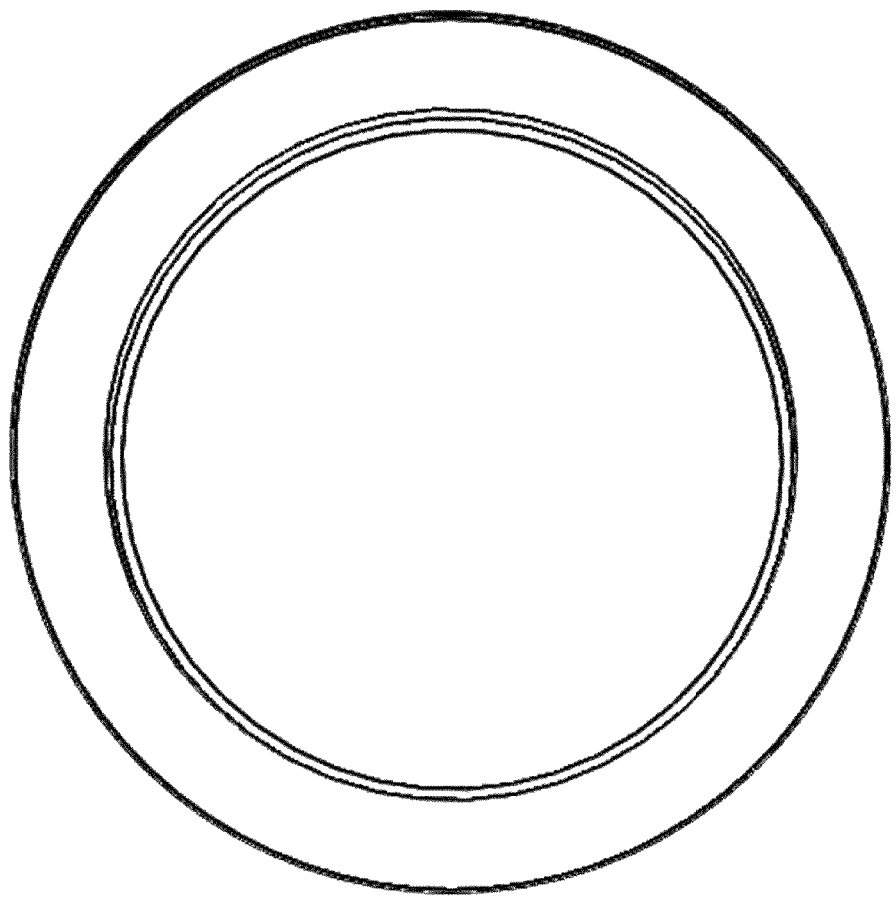
FIG. 42 is a bottom view of an embodiment of a prosthesis articulation surface in the form of a concave poly cup.
Figure 43:
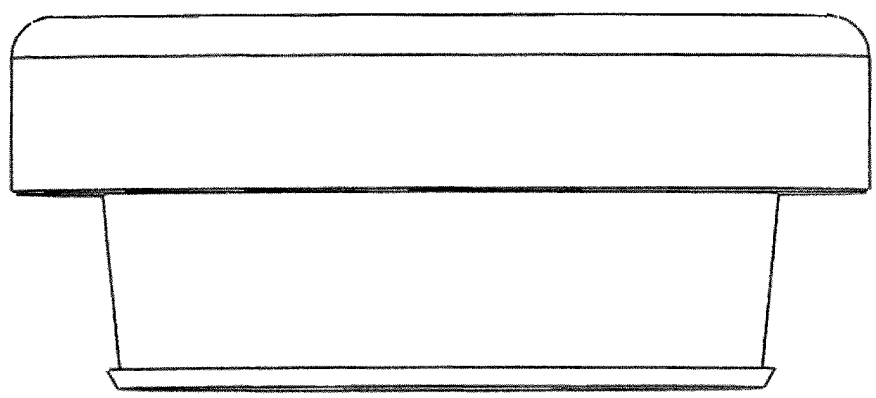
FIG. 43 is a side view of an embodiment of a prosthesis articulation surface in the form of a concave poly lock having a first embodiment of a metaphyseal shell lock feature.
Figure 43:
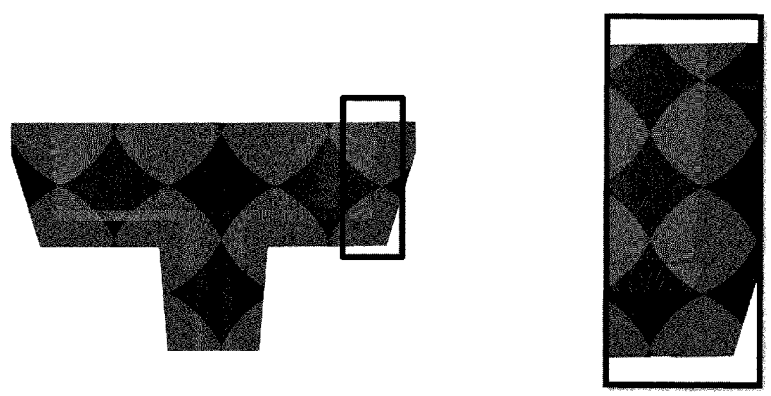
Figure 44:
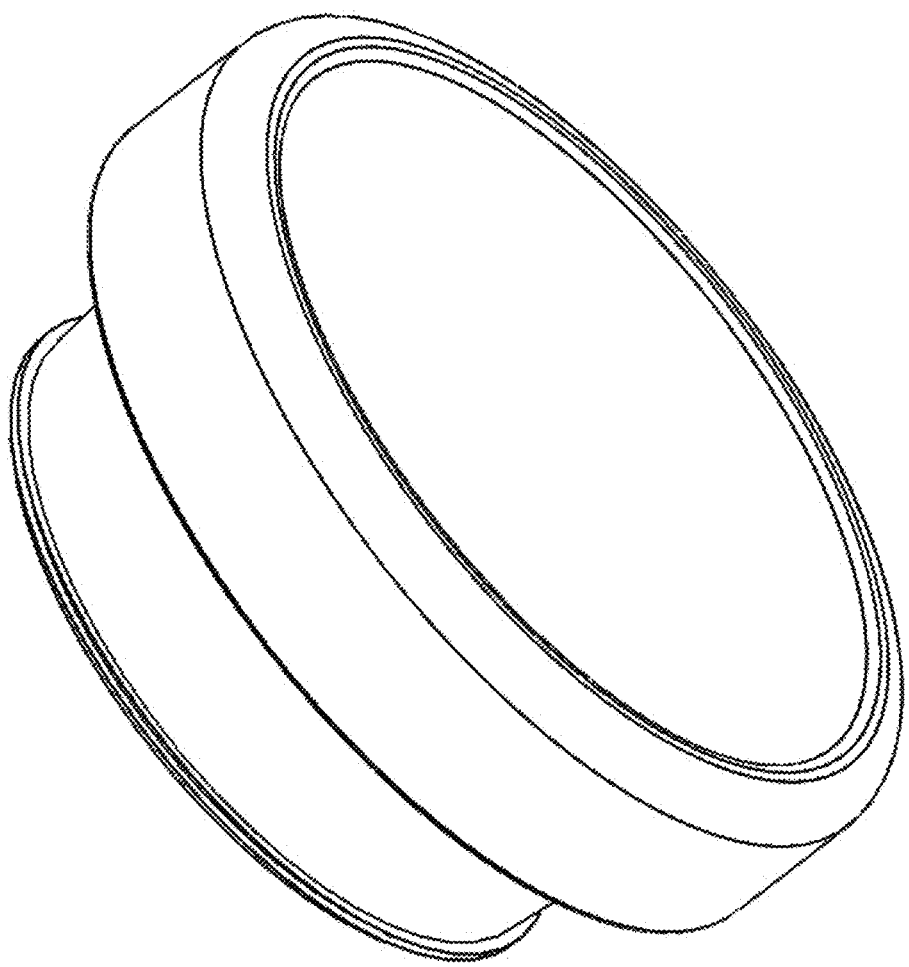
FIG. 44 is a perspective view of an alternate embodiment of a prosthesis articulation surface in the form of a concave poly cup.
Figure 45:
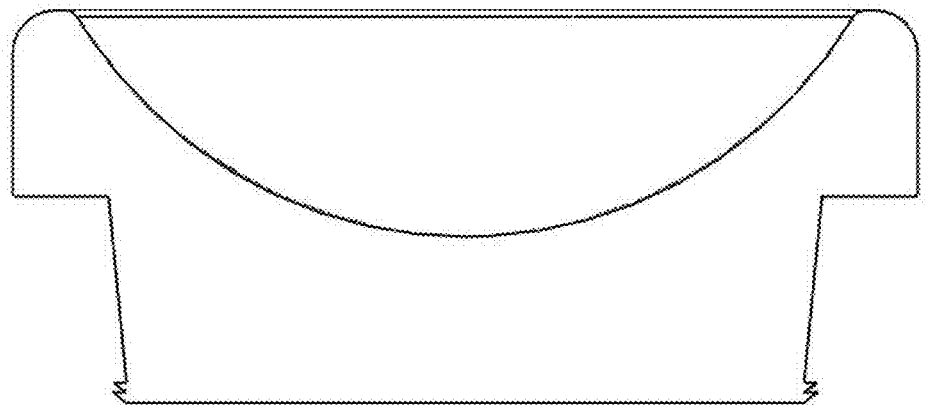
FIG. 45 is a side view of an alternate embodiment of a prosthesis articulation surface in the form of a concave poly cup, in cross section.
Figure 46:
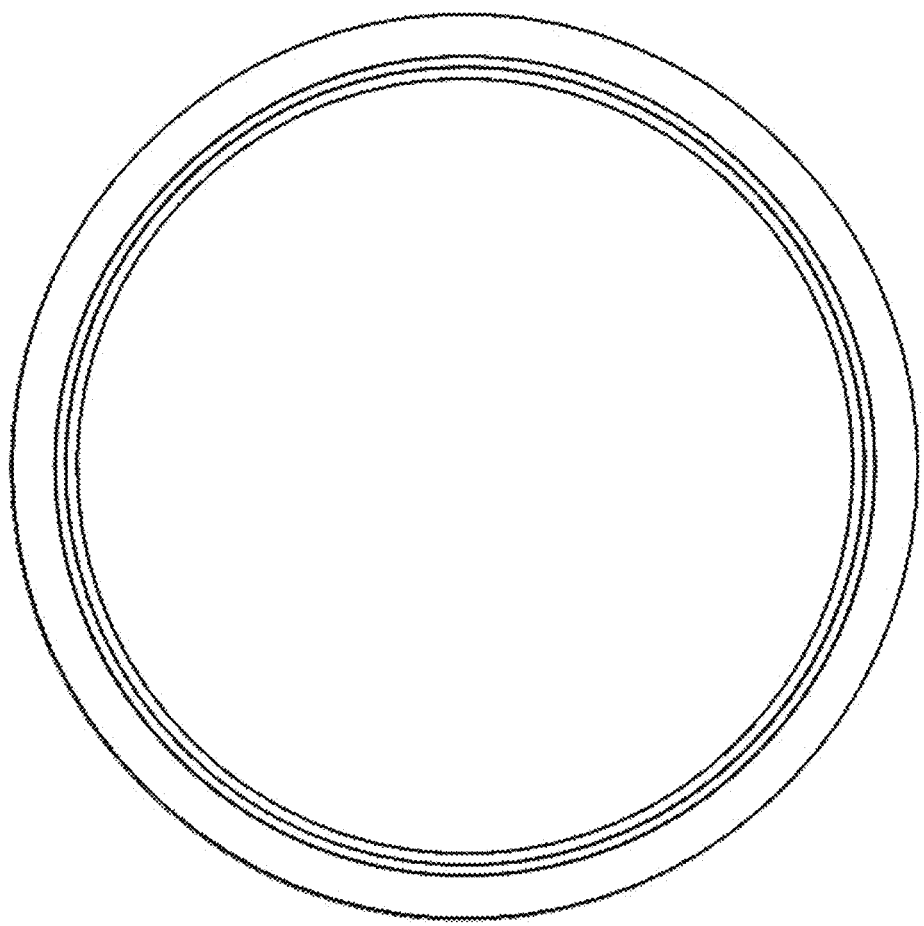
FIG. 46 is a top view of an alternate embodiment of a prosthesis articulation surface in the form of a concave poly cup.
Figure 47:
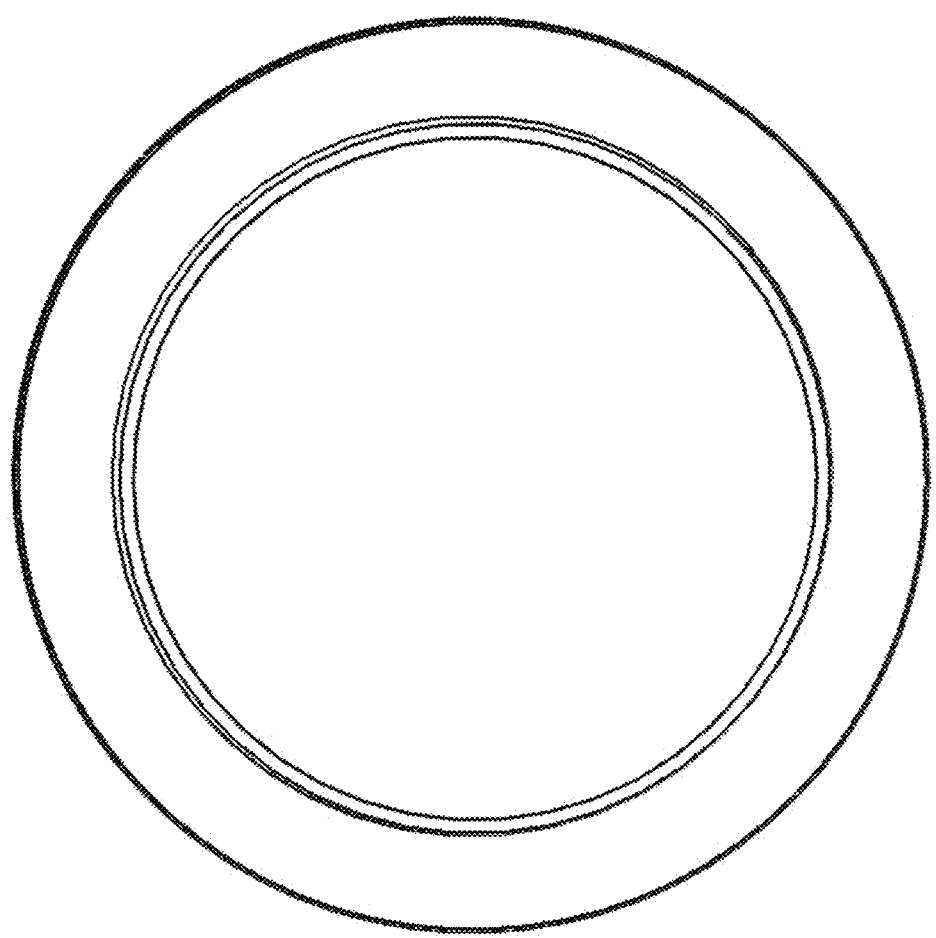
FIG. 47 is a bottom view of an alternate embodiment of a prosthesis articulation surface in the form of a concave poly cup.
Figure 48:
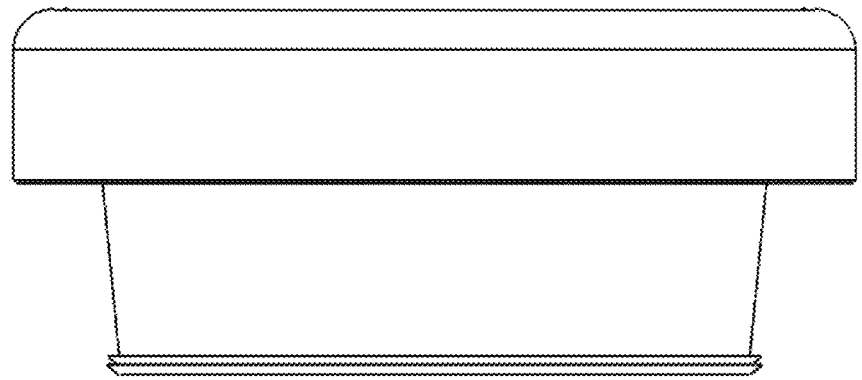
FIG. 48 is a side view of an embodiment of a prosthesis articulation surface in the form of a concave poly lock having an alternate embodiment of a metaphyseal shell lock feature.
Figure 48:
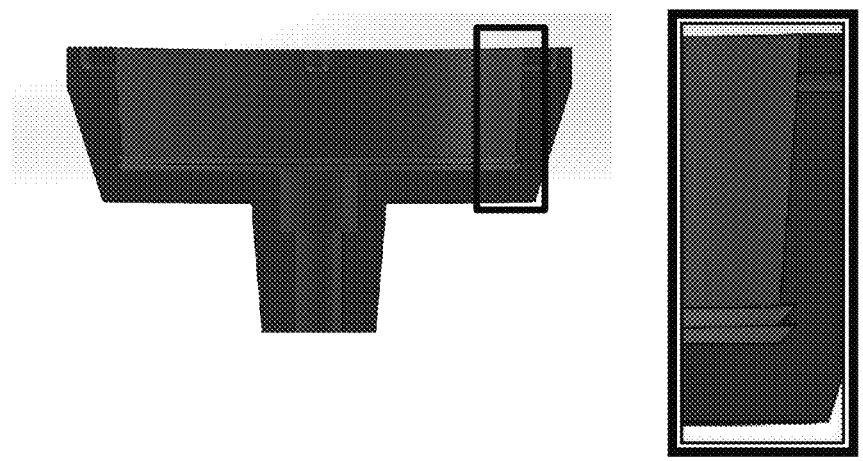

Another engagement means provided on a shell is circumferential tabs or teeth that enable a snap fit, such as for engagement with a cup as shown in FIG. 39 and FIG. 44. Such features may be present in singular or as a plurality, and may be positioned anywhere along the interior wall of the metaphyseal shell seat, including from the bottom to the top with any desired spacing there between and other optional interspersed surface features that may enhance fixation of a prosthesis component therein. Representative drawings that show detail of some embodiments of these engagement features are shown in FIG. 43 and FIG. 48, each of which drawings show side views of representative embodiments prosthesis components with engagement means in the form of concentric teeth positioned at the base of a taper on each of the alternate cup shaped implants. In some embodiments, the tabs or teeth may be notched to engage with corresponding splines or ribs to enable alignment and prevent axial displacement. Other means known in the art may be employed for engagement between the metaphyseal shell and prosthesis. In accordance with the representative array, the dimensions of the engagement features, including the representative tab features shown in the drawings, may vary in height and depth and spacing, and in general, the dimensions of these features can range from 0.1 mm to more than 20 mm. Thus, shells may be provided with the depicted engagement means, in mm increments and fractions thereof from 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, and 20 mm. Referring to the drawings, FIG. 12 and FIG. 13 each show alternate views of metaphyseal shells adapted with different engagement means which in the depicted embodiments are positioned at the base of the recess in the shells adjacent to the interior sidewalls thereof. It will be appreciated that the various engagement means are not intended to be limiting, and other engagement means that are not shown may be used, moreover, the engagement means may be used in the context of any form of prosthetic component, and may be used interchangeably between them.

In some embodiments, the shells include on their prosthesis surfaces other features that aid in placement and in removal. For example, one or more slots or other access portals may be provided on a shell or plug component to enable passage of an osteotome or other device to facilitate freeing an implant from bone due to boney ingrowth thereupon. In addition, one or more circumferential tool engagement features such as are shown on the upper periphery of the interior wall of the metaphyseal shell embodiments shown in FIG. 12, FIG. 13 and FIG. 14, may be provided to aid in the placement and press-fit fixation of the shell into bone, and subsequent adjustment or removal thereof in the event of a revision surgery.

Figure 50:
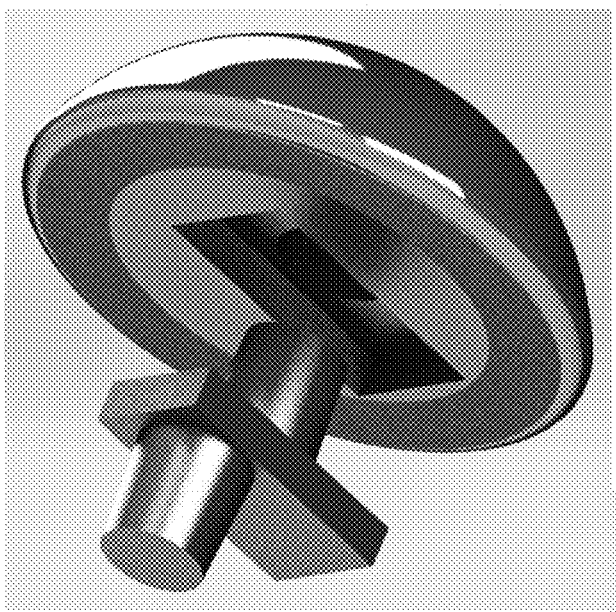
FIG. 50 is an perspective view of an alternate embodiment of a modular arthroplasty assembly showing a spherical head and an offset coupler for engagement with one or more of a stem and a metaphyseal shell and a short stem.
Figure 50:
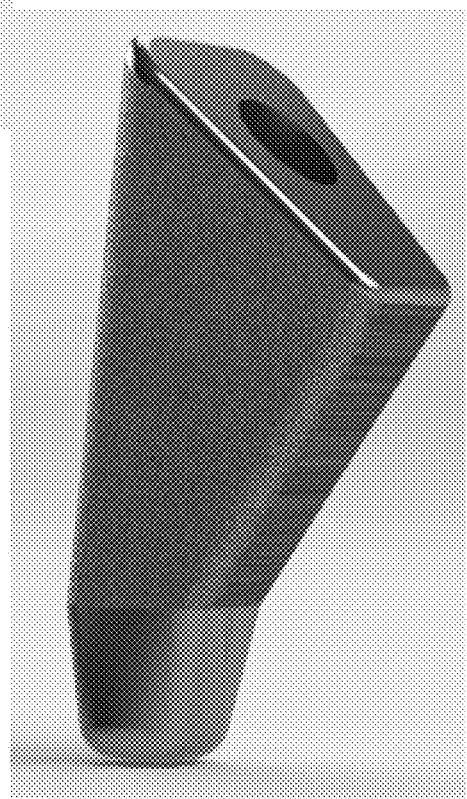
Figure 51:
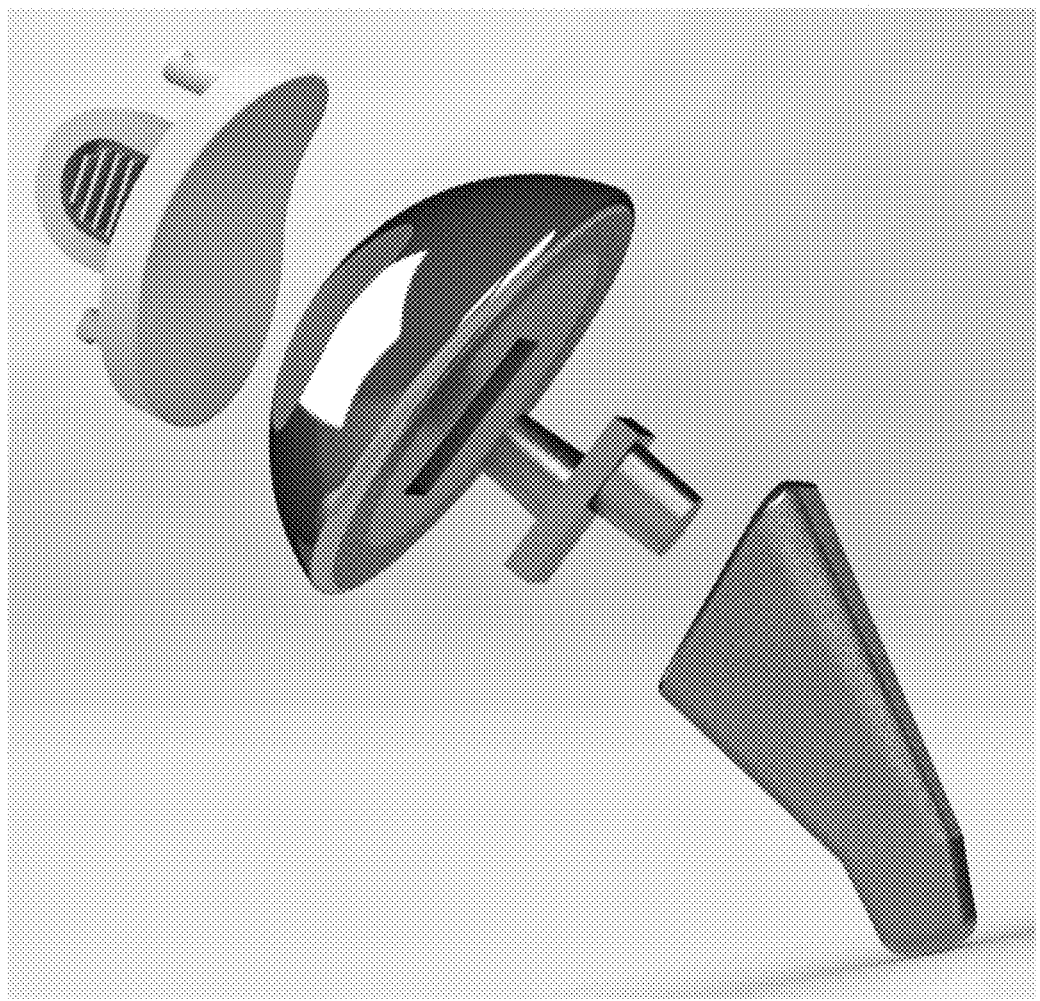
FIG. 51 is an exploded perspective view of an alternate embodiment of a modular arthroplasty assembly with a glenoid, spherical head, offset coupler and stem.

Referring now to FIG. 50, and FIG. 51, in some embodiments, a modular adapter referred to herein as an offset adapter may be provided that operates to mate the metaphyseal shell component with the humeral stem component (specific engagement with the metaphyseal stem not shown). An adapter may be in lieu of corresponding engagement elements on each of the metaphyseal shell and stem, or in addition to these. The modularity of the adapter enables further selection from a wide array of possible combinations of stem and metaphyseal shell positioning. In some embodiments, the shape of the adapter is configured for precise engagement with the stem and metaphyseal shell components.

In some examples, one or both of the metaphyseal shell and stem may be adapted with a female receiver comprising a cylindrical recess and a shallower overlaid recess that is polyhedral in shape. In some embodiments, the overlaid recess is substantially rectangular. In some embodiments, the modular adapter component comprises a polyhedral insert body having opposing faces, wherein each face has a male insert that is substantially cylindrical or peg shaped. In such embodiments, the opposing male inserts are each adapted to be press-fitted into the female receivers respectively positioned in the metaphyseal shell component and the humeral stem component, and the polyhedral insert body is received into the metaphyseal shell component. The modularity is achieved by varying the relative position of the opposing male inserts.

Accordingly, in various embodiments, an array of adapter components may be provided wherein the male inserts are varied on position along the opposing faces of the adapter such that they may be positioned at opposite ends, directly opposed from one another on the same end of the polyhedron or in the center, or at any other location along the opposing faces. In this manner, a wide array of options is available to allow selection of optimal positioning of the metaphyseal shell component relative to the position of the humeral stem. In various embodiments, the male inserts may further be varied in length, diameter, and angulation relative to the face of the adapter. Accordingly, in various embodiments, the modular adapter may have opposing male inserts that vary from one another in one or more of shape, angulation relative to the adapter face, length and diameter.

It will be appreciated that the metaphyseal shell is in some embodiments adapted for use above the bone cut line, partially below the bone cut line, or as more particularly described and shown herein, countersunk essentially completely below the bone cut line. The advantages of the metaphyseal shell as described herein can be realized in any implant configuration whether above, or partially or fully recessed below the bone cut line, particularly to enable customized selection and fit of implant components without being constrained by inventory limitations or by less than desirable implant height, neck angle, version, and posterior and medial offset.

Humeral Stem Component

Referring again to the drawings, FIG. 16-FIG. 29 show a variety of views of representative bone anchors in the form of diaphyseal stems in accordance with the disclosure. In various embodiments, the depicted shoulder prosthesis humeral stems are adapted for engagement with an metaphyseal shell, and optionally with a complimentary intermediate modular adapter component as described above. The humeral stem component may be used with the various modular adapter components described herein in the manner described above to configure humeral stem with broad flexibility for relative positioning of the metaphyseal shell and prosthesis component relative to the stem.

Figure 16:
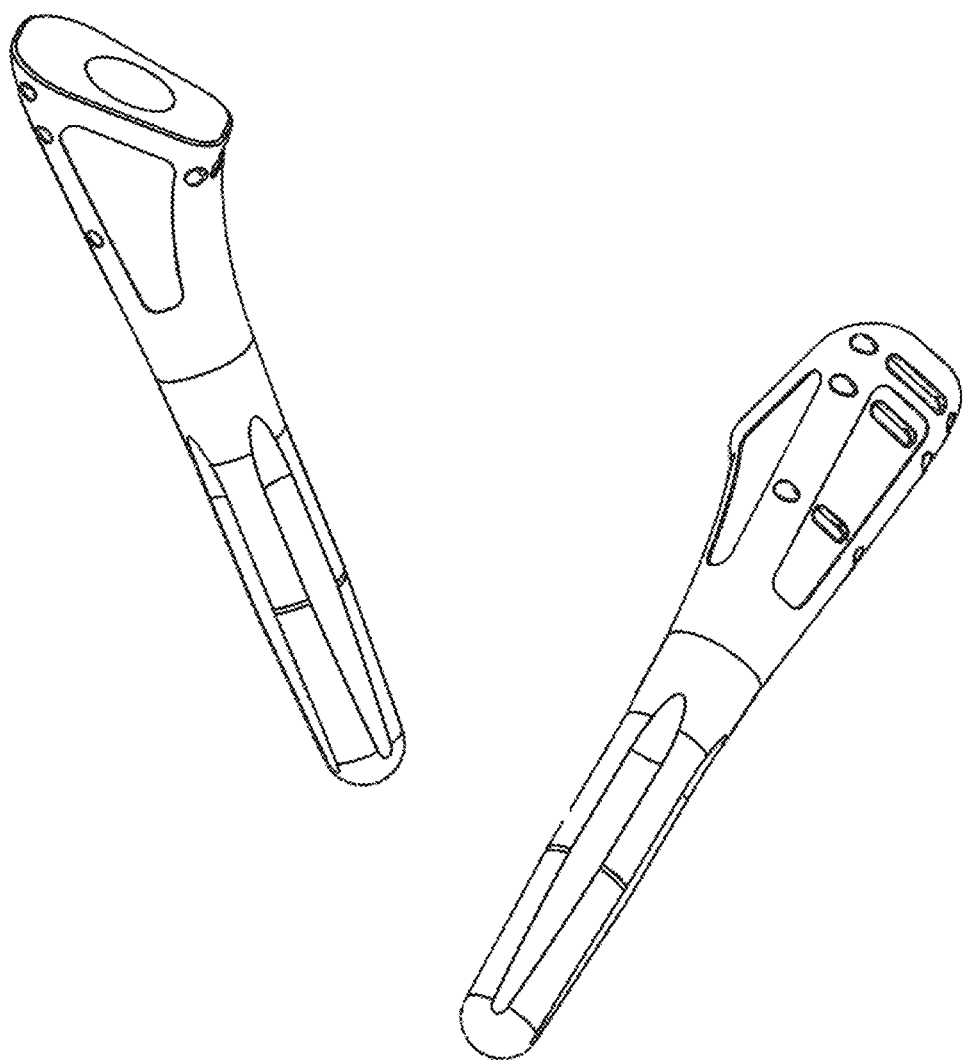
FIG. 16 shows alternate perspective views of an embodiment of a diaphyseal stem.
Figure 19:
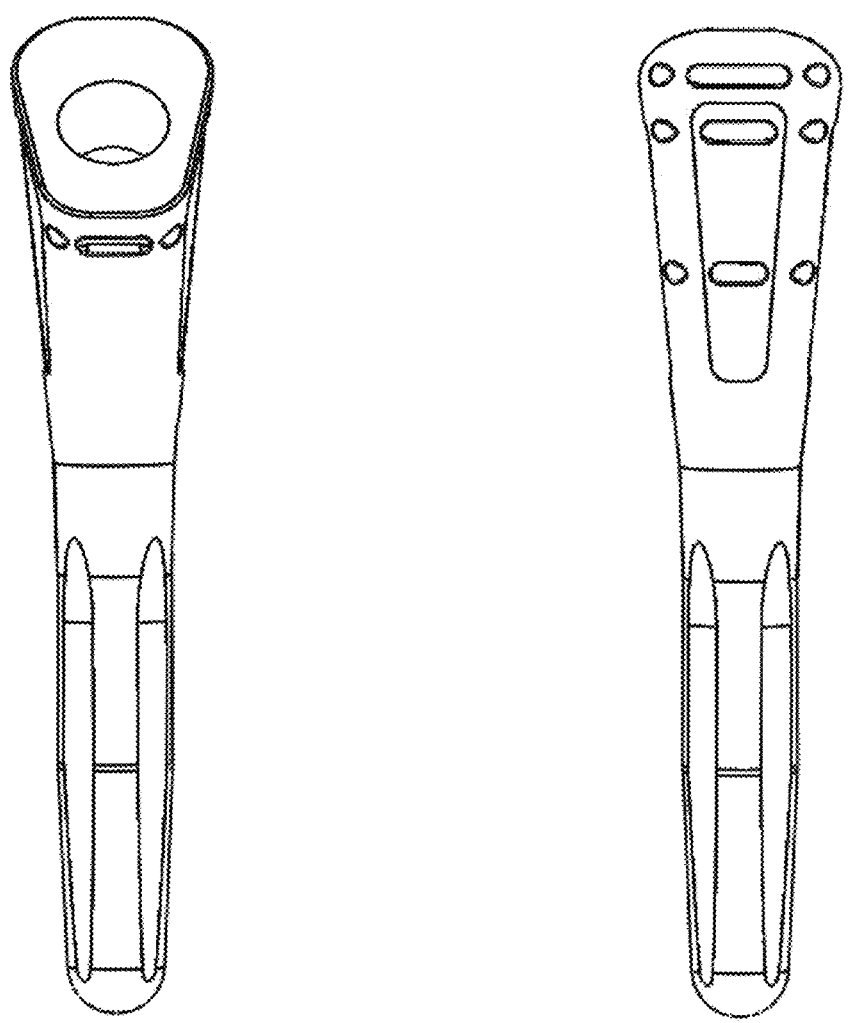
FIG. 19 shows a front view of an embodiment of a diaphyseal stem, and a back view of an embodiment of a diaphyseal stem.
Figure 20:
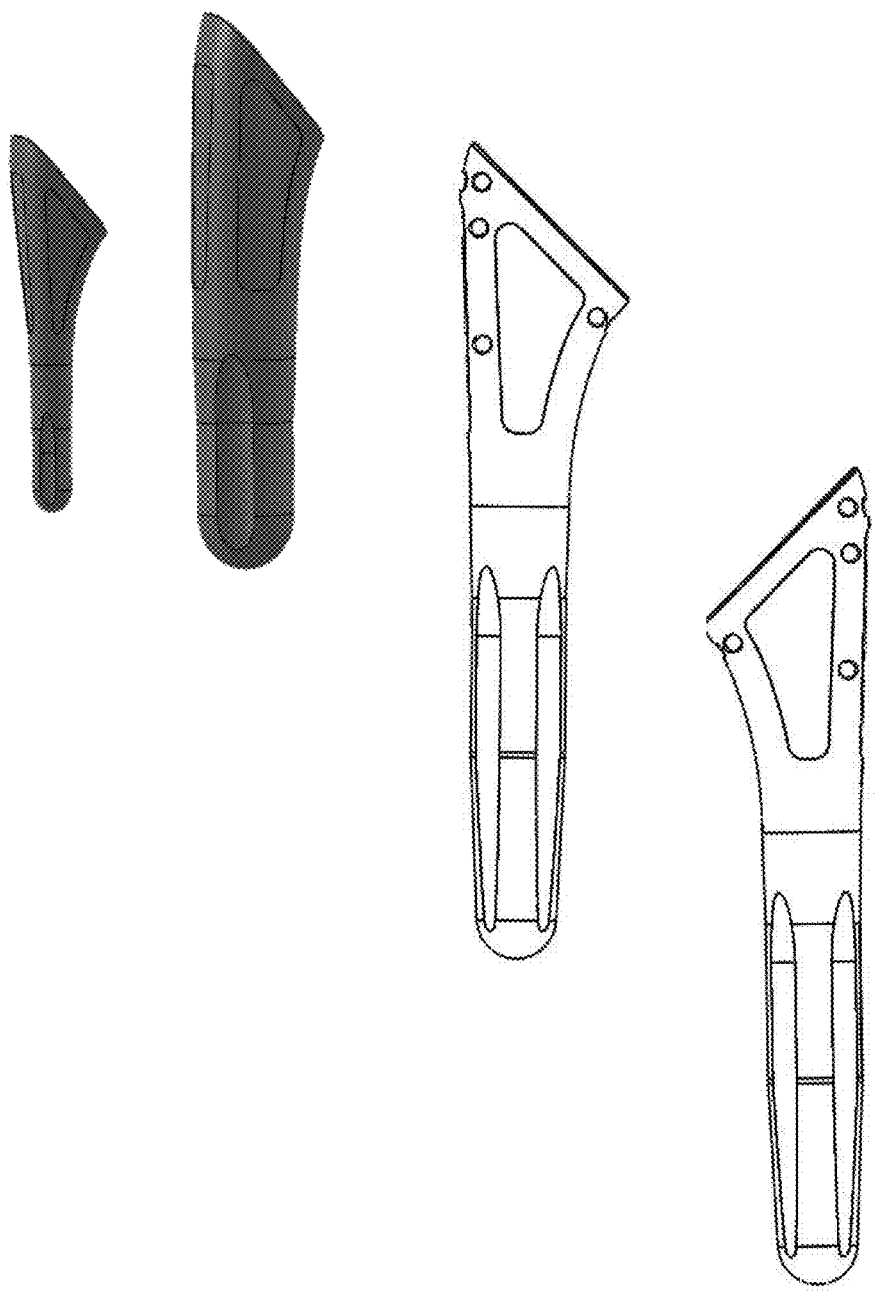
FIG. 20 shows a side views of an embodiment of a diaphyseal stem in different sizes in solid form, and alternate side views of an embodiment of a diaphyseal stem.

Referring now to FIG. 16 which shows perspective views of an embodiment of a diaphyseal stem, the stem is comprised of a proximal region (about the upper ⅓ of the stem) that is adapted for alignment with the bone cut in the metaphysis and engagement to the shell, and a distal region (about the lower ⅔ of the stem) which is fit into the distal region of the diaphysis. The proximal and distal ends are delineated in the representative drawings by a circumferential line positioned just above the elongate distal flutes, as seen in FIG. 19, for example. Alternate front, back, side bottom (plan view from the distal end) and top (plan view from the proximal end) are shown in FIG. 16-FIG. 20. In various embodiments, the shape of one or both the proximal and distal ends of the stem are adapted to be press-fit within the bone. In certain exemplary embodiments, the proximal portion of the stem is selected to be a best fit for tight press-fit within the upper diaphysis/metaphysis of the bone.

In various embodiments, the humeral stem includes an engagement feature, which is shown in representative FIG. 19 as a female taper receiver on its proximal end that is adapted to receive a male insert, such as a tapered extension, to achieve engagement with the metaphyseal shell. In some embodiments, the size, shape, location/position of the receiver and combinations of these features may vary to allow adaptability to the relative positioning of the engaged stem and metaphyseal shell.

Figure 23:
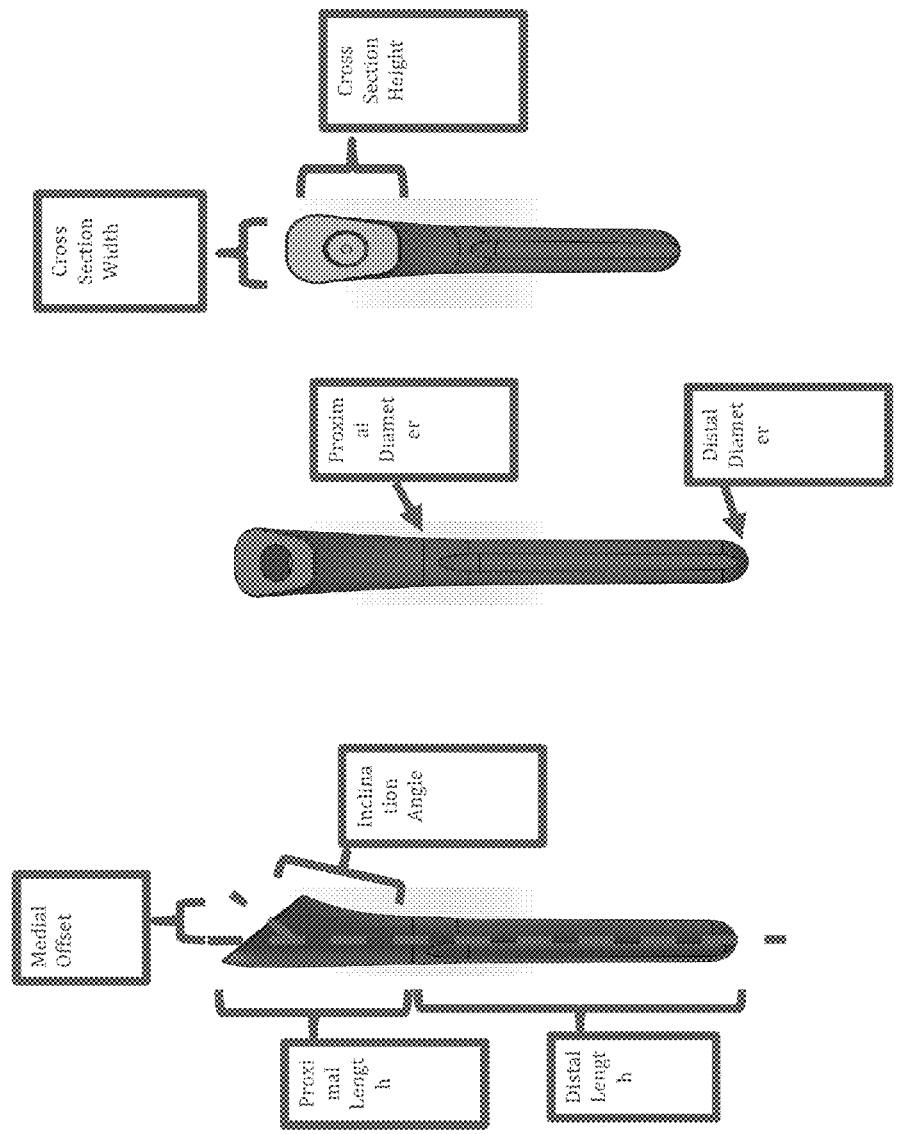
FIG. 23 shows alternate side, front and front cross-sectional views of a representative embodiment of a diaphyseal stem.

FIG. 23 shows alternate side, front and front cross-sectional views of a representative embodiment of a diaphyseal stem. Overall, the cross sectional shape of the stem at its proximal end is generally trapezoidal and is adapted for achieving a desirable degree of fill of the upper end of the diaphysis and the metaphysis. In various embodiments, based on the size of the stem, the degree of fill to be achieved with a stem ranges from 20 to 60%, and in some desirable embodiments about 40%. Thus, the extent of fill ranges from and includes as a percentage of the void space in the engagement area of the bone, about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, to 60. Overall, the cross sectional shape of the stem at its distal end is generally circular and may be adapted with fluting or other features to facilitate engagement of instruments for ease of removal as needed.

Figure 27:
FIG. 27 shows alternate side and perspective views of the shell engagement end (proximal end) and a bottom (distal end) view of a representative embodiment of a stem.

In some embodiments, the stem component is adapted to enhance bony ingrowth and bone strength at regions of the humeral bone, for example at the proximal end only of the stem. As shown in the drawings, for example, FIG. 20, which shows a side view of an embodiment of a diaphyseal stem, in solid form, features on the proximal and distal end may be included in some embodiments to facilitate fixation in the bone and facilitate subsequent removal, as in the instance of revision surgery. Again with reference to FIG. 20, according to some embodiments, the surface of the stem is configured with features and surface texturing to encourage bone growth along the proximal end of the stem, and the tapered distal end is devoid of texturing to discourage bone ingrowth and to enable easy disengagement of the stem from the distal diaphyseal portion in the event removal is necessary. In some embodiments, the entire lateral surface of the proximal end is textured to encourage bone ingrowth. In alternate embodiments, such as shown in FIG. 16 and FIG. 27, for example, the stem has flattened panels on its sides and the flat areas of the proximal end are textured for bony ingrowth while the remainder of the lateral portions of the proximal end are not textured. Referring again to the drawings, FIG. 27 shows alternate side and perspective views of the shell engagement end (proximal end) and a bottom (distal end) view of a representative embodiment of a stem. As shown, in some embodiments, the proximal end includes one or more suture holes.

Figure 21:
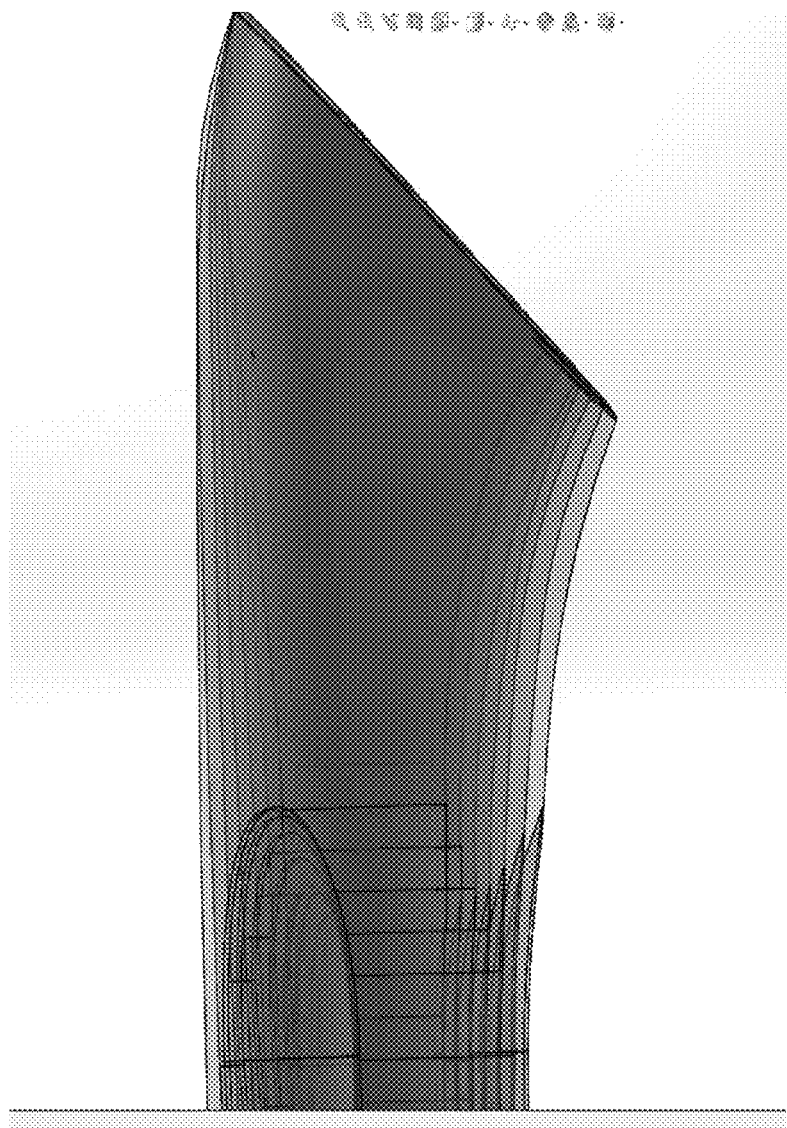
FIG. 21 shows a side view of an overlay of an array of sizes of a representative embodiment of a diaphyseal stem showing the variation in contour at the proximal end as a function of size.
Figure 22:
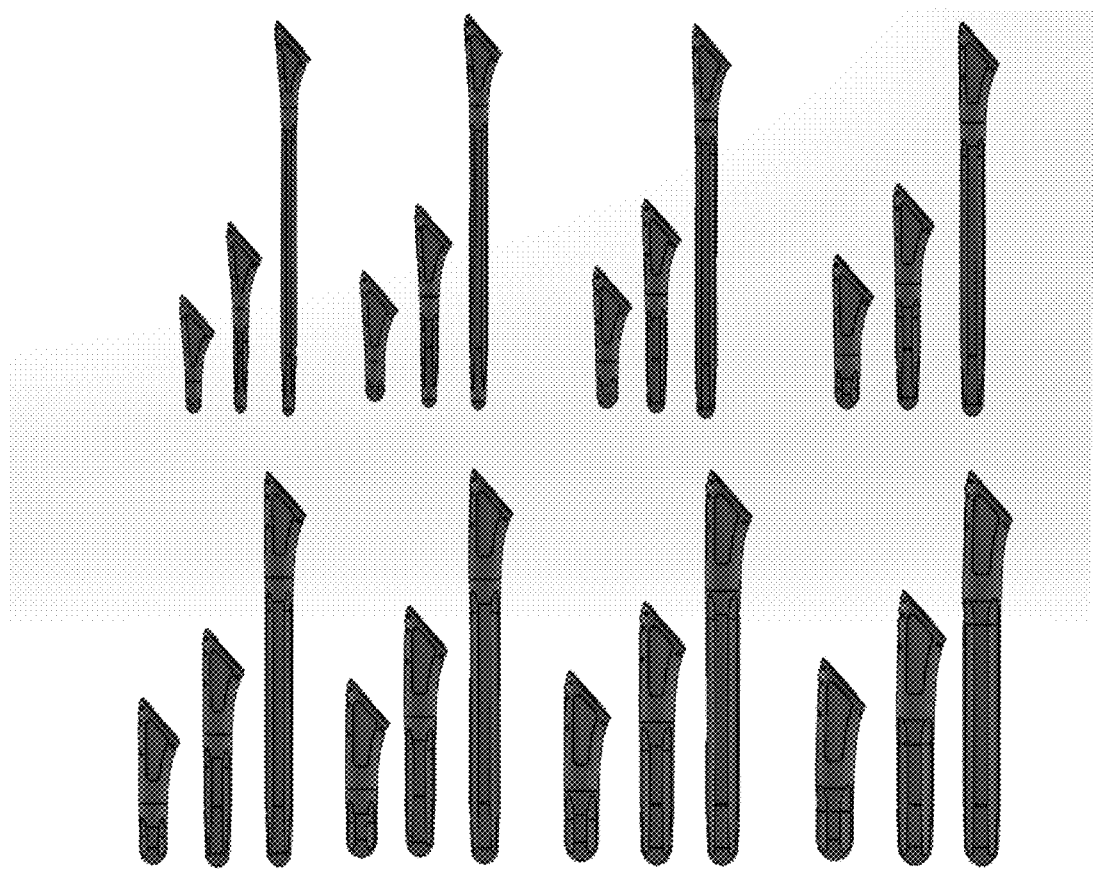
FIG. 22 shows a side view of an array of sizes of a representative embodiment of a diaphyseal stem.

The length of the stem may be varied and its proximal and distal dimensions and features may likewise be varied in accordance with those known in the art. FIG. 21 and FIG. 22 each show alternate depictions of a size array of stems. FIG. 22 shows a side view of an array of sizes of a representative embodiment of a diaphyseal stem. The array represents a possible set of stems that are provided in three lengths (short, standard and long) and varied sizes (in the depicted set, there are 8 sizes) of proximal and distal features within the each length. FIG. 21 shows a side view of an overlay of an array of sizes of a representative embodiment of a diaphyseal stem at a particular length (short) showing the variation in contour at the proximal end as a function of size. In the depicted embodiment of stem array, the girth of each stem size grows proportionally as the size increases, and the proximal and distal sections grow incrementally with size, with the distal length increasing at a greater rate relative to the proximal length. It will be apparent to one of ordinary skill that varying shapes and sizes of stems are possible and generally within the skill in the art. In the context of the stems disclosed herein, the relative girth of the proximal end is selected to achieve the closest possible press fit within the bone to enhance stabilization, to provide maximal proximal surface contact to support the metaphyseal shell and to accommodate the fixation engagement between the shell and the stem. Thus, variations in stem features are possible with respect to sizing, and the size without departing from the scope of the disclosure and the claims.

As shown in FIG. 22, the representative array includes the following possible set of stems: short stems that vary in length ranging from about 70 mm to 98 mm; standard stems that have a length of about 125 mm; and long stems that have a length of about 175 mm; Within each of these lengths, the stems further vary in size, with 8 representative sizes. In accordance with the foregoing, in various embodiments, the stems may have length dimensions as follows: The stems may vary in size from small at a length of from 45 to 110 mm, and more particularly from about 60 to 95 mm, and more particularly from about 60 to 95 mm; to a medium length from about 110 to 130 mm, and more particularly from about 125 mm; to a long stem length from about 130 mm to about 180 mm, and more particularly from about 175 mm. Of course, multiple intermediate size increments are possible, thus stems may vary in length in mm and increments in between from about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, to 180.

In various embodiments, the stems may have proximal length dimensions as follows: The proximal portions of the stems may vary in size from 35 to 60 mm, and more particularly from about 40 to 54 mm. Of course, multiple intermediate size increments are possible, thus the proximal ends of the stems may vary in length in mm and increments in between from about 35, 36, 37, 38, 39, 40, 41, 42, 43, 44, 45, 46, 47, 48, 49, 50, 51, 52, 53, 54, 55, 56, 57, 58, 59, to 60.

In various embodiments, the stems may have distal length dimensions as follows: The distal portions of the stems may vary in size small distal length of from 25 to 50 mm, and more particularly from about 30 to 44 mm; to a medium distal length from about 70 to 90 mm, and more particularly from about 71 mm to about 85 mm; to a long distal stem length from about 120 mm to about 140 mm, and more particularly from about 121 mm to 135 mm. Of course, multiple intermediate size increments are possible, thus the proximal ends of the stems may vary in length in mm and increments in between from about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134 to 135.

The stems are provided to be suitable for placement within bone and engaged with a shell wherein the bone cut is at an angle of inclination from and including angle increments in between 120, 121, 122, 123, 124, 125, 126, 127, 128, 129, 130, 131, 132, 133, 134, 135, 136, 137, 138, 139, 140, 141, 142, 143, 144, and 145. In accordance with the disclosure, in various embodiments, the stems have a shell-mating surface having an inclination that is about 135 degrees. It will be apparent to one of ordinary skill in the art that the stems could be provided having a different angle of inclination, and that the ultimate angle of inclination of an implant is determined based on the angle selected by the surgeon when making the bone cut.

In various embodiments, the stems may have a cross sectional shape that is generally cylindrical, trapezoidal, rectangular or other, and combinations of these between the proximal and the distal ends. And in various embodiments, the stems may have circumferential dimension features in mm and increments in between from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, to 200 or more.

Figure 24:
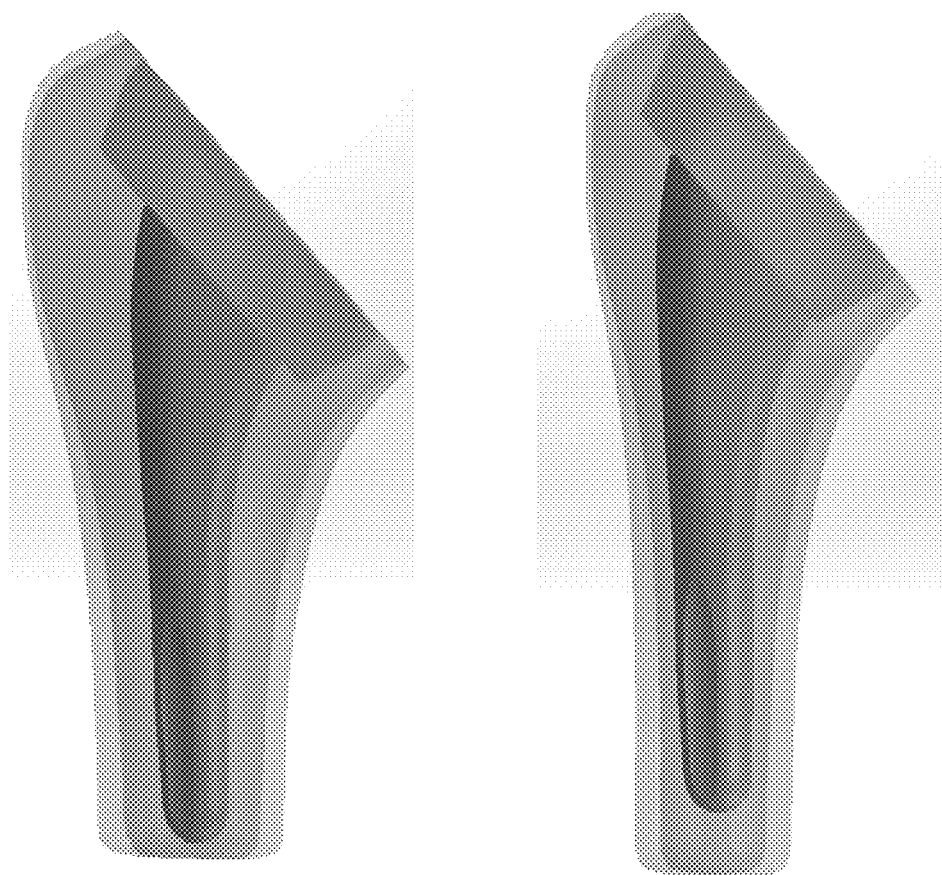
FIG. 24 shows a side view of an selection of sizes of a representative embodiment of a diaphyseal stem engaged with a metaphyseal shell, in the context of bone.
Figure 25:
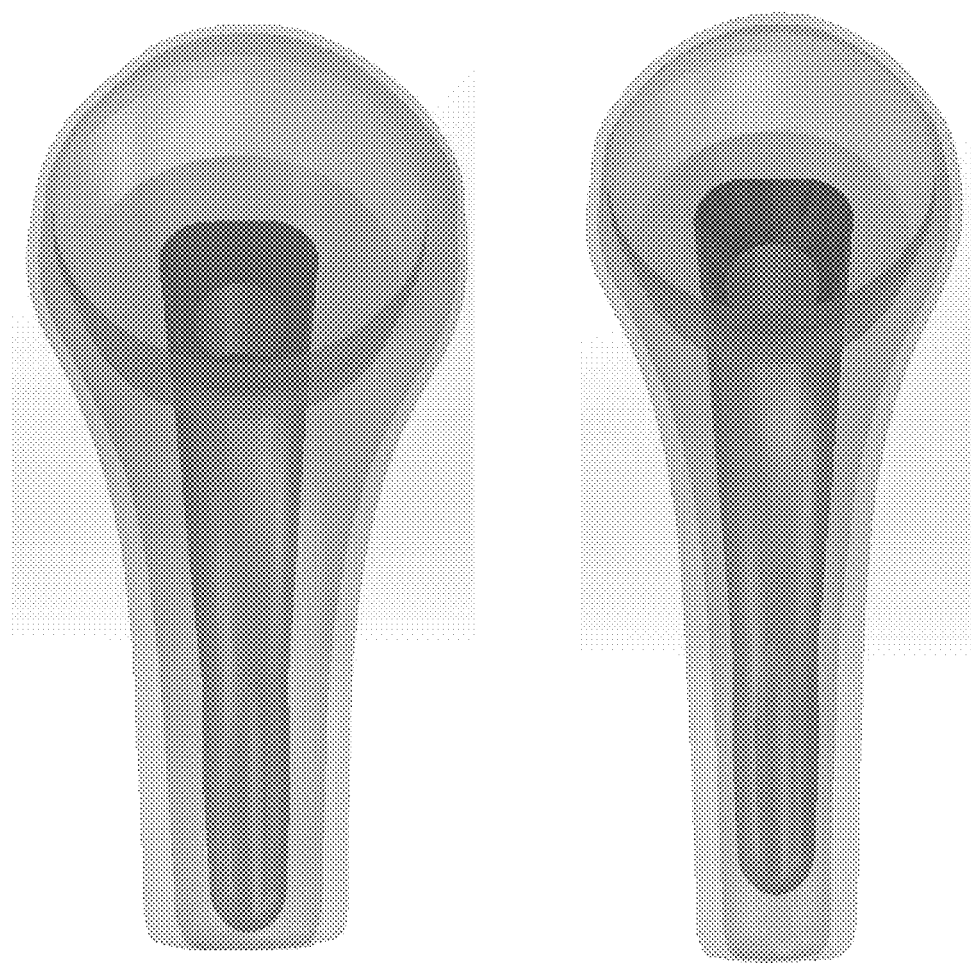
FIG. 25 shows a front view of an selection of sizes of a representative embodiment of a diaphyseal stem engaged with a metaphyseal shell, in the context of bone.
Figure 26:
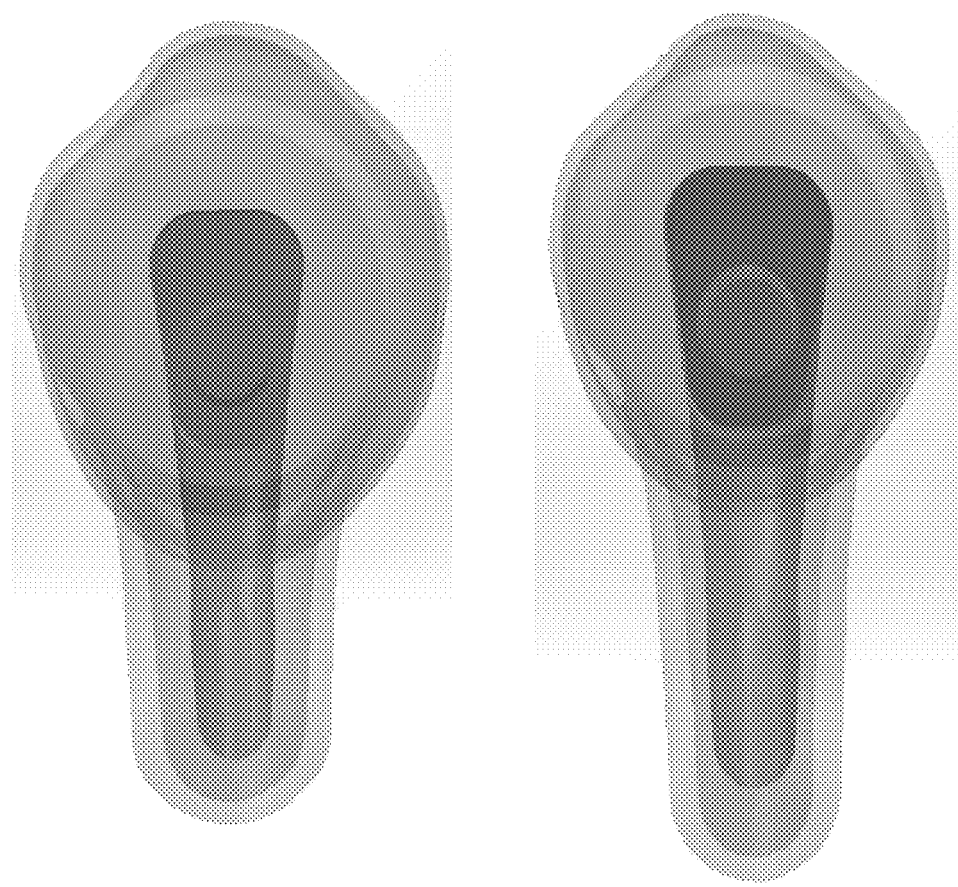
FIG. 26 shows a front cross-sectional view of an selection of sizes of a representative embodiment of a diaphyseal stem engaged with a metaphyseal shell, in the context of bone.
Figure 28:
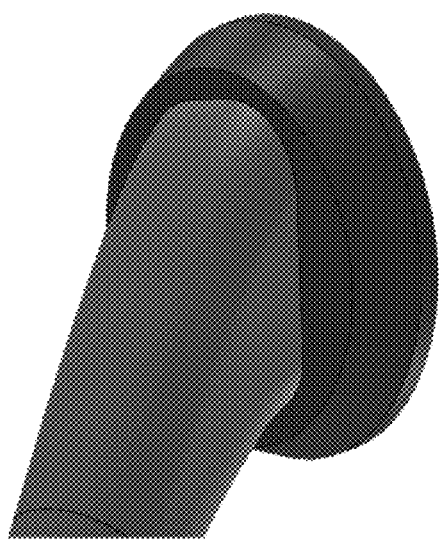
FIG. 28 shows a view of a selection of assembled representative embodiments of a metaphyseal shell and diaphyseal stem showing representative offsets to accommodate patient anatomy.
Figure 28:
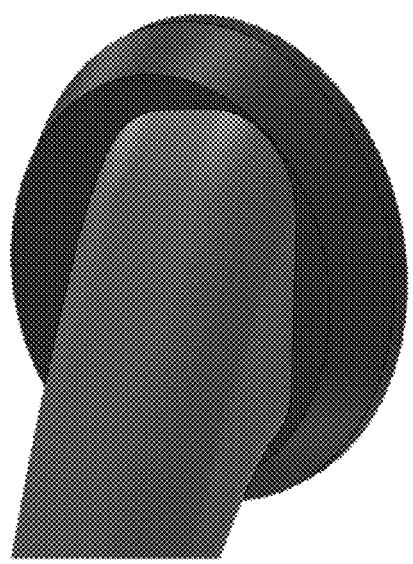
Figure 29:
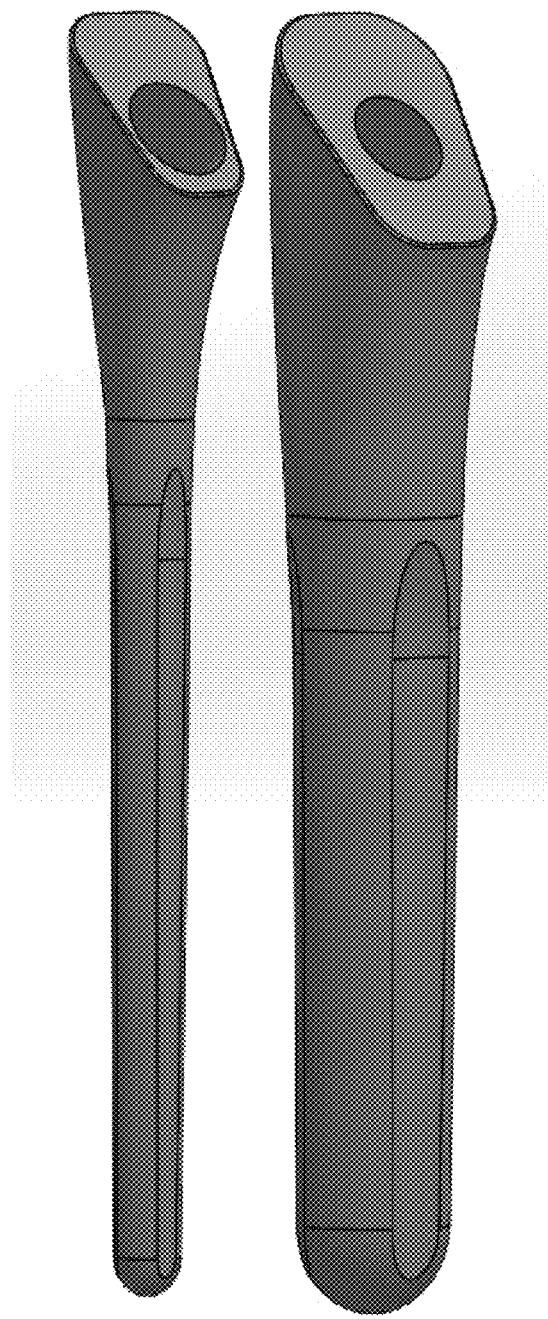
FIG. 29 shows a perspective view of two sizes of standard length diaphyseal stems showing representative relative positions of the engagement receiver (female taper) as the girth of the stem changes.

Referring again to the drawings, representative images are shown depicting stems and shells of the disclosure engaged and engaged in the context of bone. FIG. 24, FIG. 25 and FIG. 26 each show, respectively, side, front, and front cross-sectional views of an selection of sizes of a representative embodiment of a diaphyseal stem engaged with a metaphyseal shell, in the context of bone. These representations show the variation of diaphyseal and metaphyseal bone contact achieved through stem selection. FIG. 28 shows a view of a selection of assembled representative embodiments of a metaphyseal shell and diaphyseal stem showing representative offsets to accommodate patient anatomy. FIG. 29 shows a perspective view of two sizes of standard length diaphyseal stems showing representative relative positions of the engagement receiver (female taper) as the girth of the stem changes. As evident in the drawing, the placement of the engagement feature appears shifted (front to back) as the girth of the proximal metaphyseal engagement portion of the stem increases. This design ensures that the engagement feature of the shell with the stem is accommodated as the inner space of the bone is more constrained and the proximal end of the shell is more slender to fit the anatomy.

Referring again to the drawings, FIG. 17 shows alternate cross sectional views of the depicted stem, showing further detail of the engagement feature. As depicted, the feature is a female taper for receiving a corresponding taper on the shell, and is further adapted with a secondary fixation engagement feature in the form of a threaded bore. As described hereinabove, the engagement feature enables fixation between the stem and the shell and likewise allows disengagement in the event of device repositioning during primary surgery or removal and possible replacement in the event of a later revision. It will be appreciated, as mentioned herein above, that this exemplary secondary engagement feature is optional.

Figure 49:
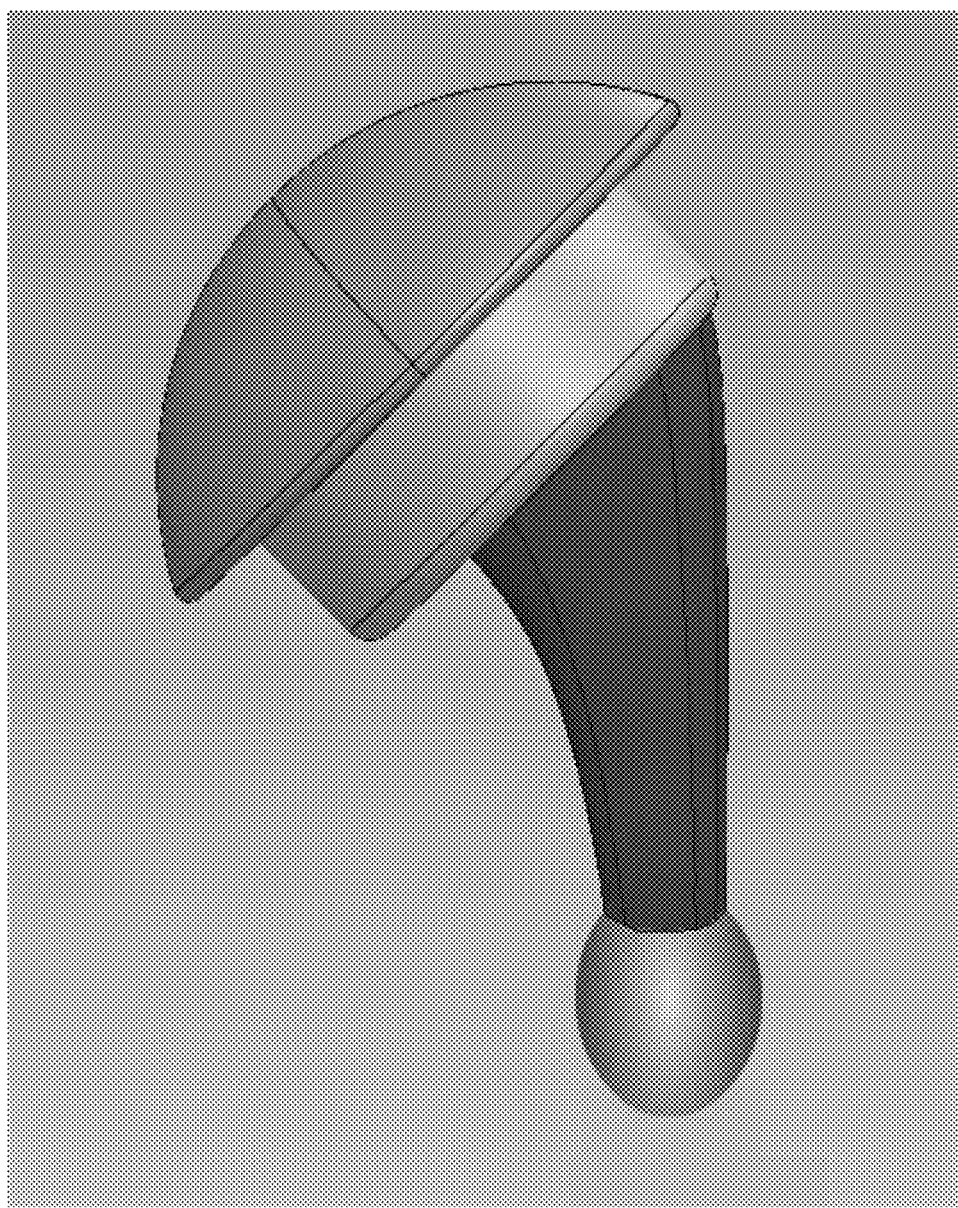
FIG. 49 is a side view of an alternate embodiment of a modular arthroplasty assembly with a short stem and a distal diaphyseal fixation feature.

Referring again to FIG. 49, an alternate embodiment of a possible stem is shown that includes an anchor in the form of a modular diaphyseal stabilizer that includes a stem. The depicted stem represents a short stem that has a shorter length and extends less into the distal portion of the diaphyseal canal than the stems shown in the drawings FIG. 16-FIG. 29, for example. As shown in FIG. 49, the stabilizer is generally elliptical or spherical in shape. In some embodiments, it may be integrated with the stem and in other embodiments it may be removable. The stabilizer may be selected from a range of stabilizers that may vary in one or more of shape, length, diameter, and material. In some embodiments, the stabilizer as well as the distal portion of the stem is devoid of surface texturing or other material properties that would encourage bony ingrowth, while the more proximal portion of the stem may be in some embodiments be provided with material features to encourage bony ingrowth. The adjustability of the stem length and distal shape and diameter achievable with the modular stem and stabilizer provides the ability to more closely customize the implant to a particular patient, taking into account that older populations of patients tend to have diminished diaphyseal cortical bone and thus a relatively larger diameter medullary canal as compared with other patients. The stabilizer is desirable to provide distal stability to the implant and prevent toggling at the proximal end, particularly at the time just after implantation before bony ingrowth at the proximal end occurs to enhance stability.

Prosthesis Component

In various embodiments, the modular arthroplasty assembly includes a prosthesis component. Examples of possible components, selected from exemplary humeral head, FIGS. 30-31 and FIG. 33-FIG. 38, and cupped reverse prosthesis components, FIG. 39-FIG. 48. The prosthesis is adapted on a first surface to provide a functional feature, such as a humeral head or a cupped reverse prosthesis function. On a second, generally opposing surface, the prosthesis comprises elements adapted for engagement with the metaphyseal shell. In some embodiments, the engagement is non-permanent such that the prosthesis component can be disengaged from the metaphyseal shell through use of a tool adapted to achieve displacement.

Humeral Head Prosthesis

Figure 62:
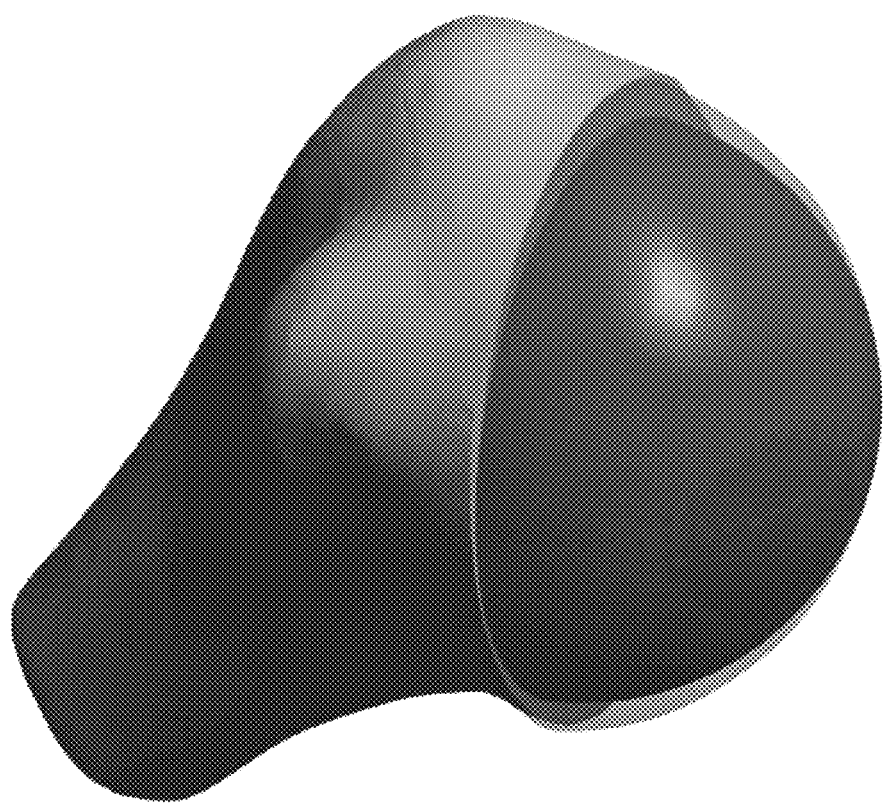
FIG. 62 shows a humeral head cut approximately at the anatomical neck, with comparative views of circular (solid) and non-circular elliptical (transparent) heads.
Figure 63:
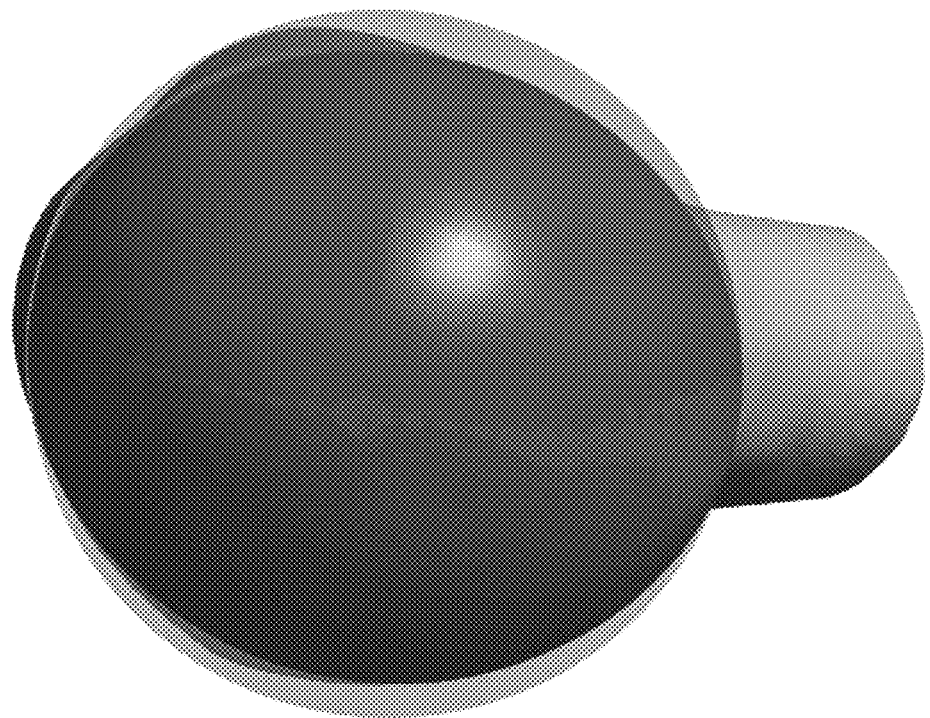
FIG. 63 shows a humeral head cut approximately at the anatomical neck, with comparative views of non-circular elliptical (solid) and circular (transparent) heads.
Figure 64:
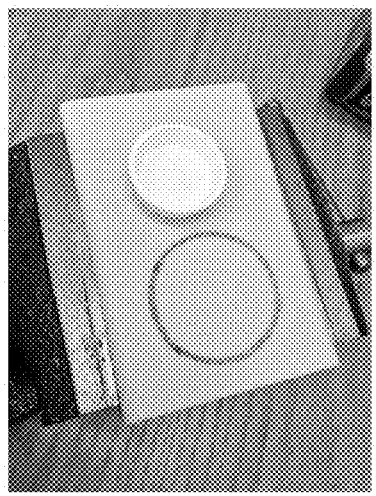
FIG. 64 is a graphic depiction of a step in the sequence of a representative embodiment of a surgical technique for preparing a bone for receiving a circular implant, showing a marking rendered on a substrate, the marking representing the peripheral edge of a bone cut on a humerus, and showing a representative embodiment of a metaphyseal shell; showing a marking rendered on a substrate, the marking representing the peripheral edge of a bone cut on a humerus and an alignment tool aligned therewith for central placement of a pilot hole; showing creation of a pilot hole in the representative bone; and showing a bit for creation of a concentric ring between the bone periphery and the pilot hole.
Figure 64:
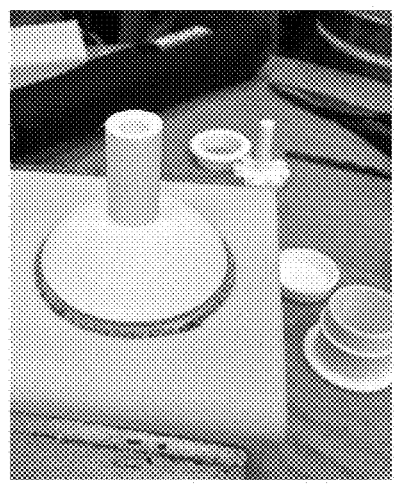
Figure 64:
Figure 64:
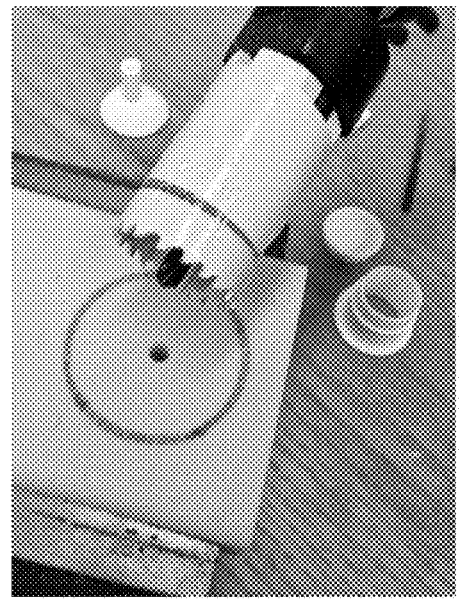
Figure 65:
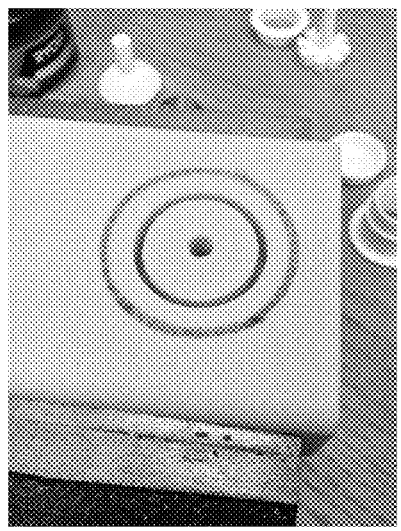
FIG. 65 is a graphic depiction of a step in the sequence of a representative embodiment of a surgical technique for preparing a bone for receiving a circular implant, showing a drilled concentric ring between the bone periphery and the pilot hole; showing placement of a bone guard within the concentric ring that is between the bone periphery and the pilot hole; showing an alternate view of a positioned bone guard within the concentric ring that is between the bone periphery and the pilot hole; and showing an alternate elongate bone guard for guiding a reaming bit.
Figure 65:
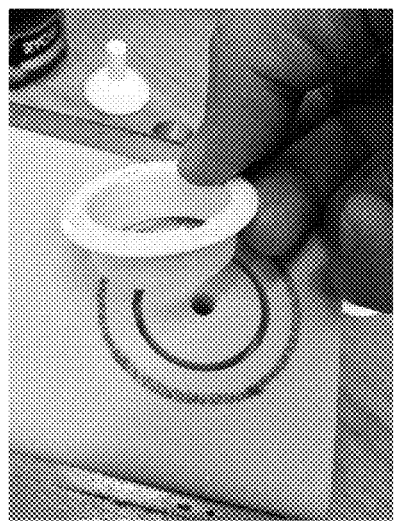
Figure 65:
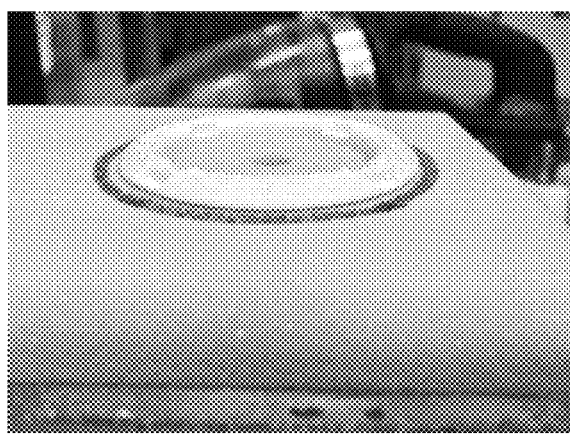
Figure 65:
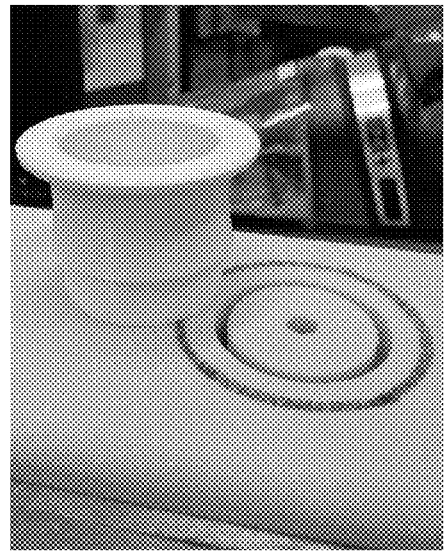
Figure 66:
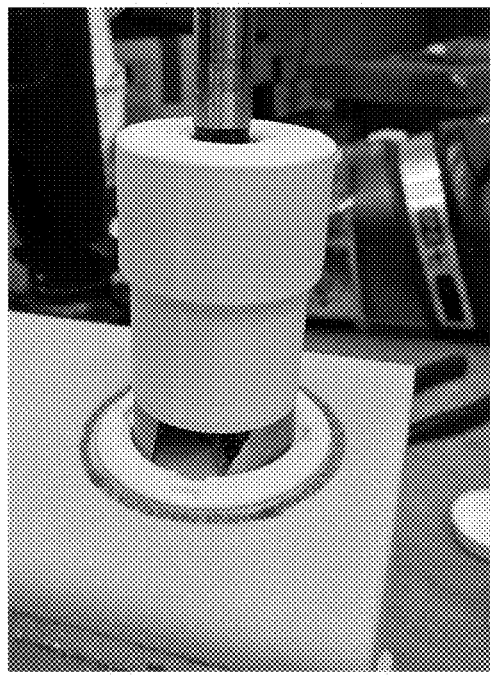
FIG. 66 is a graphic depiction of a step in the sequence of a representative embodiment of a surgical technique for preparing a bone for receiving a circular implant, showing alignment of a reaming bit, such as a Forstner-style bit, with the pilot hole and within the bone guard for reaming the bone; showing positioning of an alternate elongate bone guard for guiding a reaming bit; and showing use of an alternate elongate bone guard for guiding a reaming bit.
Figure 66:
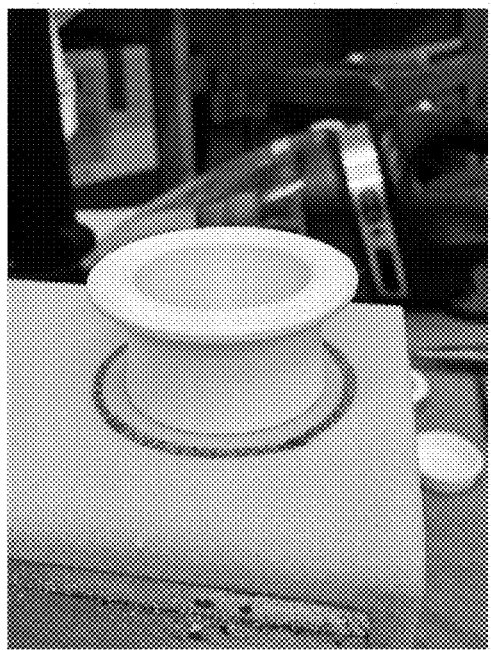
Figure 66:
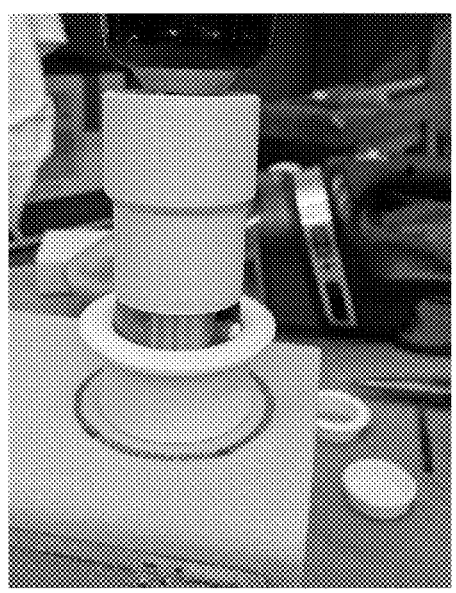
Figure 66:
Figure 67:
FIG. 67 is a graphic depiction of a step in the sequence of a representative embodiment of a surgical technique for preparing a bone for receiving a circular implant, showing use of an alternate elongate bone guard for guiding a reaming bit; showing a removed elongate bone guard and reaming bit for collection of bone material; and showing reamed bone; and, FIG. 68 is a graphic depiction of a step in the sequence of a representative embodiment of a surgical technique for preparing a bone for receiving a circular implant, showing a tapered bone reamer for refined reaming of the bone hole and a representative metaphyseal shell for placement in the bone hole; showing use of the taper reamer; showing the prepared bone; and showing positioning of the representative metaphyseal shell in the prepared bone.
Figure 67:
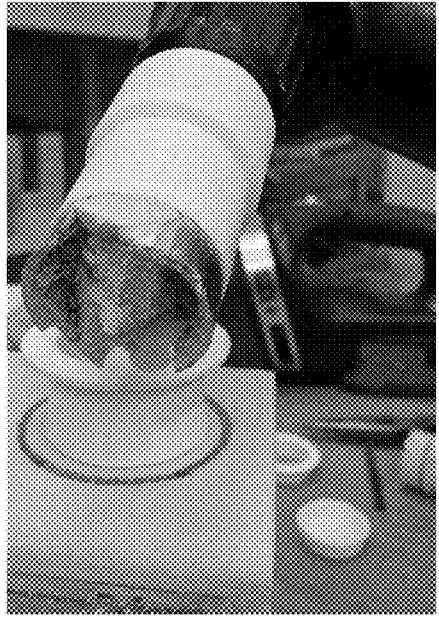
Figure 67:
Figure 67:
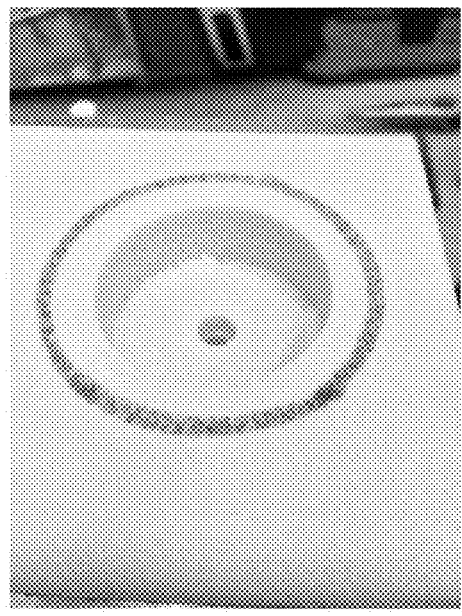
Figure 68:
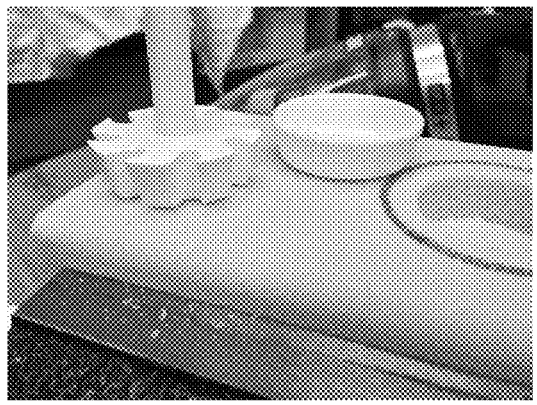
Figure 68:
Figure 68:
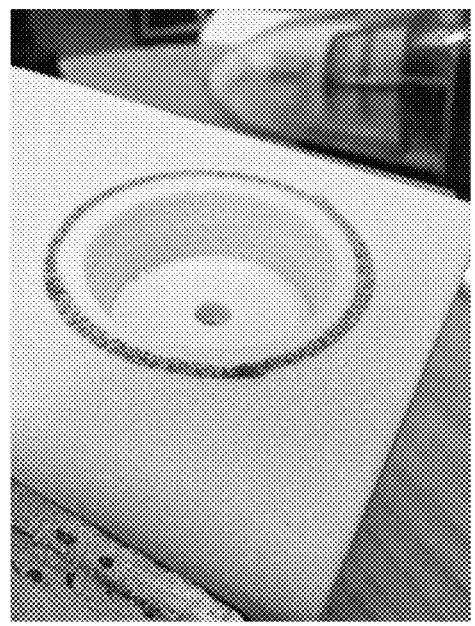
Figure 68:
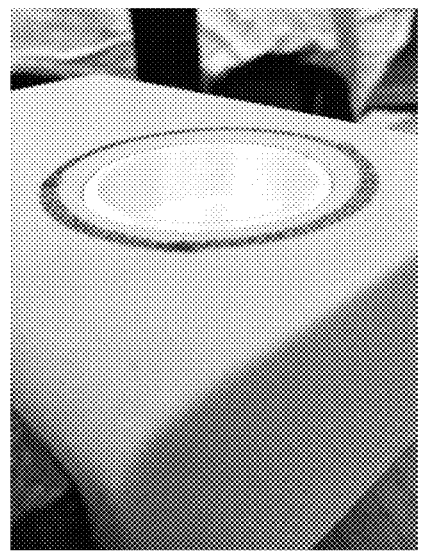

In some embodiments, the prosthesis component is a humeral head prosthesis. Referring again to the drawings, FIGS. 30-31 and FIG. 33-FIG. 38 show various aspects of humeral heads that may be used in accordance with the disclosure. The particular features of overall shape, and dimensions may be selected from those examples generally known in the art. For example, spherical shaped components may be selected, and the component may comprise essentially a full sphere, or a hemisphere, or some greater or lesser fraction thereof. In some embodiments, the shape of the humeral head prosthesis is generally elliptical but non-spherical, allowing an enhanced selection to achieve anatomical matching between the removed native humeral head and the prosthesis. In accordance with the disclosure, use of heads that have a non circular elliptical cross section are particularly desirable for providing the widest array of options to replicate native anatomy and to avoid functional problems for the patient with the arthroplasty. As described further herein below, use of such heads that have a non circular elliptical cross section together with the novel metaphyseal shell coupler component enables the surgeon to accommodate not only offsets in positioning from the AP and SI planes, but also rotational positioning of the heads that have a non circular elliptical cross section to achieve the most desirable replacement anatomy. Referring to the drawings, FIG. 62 and FIG. 63 show alternate comparative views of humeral heads cut approximately at the anatomical neck, each with solid and transparent alternate heads. These drawings illustrate the variable results obtained with an arthroplasty based on selection of a circular vs. non-circular elliptical head. FIG. 62 shows a spherical head in solid overlaid with an elliptical head in transparent to illustrate that a spherical head that is selected for suitable fit in the AP direction would be undersized in the SI direction. FIG. 63 shows an elliptical head in solid overlaid with spherical head in transparent to illustrate that a spherical head that is selected for suitable fit in the SI direction would be oversized in the AP direction, which arrangement could cause rotator cuff tearing and joint stiffness. Thus, while the disclosure encompasses embodiments that include selection of heads that have a circular elliptical cross section, particularly good results can be obtained selecting heads that have a non circular elliptical cross section when used in conjunction with the novel anatomical positioning enabled with the coupler components herein.

In the various embodiments, head prostheses have dimensions that are suited to allow a range of custom fits to a subject's anatomy. As such, heads vary in terms of shape (round to elliptical), height (distance from the surface engagement with the shell to the apex), and peripheral dimension (circumference for round heads and AP to SI dimensions for elliptical heads). In accordance with what is known in the art, the overall shape of the heads at the apex is generally spherical, though the scope of the invention includes use of heads that may have another shape as may be available in the art. In the case of elliptical heads herein, it is contemplated that such heads having spherical apexes would present a glenoid articulation surface that is spherical and would taper along the SI dimensions to the periphery along a generally elliptical arc. It will be appreciated that practice of the invention, particularly with reference to the novel operation of achieving proper offset with a shell to mate a stem with a head or cup, that the shape and size of a head or cup is not limiting.

As described herein, the SI and AP dimensions of a humeral head according to the disclosure are in reference to a cross sectional plane of a humerus essentially in the AP plane with an inclination angle off that plane from about 120 to 145 degrees, and in some embodiments from 120 to 143, and in certain disclosed embodiments herein, of about 135 degrees. The cut corresponds to the anatomical neck of the humerus see URL (//en.wikipedia.org/wiki/Anatomical_neck_of_humerus).

Figure 37:
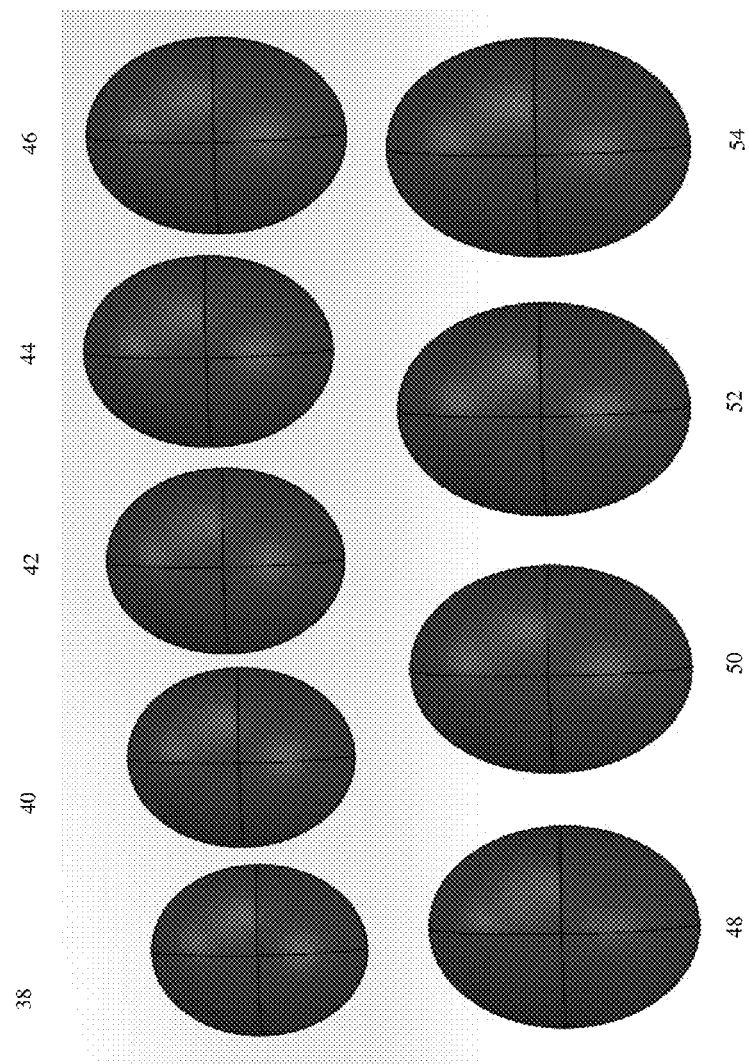
FIG. 37 is a top view of a size array of an embodiment of a prosthesis articulation surface in the form of a elliptical head.
Figure 38:
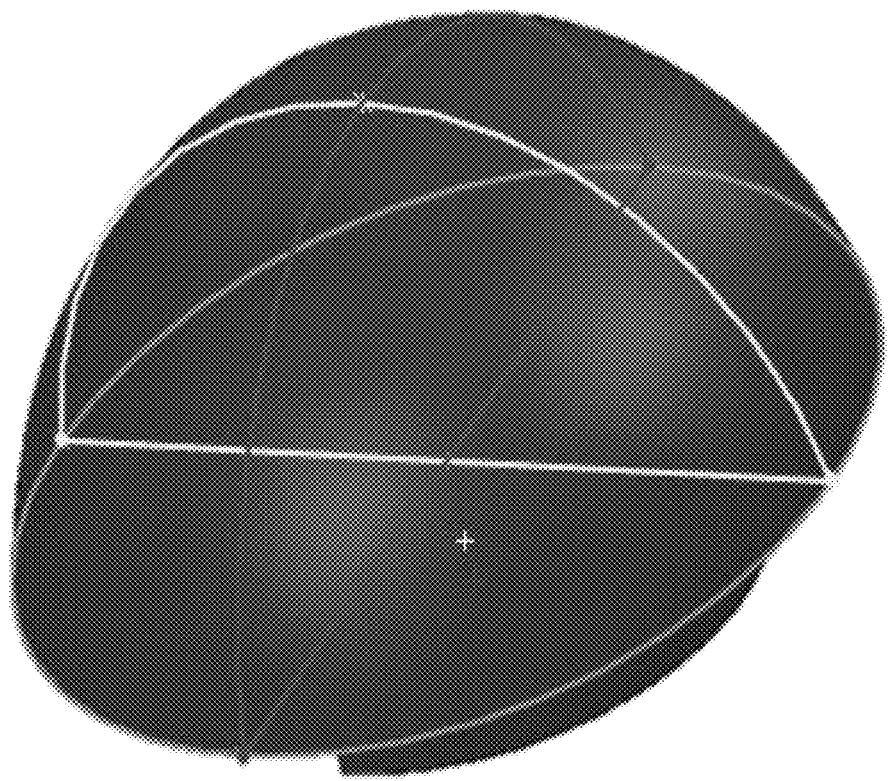
FIG. 38 shows a perspective view of an embodiment of a prosthesis articulation surface in the form of a elliptical head showing the radius of curvature in the AP and SI planes.

Referring again to the drawings, FIG. 37 shows an exemplary array of elliptical heads that vary in size as follows relative to a bone cut on the AP plane: range from 30 mm to 62 mm in the superior to inferior dimension, and range from 30 to 58 mm in the anterior to posterior dimension. In some particular embodiments, the SI range is from 37 to 56 mm and the AP range is from 36 to 51 mm. In yet other embodiments, the SI range can encompass from 20 to 80 mm, and can include sizes in the SI dimension from and including the following and increments in between: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mm. Likewise, in such other embodiments, the AP range can encompass from 20 to 80 mm, and can include sizes in the SI dimension from and including the following and increments in between: 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mm. Selection of the specific size will be made in accordance with the skill in the art and with particular reference to the size and population features of the subject.

In one representative embodiment of an array of elliptical heads, included head sizes may encompass the following array, wherein the AP dimension ranges from 36 to 51 mm, the SI dimension ranges from 37-56 mm, the ratio of AP/SI ranges from 0.87 to 1, and wherein the angle of inclination ranges from 120 degrees to 143 degrees. Specific heads within the array are provided in sizes having head heights ranging from 12 to 25 mm, and in representative embodiments from 14 to 21 mm, and in certain specific embodiments in increments there between.

Figure 35:
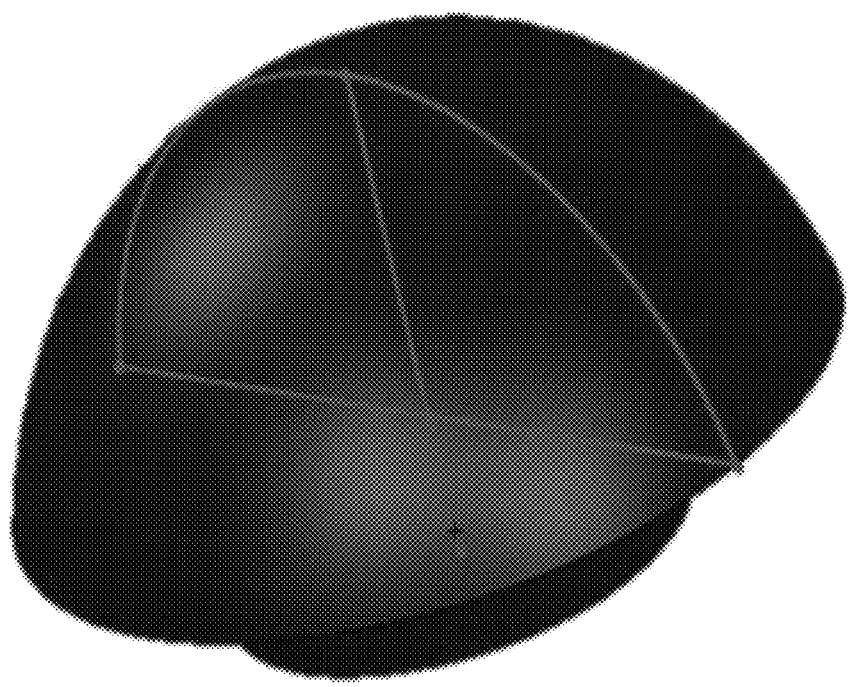
FIG. 35 is a perspective view of an embodiment of a prosthesis articulation surface in the form of a spherical head showing the radius of curvature in the AP plane.
Figure 36:
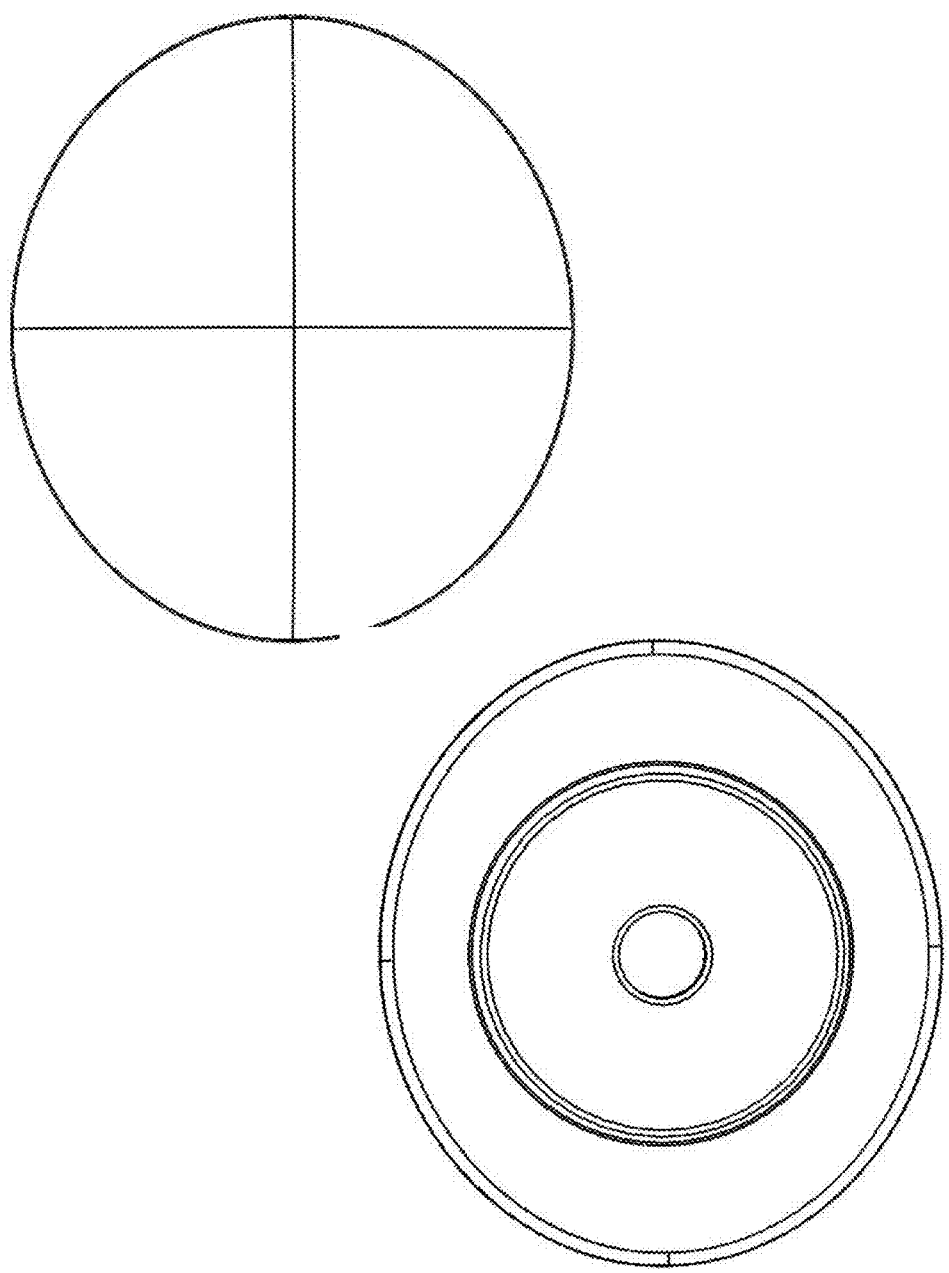
FIG. 36 shows a top view of an embodiment of a prosthesis articulation surface in the form of a elliptical head, and a bottom view of an embodiment of a prosthesis articulation surface in the form of a elliptical head.

The relationship between the SI to AP dimensions in one embodiment of elliptical heads is 1 (spherical heads), as shown in representative FIG. 35. In an alternate embodiment, the SI to AP dimensions are related in a range where the SI dimension is a constant of about 2 mm larger than the AP dimension regardless of head size. In alternate embodiments, the constant of variation between the SI and AP dimensions may vary from 0.5 mm to 10 mm or more, and thus can include constant variation in mm and increments in between including 0.5, 1, 2, 3, 4, 5, 6, 7, 8, 9, 10 mm, as shown in representative FIG. 38. In yet another alternate embodiment, the SI to AP dimensions are related in a range where the AP/SI ratio changes from 1 to 0.85 as the head size increases. Generally, according to such embodiments where the AP/SI ratio changes, the range can include from 0.5, 0.6, 0.7, 0.8, 0.9, 1, 1.5, and 2 and incremental fractions there between.

Cupped Reverse Prosthesis

In some embodiments, the prosthesis component is a cup for placement on the humeral bone in the context of a reverse arthroplasty, and the purpose of which is to articulate with a glenosphere implanted in the scapular. Referring again to the drawings, FIG. 39-FIG. 48 show various aspects of cups that may be used in accordance with the disclosure. A selection of cups may be offered with varying curvatures, pitches, and heights to achieve the anatomical configuration desired by the surgeon for any particular patient. The cup may be formed of a polymer, carbon, or metal or combinations of these, or may be formed of or coated with a material that aids in preventing spalling to avoid osteolysis that is associated with polymer wear and spalling with cupped reverse prosthesis components commonly used in shoulder arthroplasty. In accordance with the various embodiments, the cup is generally cylindrical in shape and may in some embodiments have a modest taper from the top (bearing surface) to the bottom (the shell engagement surface). The bearing surface is concave and essentially spherical in curvature, and the bottom, shell-contacting surface, is essentially planar and adapted to rest on the interior face of the shell. In various embodiments, the cup bears on its lateral circumferential surface engagement means for fixation with the shell. According to certain embodiments, the engagement means include circumferential tabs or teeth as shown in detail in exemplary embodiments shown in FIG. 48 and FIG. 49 that enable a snap fit with corresponding and complimentary structures on the inner wall of the shell as shown in detail in exemplary embodiments shown in FIG. 12 and FIG. 13. The tabs or teeth may be notched to enable alignment and prevent axial displacement, and may include a single structure such as shown in FIG. 48, for example, or may include a plurality, as shown in FIG. 49, for example.

Thus, in accordance with various embodiments comprising more than two engagement structures, the spacing there between may be the same or varied. The engagement features on the cup may be positioned at any location from the top to the bottom wherein corresponding and complimentary features are likewise positioned within the engagement wall of the shell. Representative embodiments of engagement features are shown on the shell in FIG. 11, and on the cup in FIG. 39-FIG. 43, wherein the feature comprises on the shell a single circumferential tooth positioned at the bottom of the internal edge adjacent with the seat of the shell and wherein the feature comprises on the cup a single circumferential tooth positioned at the bottom of the lateral edge adjacent with the bottom edge. Alternate representative embodiments of engagement features are shown on the shell in FIG. 12, and on the cup in FIG. 44-FIG. 48, wherein the feature comprises on the shell a pair of circumferential teeth positioned at the bottom of the internal edge adjacent with the seat of the shell and wherein the feature comprises on the cup a pair of circumferential teeth positioned at the bottom of the lateral edge adjacent with the bottom edge. It will be appreciated by those of skill in the art that the number, position and type of engagement means may be varied in accordance with the skill in the art and that other snap fit type features may be selected for achieving engagement between the shell and the cup.

Modular Humeral Implant (Stemless)

In various embodiments, as shown in FIG. 7-FIG. 10, the disclosure also provides a modular and modular arthroplasty assembly includes (a) a stemless humeral implant configured to be inserted in a humerus and integrated with or adapted for engagement with an metaphyseal shell that is bounded on a first side by an implant surface adapted to receive an implant component and (b) a prosthesis component selected from one of a humeral head and a cupped reverse prosthesis. The stemless humeral implant includes a plug shaped anchor component ("plug") that may be, in various embodiments, solid or hollow and may be optionally threaded, wherein the thread profile and pitch may be selected from those known in the art, for example square threads. The stemless humeral implant also includes a bone engagement rim that extends below the plug for enhanced bone engagement. In various embodiments, either or both the plug and rim may be threaded, wherein the thread profile and pitch may be selected from those known in the art, for example square threads, and may be fenestrated to promote bone ingrowth.

In various embodiments, the methods for implant of the wherein the thread profile and pitch may be selected from those known in the art, for example square threads include surgical techniques wherein one or both the stemless humeral implant and the metaphyseal shell are completely or partially recessed within the humeral bone. According to the various embodiments, placement of one or both the stemless humeral implant and the metaphyseal shell within the bone (i.e., below the cut line) allow a greater range of options with respect to establishing the desired center of rotation in the shoulder joint.

Bone Preparation to Receive Metaphyseal Shell

Figure 52:
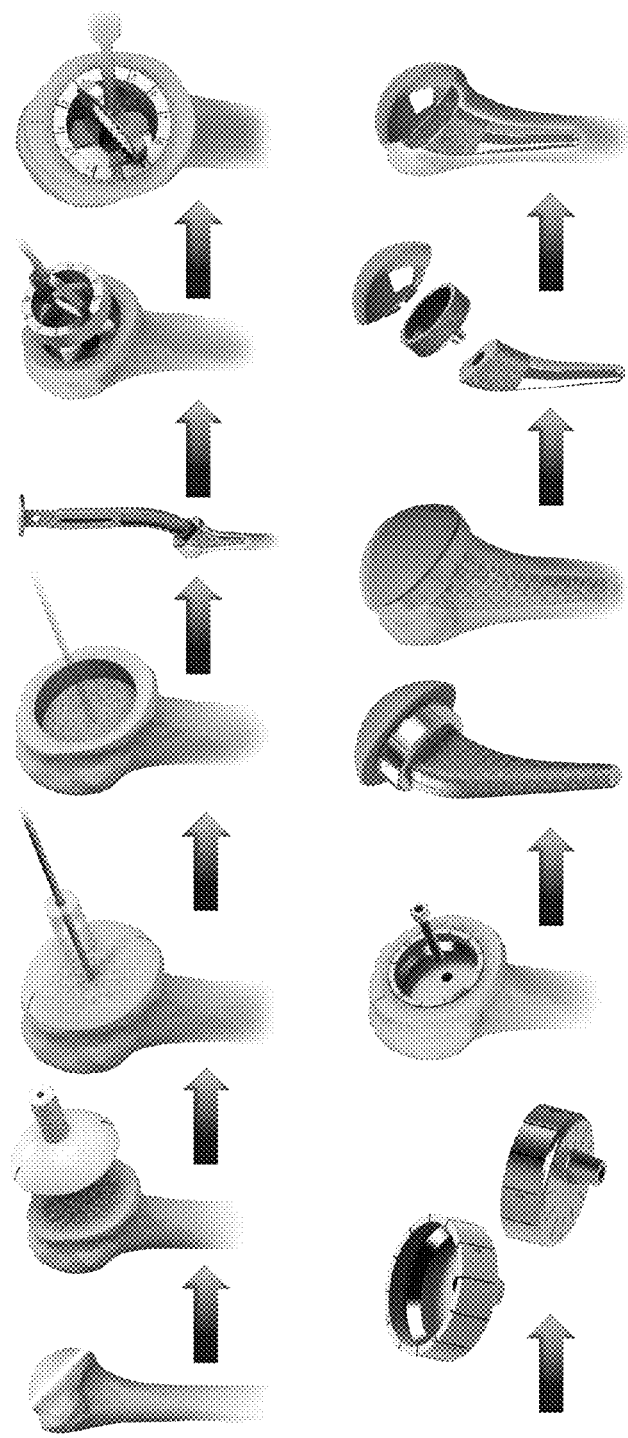
FIG. 52 is a graphic depiction of steps of a representative embodiment of a surgical technique for implanting an arthroplasty system in accordance with the disclosure.

There is a lack of disclosure in the art for preparation of bone to receive a circular implant, particularly in the case of subjects in whom there is weak or compromised bone. It is know that the cavitary region in the metaphysis enlarges with age. Once the head of a humerus or other long bone is resected, it is difficult to ream over a pin because poor bone quality precludes solid fixation of the pin. Thus, it is desirable to implement techniques for bone preparation that protect the bone. In accordance with meeting this need, provided is a representative technique for preparation of bone to receive a partially or fully recessed metaphyseal shell:

Referring again to the drawings, FIG. 52 and the subsequent drawings including specifically FIG. 64 through FIG. 68 show images of steps and alternate steps for bone preparation, which include the steps as follows:

Identify center point of bone; Create pilot hole with drill; Use hole saw to make circular hole (this saw is easy to control and keep centered because it removes little bone); a humeral head protector is placed in the circular hole—the fixation for the humeral head protector is solid such that during surgical exposure of the glenoid as the surgeon levers on the proximal humerus this device keeps the proximal bone from being crushed; if the surgeon wishes, the humeral head protector may be used to guide a Forstner-style bit, and the walls of the protector help the surgeon to better control the trajectory of the bit, which may be otherwise hard to control. Optionally, for enhanced control and to limit the depth of reaming, a "top hat" tubular structure may be used, which the surgeon may choose to stabilize this with his/her fingers; a Forstner-style bit that serves to ream the bone may have a cylinder coupled to it for the purpose of collecting bone graft; the bit is removed and bone graft is collected and prevented the bone graft from spilling into the surgical field; a clean, large-diameter hole with vertical walls has been created, which is further tailored using a larger diameter of the reamer where the vertical walls of the hole serve to center the reamer; a reamer that is shaped similar to the final prosthesis is used to enlarge the proximal, but not distal, aspect of the hole; the hole is ready to accept the final prosthesis, which is perfectly centered within the outline of the centering tool;

Surgical Technique with Modular Convertible Components

In various embodiments, the surgical technique involves access to the proximal humerus bone for removal of the native humeral head and replacement with a modular arthroplasty assembly in accordance with the disclosure. FIG. 52 shows a graphic depiction of steps of a representative embodiment of a surgical technique for implanting an arthroplasty system in accordance with the disclosure.

The specific order of the steps outlined herein below are not intended to be limiting, and not only may the order be varied, but additional steps may be included and certain steps may be eliminated based on the specifics of the anatomy and other factors.

The humeral head is surgically accessed;

The anatomical neck of the humerus is cut (for example, at approximately 135 degrees based on the native anatomy, or at such other angle as may be determined by the surgeon with or without a cut guide) and the native humeral head is removed;

A trial humeral head "sizer" or guide is positioned on the proximal humerus bone cut, the sizer being anatomically shaped like the intended prosthesis heads; the desired size and orientation are determined; the trial head sizer will have a central hole in it;

After proper size and orientation of trial humeral head have been determined, the sizer is fixed in place and a pin is drilled through the center hole in the sizer; the sizer head is removed from over the pin, leaving the pin in place (a K-wire may be used);

A reamer that is size dimensioned to match the size and shape of the metaphyseal shell is selected and placed over the central pin (for example, the size of the metaphyseal shell and corresponding reamer is selected from a set of reamers with dimensions ranging from 30 to 60 mm); the reamer is operated to form a recess cavity in the bone to accommodate the metaphyseal shell (the "metaphyseal shell seat");

A broach/trial prostheses for the humeral stem is selected to find the axis of the diaphysis; starting with the smaller diameter broaches, the bone is trialed and the broaches exchanged for those increasing in size until a trial is identified that provides a snug fit; the trial broaches will be shaped like the diaphyseal portion of the humeral stem portion of the implant;

Optionally, an alternate or second broach/trial for the stem is selected to determine stabilizer size, shape and length to most closely match the anatomy; starting with the smaller diameter stabilizer broaches, the bone is trialed and the broaches exchanged for those increasing in size until a trial is identified that provides a snug fit distally and to a depth that is desirable for the humeral stem portion of the implant;

A feature such as a graduated line or plate or other indicator on the broach handle is used to determine the depth of the broach to achieve alignment of the proximal end of the stem with the bottom of the metaphyseal shell recess (i.e., alignment of the top/proximal surface of the stem with the surface line of the bone in the metaphyseal shell seat); once a snug fit has been achieved, the broach handle is removed; the desired broach depth will provide positioning of the location of the female taper of the broach/trial stem, and a correspondingly sized trial stem is inserted in the bone, and a size guide is positioned over the metaphyseal shell bone cut to determine offset positioning for the male taper of the metaphyseal shell with the female channel of the stem;

A metaphyseal shell with the appropriate offset for engagement with the stem is selected (offset examples include 0, 2, 4, or 6 mm of offset) and placed in the bone, its male taper engaged with the female taper of the stem; a screw is inserted or another coupling device is utilized to engage the trial metaphyseal shell with the broach/trial stem to complete the trial implant system;

A trial prosthesis is selected, such as from a humeral head or reverse arthroplasty cup prostheses;

The trial implant is removed, the screw or other coupling device will have locked the orientation of the metaphyseal shell relative to the stem and indicators on the metaphyseal shell (for example, numbered 1-12 to indicate position, like the face of a clock) will provide a key for the surgeon as to how to assemble the final components for implantation (e.g., from the trial components an indicator #3 on the metaphyseal shell may align with a particular marker indicator on the proximal end of the stem, so the final component is then assembled to match these indicators), using the sizes of metaphyseal shell and stems as selected with the trials with a predetermined size enhancement (dimensions slightly greater than the trial, as predetermined) to ensure a tight press fit into the bone;

The full implant is assembled on the bench, and then press fit into the bone such that all or substantially the entire metaphyseal shell is below the bone surface, and so that all or substantially the entire stem is below the bone surface at the base of the metaphyseal shell seat;

It will be appreciated that the above technique may be varied, and that the components described are merely exemplary, and features size as engagement means, as well as dimensions, and engagement indicators and gauges may be varied, and are thus non-limiting;

Determining Offset Positions of Prosthesis Components

In various embodiments, the surgical technique involves access to the proximal humerus bone for removal of the native humeral head and replacement with a modular arthroplasty assembly in accordance with the disclosure. The specific order of the steps outlined herein below are not intended to be limiting, and not only may the order be varied, but additional steps may be included and certain steps may be eliminated based on the specifics of the anatomy and other factors. Instruments and the technique referred to herein are shown in the drawings, FIG. 52 shows a graphic depiction of steps of a representative embodiment of a surgical technique for implanting an arthroplasty system in accordance with the disclosure.

Figure 53:
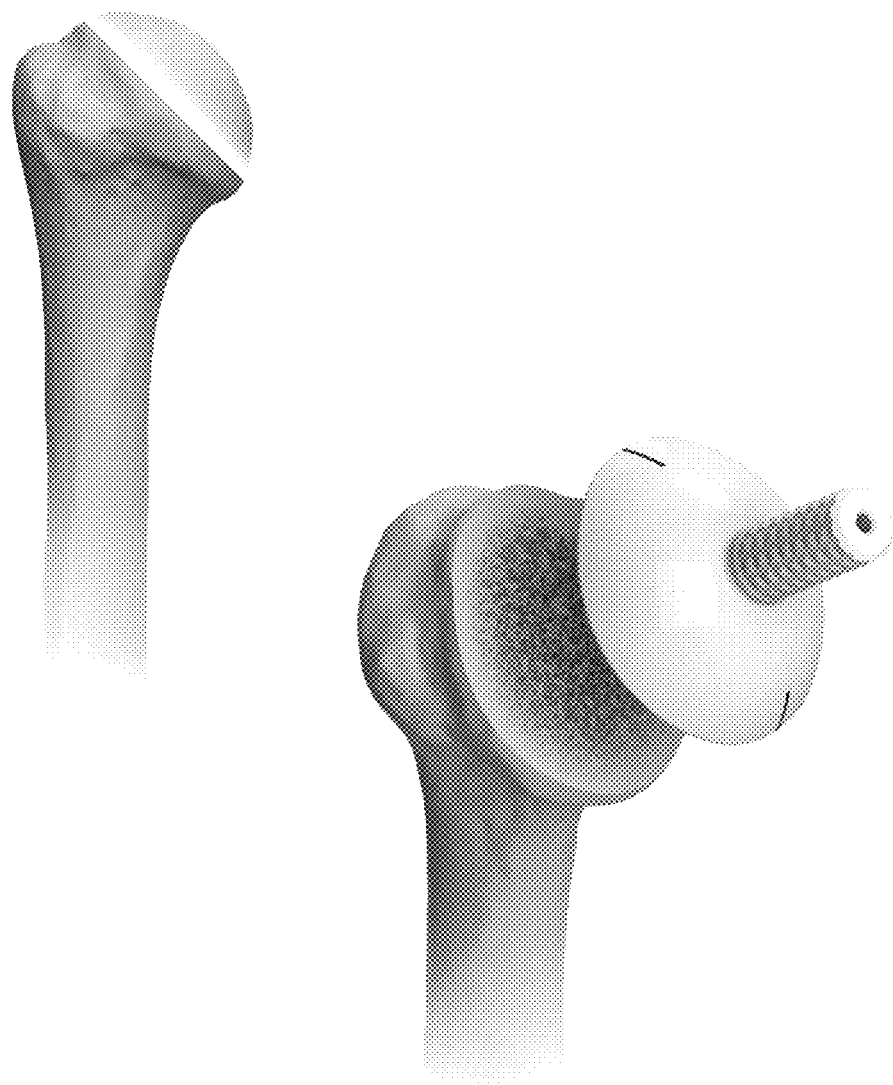
FIG. 53 is a graphic of a step in the sequence of a representative embodiment of a surgical technique for implanting an arthroplasty system in accordance with the disclosure showing a side view of a humerus and a cut line for excision of a portion of the humeral head, and showing a perspective view of a bone cut on a humerus revealing metaphyseal bone and alignment tool for central placement of a Kirchner wire ("K-wire")
Figure 54:
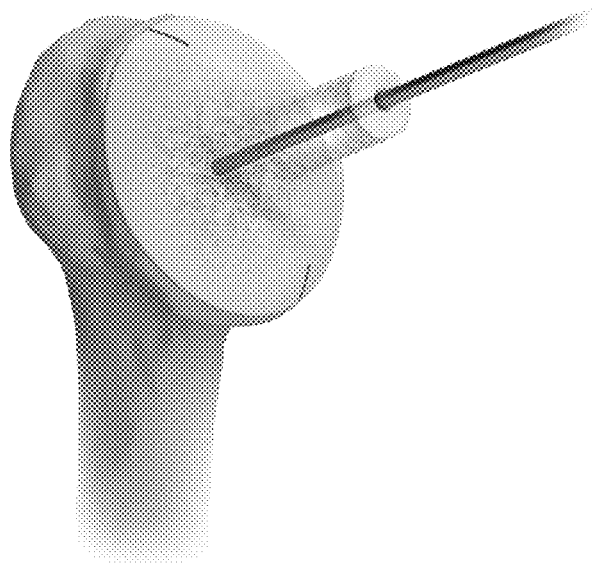
FIG. 54 is a graphic of a step in the sequence of a representative embodiment of a surgical technique for implanting an arthroplasty system in accordance with the disclosure showing a perspective view of a bone cut on a humerus revealing metaphyseal bone and alignment tool positioned on the bone cut and placement of a K-wire, and showing a perspective view of a bone cut on a humerus revealing reamed metaphyseal bone and K-wire.
Figure 54:
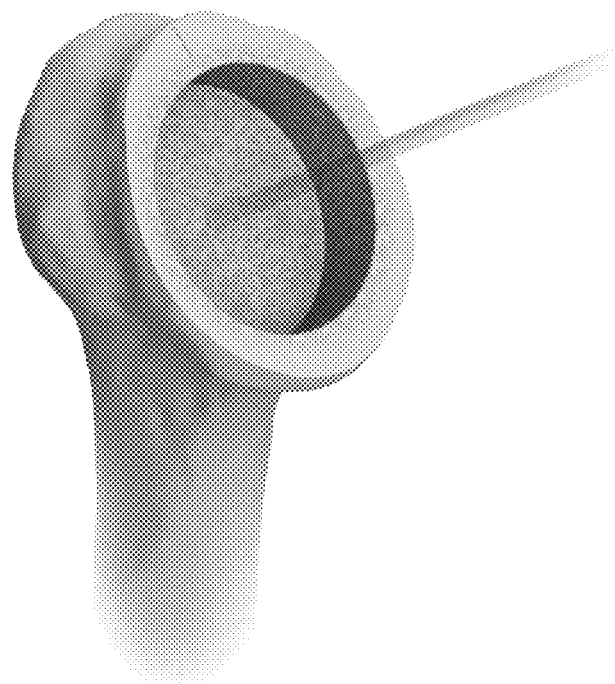
Figure 56:
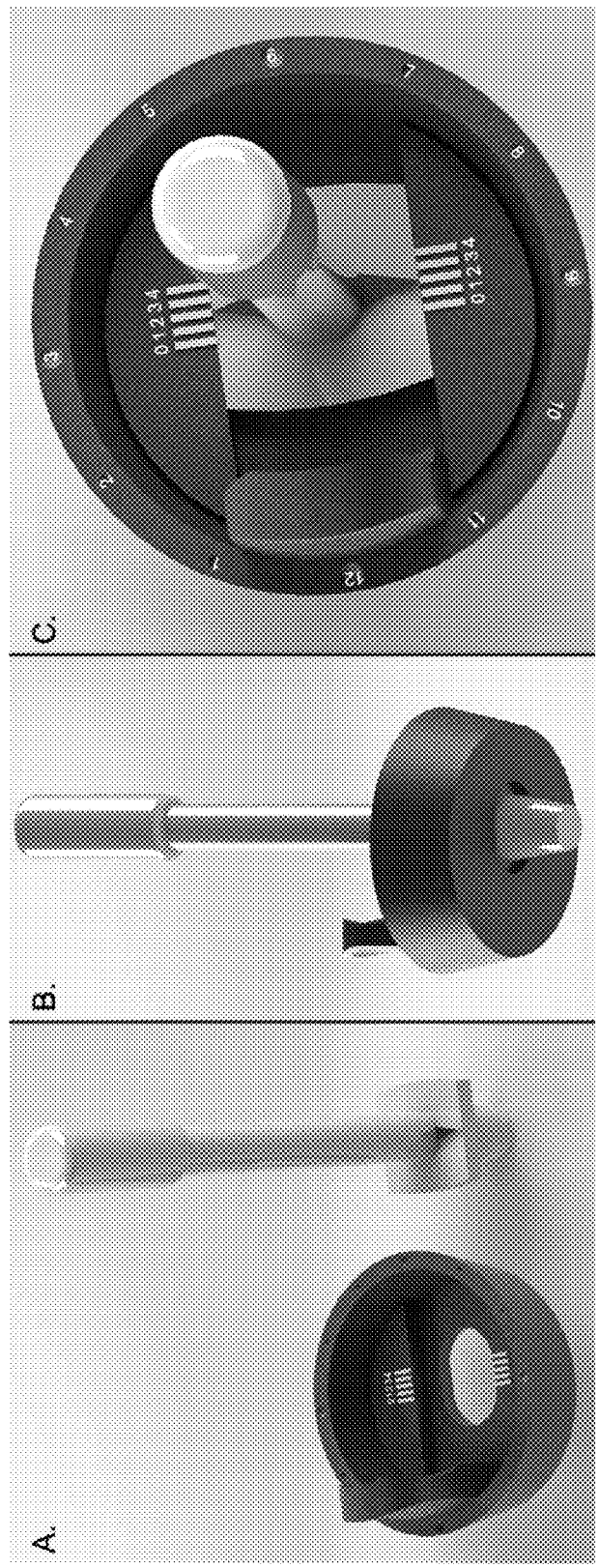
FIG. 56 shows a representative embodiment of an offset tool.
Figure 57:
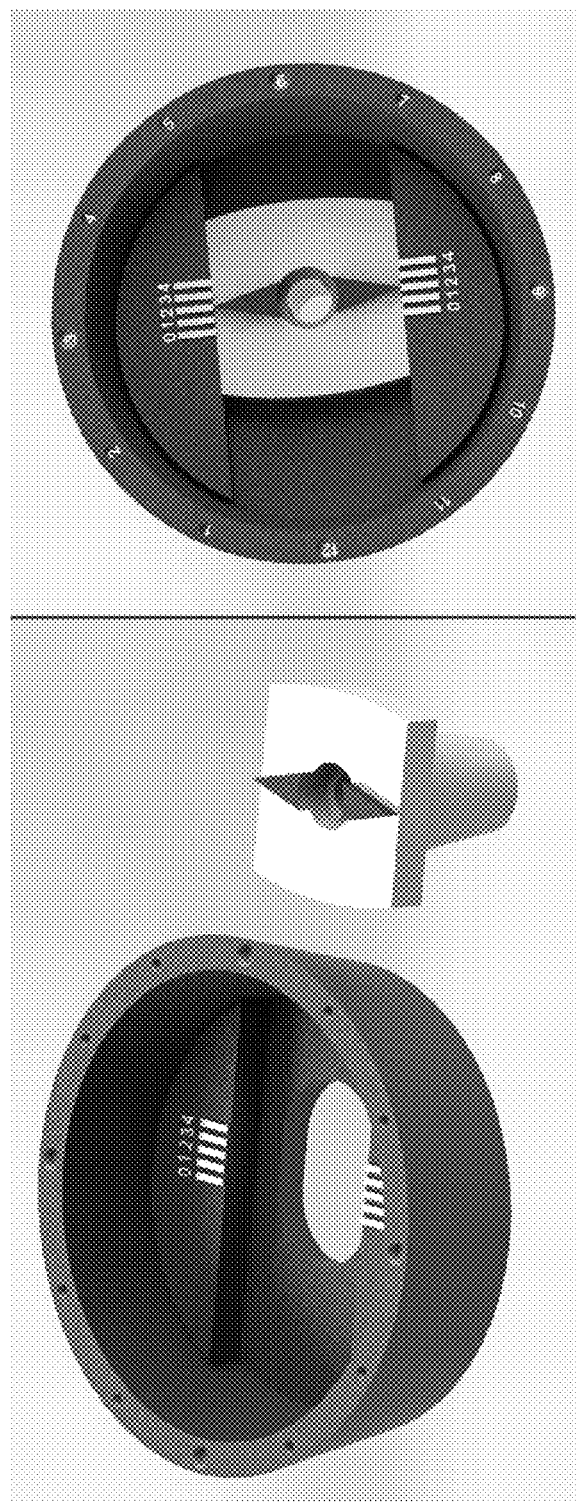
FIG. 57 shows an alternate view of the representative embodiment of an offset tool shown in FIG. 56.
Figure 58:
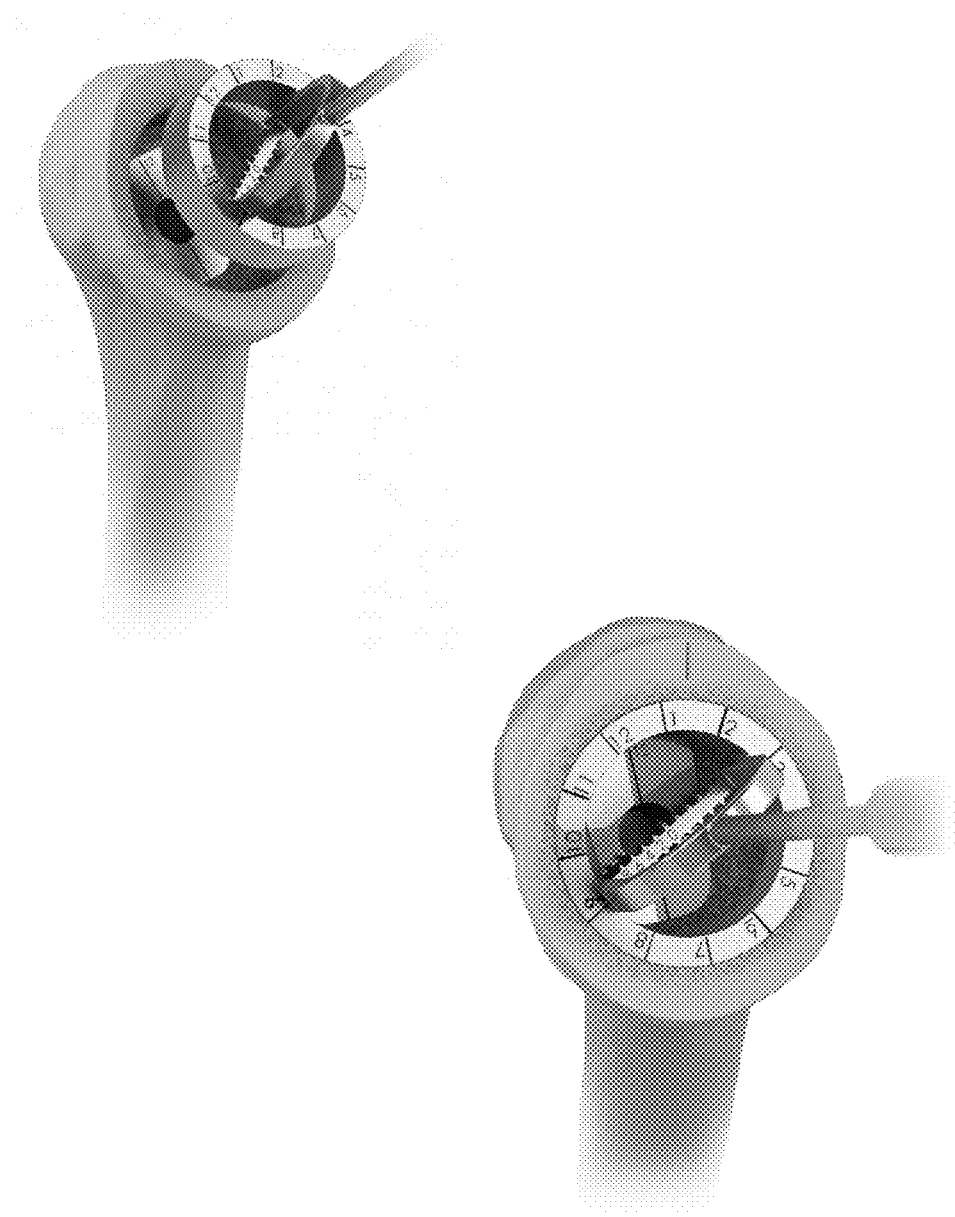
FIG. 58 is a graphic of a step in the sequence of a representative embodiment of a surgical technique for implanting an arthroplasty system in accordance with the disclosure showing a perspective view of a bone cut on a humerus with a stem trial in place and representative shell offset selection tool, and showing a perspective view of a bone cut on a humerus with a stem trial and representative shell offset selection tool in place indicating selected offset.
Figure 59:
FIG. 59 is a graphic of a step in the sequence of a representative embodiment of a surgical technique for implanting an arthroplasty system in accordance with the disclosure showing alternate perspective views of a bone cut on a humerus with a representative shell trial with indicators for offset selection, and arthroplasty system in accordance with the disclosure showing a perspective view of a bone cut on a humerus with a stem trial and shell trial and engagement pin.

FIG. 53 shows a graphic of a step in the sequence of a representative embodiment of a surgical technique for implanting an arthroplasty system in accordance with the disclosure showing a side view of a humerus and a cut line for excision of a portion of the humeral head. According to the surgical technique, the humeral head is surgically accessed and the anatomical neck of the humerus is cut (for example, at approximately 135 degrees based on the native anatomy, or at such other angle as may be determined by the surgeon with or without a cut guide) and the native humeral head is removed;

A trial humeral head "sizer" or guide is positioned on the proximal humerus bone cut, the sizer anatomically shaped like the intended prosthesis heads; the desired size and orientation are determined; the trial head sizer will have a central hole in it;

After proper size and orientation of trial humeral head have been determined, a mark is made on the bone that correlates with a marker at the 12 o'clock position on the trial sizer head, the sizer is held in place and a pin is drilled through the center hole in the sizer; the sizer head is removed from over the pin, leaving the pin in place (a K-wire may be used);

A reamer that is size dimensioned to match the size and shape of the metaphyseal shell (line to line) is selected and placed over the central pin (in some examples the size of the metaphyseal shell and corresponding reamer is selected from dimensions from 30 to 60 mm, and may be in some examples 40 mm or 35 mm); the reamer is operated to form a recess cavity in the bone to accommodate the metaphyseal shell (the "metaphyseal shell seat");

A broach/trial prostheses for the humeral stem is selected to find the axis of the diaphysis; starting with the smaller diameter broaches, the bone is trialed and the broaches exchanged for those increasing in size until a trial is identified that provides a snug fit; the trial broaches will be shaped like the diaphyseal portion of the humeral stem portion of the final implant and in some embodiments there is a plate on the broach handles to control depth and to check for proper orientation;

Optionally, an alternate or second broach/trial for the stem is selected to determine stabilizer size, shape and length to most closely match the anatomy; starting with the smaller diameter stabilizer broaches, the bone is trialed and the broaches exchanged for those increasing in size until a trial is identified that provides a snug fit distally and to a depth that is desirable for the humeral stem portion of the implant;

A feature such as a graduated line on the broach handle is used to determine the depth of the broach to achieve alignment of the proximal end of the stem with the bottom of the metaphyseal shell recess (i.e., alignment of the top/proximal surface of the stem with the surface line of the bone in the metaphyseal shell seat); once a snug fit has been achieved, the broach handle is removed; the desired broach depth will provide positioning of the location of the female taper of the broach/trial stem, and a correspondingly sized trial stem is inserted in the bone, and a size guide is positioned over the metaphyseal shell bone cut to determine offset positioning for the male taper of the metaphyseal shell with the female channel of the stem;

Once a snug fit has been achieved, the broach handle is removed and a female taper of the broach/trial stem can be seen; an offset instrument for the metaphyseal shell is used, the instrument having a generally circular profile and an index feature at its center and a long handle whereby the generally circular portion is inserted into the prepared cavity as shown in representative FIG. 56-FIG. 58, the posterior offset amount is recorded, and using markings on the instrument, the metaphyseal shell-to-stem, and metaphyseal shell-to-head positions are identified and recorded. Referring now to FIGS. 56 and 57, a representative embodiment of an offset tool is shown. In one embodiment of use, the trial shell (disc shaped with a central recess) is inserted into the prepared bone and rotated such that the hole in the base of the trial shell aligns with the female receptacle in the stem/broach (previously placed); the taper/gauge (elongate member with proximal grip and distal substantially square shaped engagement feature) is inserted through the central hole in the shell so that it engages the female receptacle in the stem/broach to achieve proper alignment of both shell and taper relative to the bone and stem/broach, and the offset readings for shell offset and rotational orientation are recorded using the exemplary markings.

Referring again to the drawings, FIG. 58 shows an alternate representative embodiment of an offset tool that includes, as shown, positional 1-12 markings that correspond to conventional analog clock number positions, (it will be appreciated that other indicator features may be used and the selection of an analog clock marking features is not intended to be limiting, and any other indictors and marks, whether comprising letters, numbers, symbols and combinations of these may be used);

A metaphyseal shell with the appropriate offset for engagement with the stem is selected (offset examples include 0, 2 and mm of offset, for example: 0, +2, +4, +6, +8) and placed in the bone, its male taper engaged with the female taper of the stem; a set screw is inserted to engage the trial metaphyseal shell with the broach/trial stem to complete the trial implant system and the position of the metaphyseal shell relative to the bovie line can again be recorded;

The etched marking is aligned with the mark on the bone, the trial humeral prosthesis is selected and engaged with the metaphyseal shell to complete the trial prosthesis;

The trial implant is removed, the screw will have locked the orientation of the metaphyseal shell relative to the stem and indicators on the metaphyseal shell (for example, numbered 1-12 to indicate position, like the face of a clock) will provide a key for the surgeon as to how to assemble the final components for implantation (e.g., from the trial components an indicator #3 on the metaphyseal shell may align with a particular marker indicator on the proximal end of the stem, so the final component is then assembled to match these indicators), using the sizes of metaphyseal shell and stems as selected with the trials with a predetermined size enhancement (dimensions slightly greater than the trial, as predetermined) to ensure a tight press fit into the bone;

The full implant is assembled using the pre-recorded positions for offset, metaphyseal shell-to-stem, and metaphyseal shell-to-head of the trial prosthesis; the final prosthesis being slightly larger than the trial prosthesis in order to achieve a press fit;

Finally, the implant is press fit into the bone such that all or substantially the entire metaphyseal shell is below the bone surface, so that all or substantially the entire stem is below the bone surface at the base of the metaphyseal shell seat;

It will be appreciated that the above technique may be varied, and that the components described are merely exemplary, and features size as engagement means, as well as dimensions, and engagement indicators and gauges may be varied, and are thus non-limiting.

Exemplary Surgical Preparation and Implantation of Humeral Modular Assembly

In yet another particular embodiment, the following surgical technique is used for implantation of a shoulder prosthesis;

Humeral Head Osteotomy:

Using a humeral head cut guide, Resect humeral head at about 135 degrees of inclination;

Humeral Head Sizing and Orientation:

Select an optimally sized, anatomic pin guide. Record the size selected. Position guide flat on the humeral head cut with the etched medial-lateral orientation-markers at the most superior and inferior locations of the cut (the 12 and 6 positions on the face of the cut);

Alignment Pin Placement:

Once optimal size and orientation are achieved, using a bovie, mark the location of the superolateral orientation marker on the superior aspect of the greater tuberosity. Holding the anatomic pin guide in proper orientation, under power, pass an alignment pin through the cannula and into the proximal humerus to a depth at the level of the lateral cortex. Remove anatomic pin-guide and record humeral head size for trial head and definitive implant selections;

Metaphyseal Preparation:

Select the optimally sized 30-44 mm cannulated metaphyseal reamer. Allow enough peripheral bone to accommodate an additional 2 mm of proximal humeral bone displacement for optimal press-fit fixation of the definitive metaphyseal shell. Pass the cannulated metaphyseal reamer over the alignment pin. Under power, ream the humeral metaphysis to a positive-stop;

Diaphyseal Preparation:

Assemble modular impaction handle and broach/compactor (TBD) stem. Align the superolateral alignment marker on the modular impaction handle with the superolateral reference marker on the greater tuberosity (created in Step 2). Sequentially broach/compact diaphysis to a positive-stop (at the level of the broach/compactor metaphyseal shell) until cortical bone contact is achieved. With the definitive broach/compactor fully seated, release the modular impaction handle, leaving the broach/compactor stem in place to serve as the trail stem;

Determining Metaphyseal Shell Offset:

Select the appropriately sized (30-44 mm) metaphyseal shell offset guide and insert into reamed metaphyseal cavity until the distal portion of the metaphyseal shell offset guide is fully seated on reamed surface. Rotate the metaphyseal shell offset guide until the distal offset ruler bisects the center of the female Morse taper. Record the amount of posterior offset (1 mm to 12 mm) required for optimal metaphyseal shell orientation. Prior to removing the metaphyseal shell offset guide; use the greater tuberosity reference indicator (created in Step 2) and the outer positioning dial of the metaphyseal shell offset guide, record the optimal rotational position for the metaphyseal shell;

Trial Metaphyseal Shell Placement:

Referencing the measurements recorded off of the metaphyseal shell offset guide in Step 6, select the appropriate sized (30-44 mm) metaphyseal shell trial with the optimal amount of offset (0, +1, +2, +4, +8). Align the rotational position indicator of the trial metaphyseal shell (recorded in Step 6) with the greater tuberosity reference mark. Introduce the metaphyseal shell trial until the male taper is fully seated into the female table of the trial stem. Introduce and fully seat the trial metaphyseal shell set screw to ensure a secure humeral trial assembly. Record the definitive position of the metaphyseal shell using the rotational reference dial and greater tuberosity superolateral indicator mark;

Trial Head Positioning and Assembly:

Select the humeral head trial that corresponds to optimally sized anatomic pin guide (recorded in Step 3). If optimal humeral head cut coverage is not initially achieved, select a larger or smaller diameter trial as needed. Align the trial humeral head orientation markers with the superolateral marking on the greater tuberosity. Insert the humeral head trial into the metaphyseal shell trial until fully seated. Lightly impact the humeral head trial until rotational stability is achieved;

Definitive Implant Assembly:

Remove the trial prosthesis, fully assembled, such as with a threaded slap hammer. Referencing the trial stem to trial metaphyseal shell orientation markers and the trial metaphyseal shell to trial humeral head orientation markers, orient and assemble the definitive humeral components in their optimal anatomic positions. (As defined by the trail humeral prosthesis);

Surgical Technique for Revision Surgery Using Modular Convertible Components

In various embodiments, the surgical technique for a revision surgery after initial implantation of the modular arthroplasty assembly involves access to the proximal humerus bone. Once accessed, the original prosthesis is removed and replaced with a new prosthesis of either the same type, or another type. For example, the revision may involve replacement of a humeral head prosthesis with another humeral head prosthesis. Or the revision may be to achieve a reverse shoulder, in which case the humeral head prosthesis is replaced with a cupped reverse prosthesis. The specific order of the steps outlined herein below are not intended to be limiting, and not only may the order be varied, but additional steps may be included and certain steps may be eliminated based on the specifics of the anatomy and other factors;

The humeral head is surgically accessed;

A saw or other suitable tool is used to remove any superficial bony growth from the edge and outer surfaces of the prosthesis;

A suitable tool is used to disengage the prosthesis, optionally accessing available osteotome slots as needed;

Optionally, the metaphyseal shell is removed and a replacement metaphyseal shell is positioned by press fitting to accommodate a replacement prosthesis wherein the replacement shell may include one or a combination of a different circumferential size, a different offset, and different prosthesis engagement features for engagement with a head or a cup, as needed;

A replacement prosthesis is selected and engaged with the metaphyseal shell;

Other surgical steps are taken to complete the surgery;

Shoulder Arthroplasty Trials and Instruments

Figure 60:
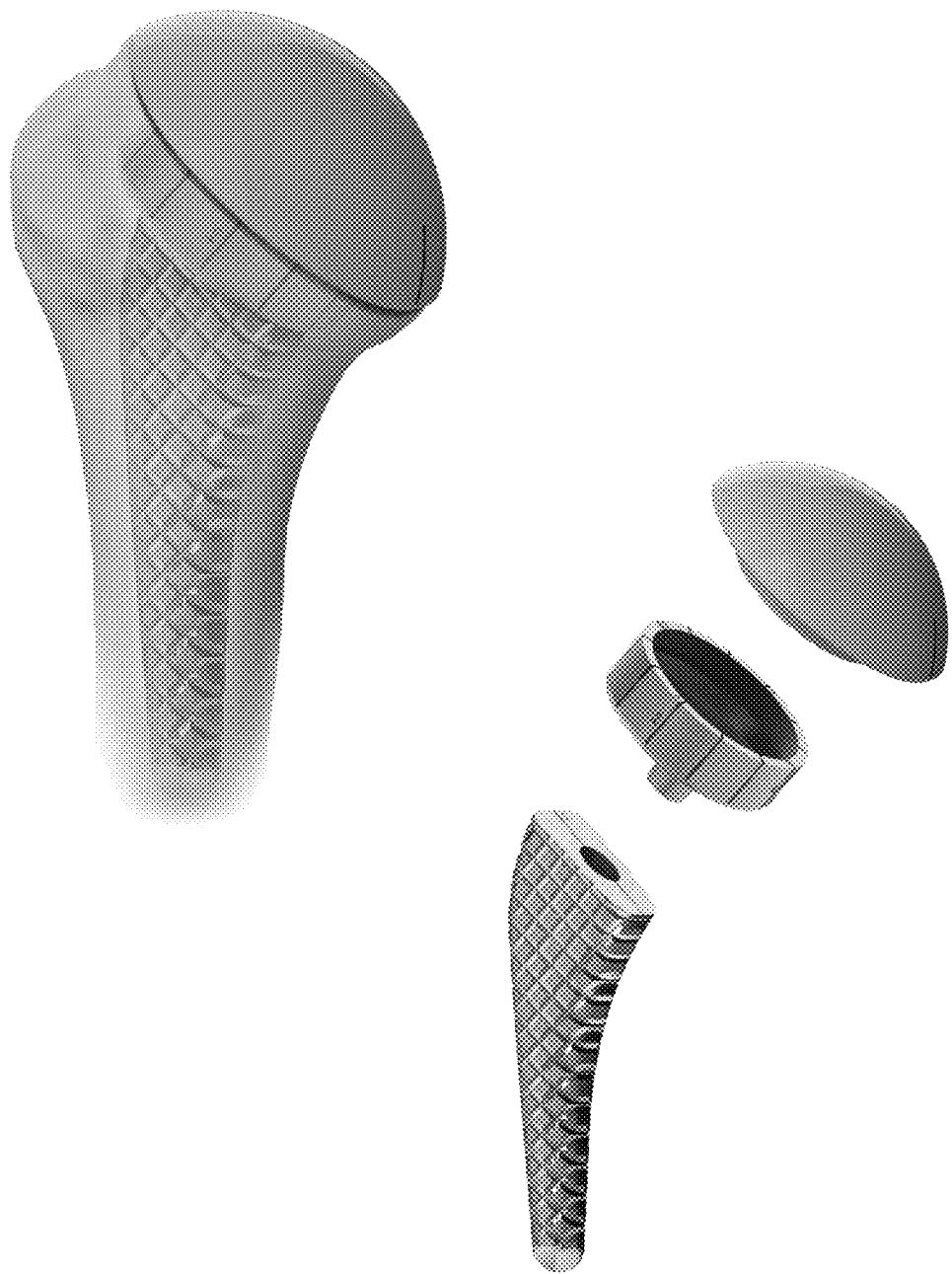
FIG. 60 is a graphic of a step in the sequence of a representative embodiment of a surgical technique for implanting an arthroplasty system in accordance with the disclosure showing a perspective view of a bone cut on a humerus with a stem trial, shell trial and head trial in bone, and showing an exploded perspective view of a stem trial, shell trial and head trial.
Figure 61:
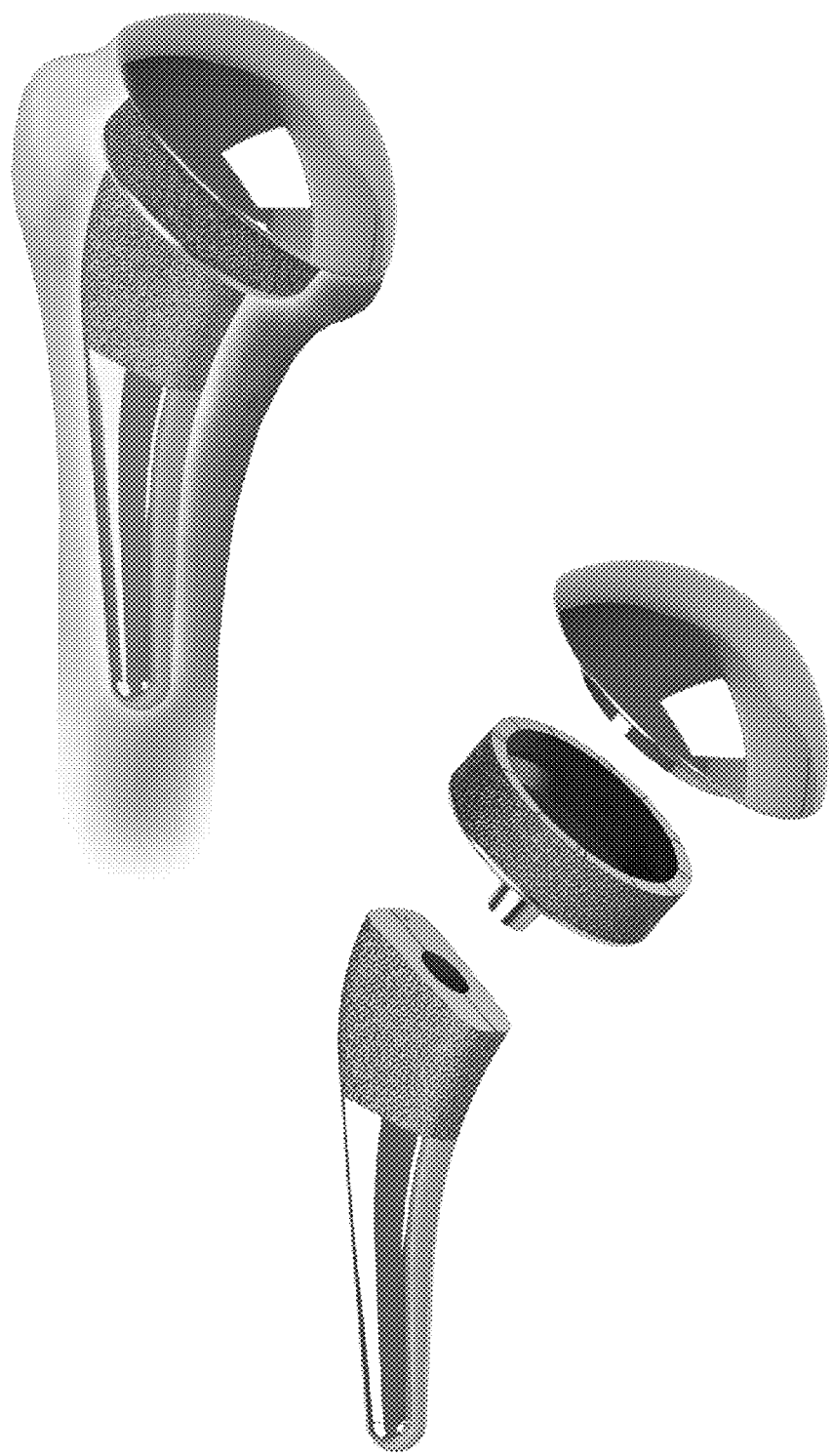
FIG. 61 is a graphic of a step in the sequence of a representative embodiment of a surgical technique for implanting an arthroplasty system in accordance with the disclosure showing an exploded perspective view of an assembly with representative surface features of a stem, a shell, and a head, and showing a perspective view of an assembled stem shell and head in bone with representative surface features.

In exemplary embodiments, trials for exemplary embodiments of prostheses components are provided herein, the representative embodiments shown in FIG. 60 are trial humeral heads. This disclosure also contemplates and provides exemplary instruments to achieve shoulder arthroplasty procedures in accordance with the inventive components and techniques herein. Disclosed herein are representative instruments including trial humeral head "sizer" or guide instrument, a stem trial broach handle with depth indicator or guide, and a metaphyseal shell offset instrument. In the exemplary embodiments described herein and shown in the drawings, the instruments have features to enable custom implant selection and positioning.

In exemplary embodiments, trials for the metaphyseal shell are provided herein. The trials are adapted for engagement with a trial or long bone stem prosthesis component, such as a humeral stem according to various embodiments disclosed herein, and with a trial or prosthesis component, in some examples selected from the humeral head and cupped reverse prosthesis prostheses disclosed herein. An exemplary embodiment of a metaphyseal shell trial is shown in FIG. 70, wherein the trial has an eccentrically positioned male tapered coupler for engagement with a female tapered receptacle on a corresponding stem component, and the trial bears markings identifying its offset position to ensure custom fit alignment of the shoulder implant components within the humerus of a patient. In working embodiments, a selection of metaphyseal shell trials is provided, each with different offsets, and bearing markings for indication of offset and positioning of an implant prosthesis component (for example head or cupped reverse prosthesis).

Of course, it will be appreciated by one of ordinary skill that the scheme of markers and selection of indicators on the shell positioning tools may be varied without departing from the scope of the invention.

One exemplary offset instrument for the coupler component metaphyseal shell is shown in FIG. 56 and FIG. 57. According to this embodiment, the offset measurement tool is shaped according to the selected shape of the shell implant, in the depicted embodiments in FIG. 56 and FIG. 57 as frustoconical. The shell includes a cut out in its center with positional indicators in the form of metered markings, and an insertion tool that fits through the cut out and is adapted with an engagement feature to engage with a placed stem trial. In use, the trial shell is inserted into the prepared bone and rotated such that the hole in the base of the trial shell aligns with the female receptacle in the stem/broach, the insertion tool is inserted through the central hole in the shell so that it engages the female receptacle in the stem/broach to achieve proper alignment of both shell and taper relative to the bone and stem/broach, and the offset readings for shell offset and rotational orientation are recorded using the exemplary markings.

In an optional additional embodiment of use, the modular trial shell may include a screw or other fixation element that passes through the taper/gauge insertion tool and locks into the broach/stem enabling the entire assembly of the trial anchor and trial shell to be used as both a trial prosthesis as well as a measuring device—saving steps as well as inventory. In this embodiment, the inventory can be reduced by eliminating trial shells each with different offsets and thus have dual purpose tool that achieves the offset measurement and is provided in the desired array of sizes selected from, for example, 34, 36, 38, and 40 mm.

An alternate offset instrument for the metaphyseal shell, as shown in representative embodiments in FIG. 58, has an offset dial that is generally circular in profile and substantially matches the profile of the metaphyseal shell and is adapted for easy insertion in the reamed bone to approximate the metaphyseal shell. The offset dial includes an index feature at its center, a dial etched around its periphery, and a long handle whereby the generally circular offset dial is inserted into the prepared bone cavity as shown in representative FIG. 58. This single instrument can be used to establish any superior to inferior and anterior to posterior offset needed between the center of the metaphyseal shell and the anchor and the rotational orientation of the head. Of course, other tools and methods may be used to measure these offset and rotational features. In use, the offset is recorded relative to the position of the female taper in the stem trial to enable selection of the appropriate metaphyseal shell. Using markings on the instrument, such as for example the shown 1-12 markings that correspond to conventional analog clock number positions, the metaphyseal shell-to-stem, and metaphyseal shell-to-head positions are identified and recorded to allow for optimal anatomical positioning of the implant prosthesis during its implantation. Of course, it will be clear to one of ordinary skill that the instrument may vary in material, length, and implements for guiding insertion of the offset dial with the bone cut, and as such, the exemplary embodiment is merely representative. In alternate embodiments, the offset dial may have other index features that aid in establishing appropriate offset of the metaphyseal shell relative to the stem and the head. Likewise, any of a variety of handle features and configurations known in art may be utilized to facilitate handling and positioning of the instrument relative to the stem and humerus.

In exemplary embodiments, trials for the humeral stem component are provided herein. Representative embodiments are shown, for example, in FIG. 52. Their use with other trial and prosthesis components and arthroplasty instruments are described herein below in connection with exemplary surgical techniques. The disclosed trial humeral head sizer instrument has a generally circular shape and domed profile with a cannulated and knurled handle for ease of positioning and placement of the K-wire/securement pin. The trial is used to establish appropriate head position, particularly in the instance where anatomically shaped elliptical (non spherical) humeral head prostheses are to be used. Markings on the trial are used to key the position of the head relative to the humeral bone. Of course it will be clear to one of ordinary skill that the trial heads may vary in material, color, and implements for marking and manipulation, and as such, the exemplary embodiment is merely representative.

Figure 55:
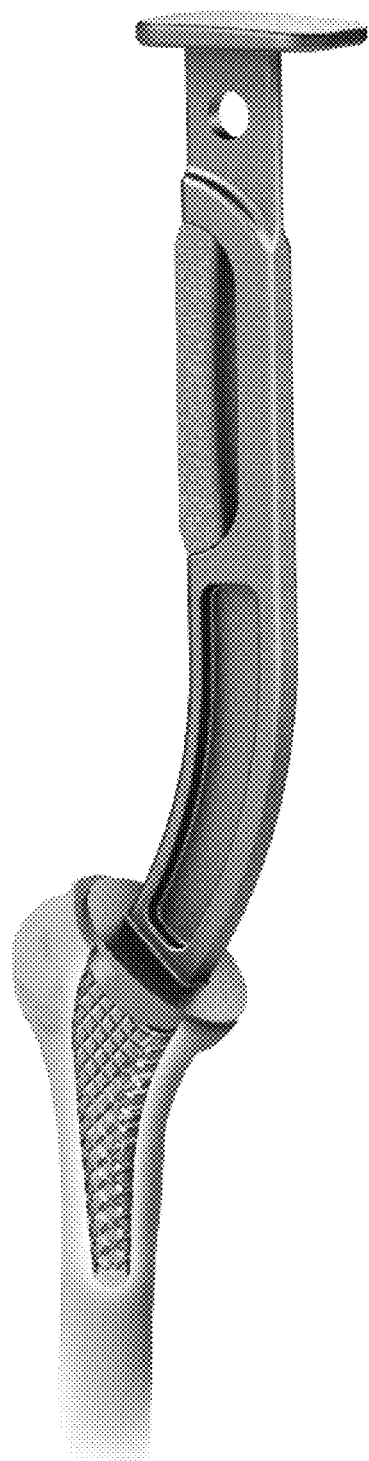
FIG. 55 is a graphic of a step in the sequence of a representative embodiment of a surgical technique for implanting an arthroplasty system in accordance with the disclosure showing a perspective view of a bone cut on a humerus with a stem broach.

The disclosed stem trial broach handle has a generally elongate profile with a proximal handle and engagement element that removably attaches to a stem trial or implant. The broach handle instrument also has a depth indicator or guide that enables precise alignment of the plane of the proximal surface of the stem relative to the plane of the bone cut. The depth guide also ensures that the stem is sunk within the bone at a depth that allows precise contact and engagement with the metaphyseal shell. As shown in FIG. 55, the exemplary stem broach handle has a depth guide that is generally plate like and positioned at the distal end of the handle, to interface with the bone cut and precisely orient the cut plane with the plane of the proximal end of the stem. Of course, it will be clear to one of ordinary skill that the broach handle instrument may vary in material, length, shape, and implements for guiding alignment with the bone cut, and as such, the exemplary embodiment is merely representative. In alternate embodiments, a guide element other than a planar disc may be positioned at the distal end to confirm alignment with the bone cut. Likewise, any of a variety of handle features and configurations known in art may be utilized to facilitate handling and positioning of the instrument relative to the stem and humerus.

Additional Shoulder Arthroplasty Components

Figure 32:
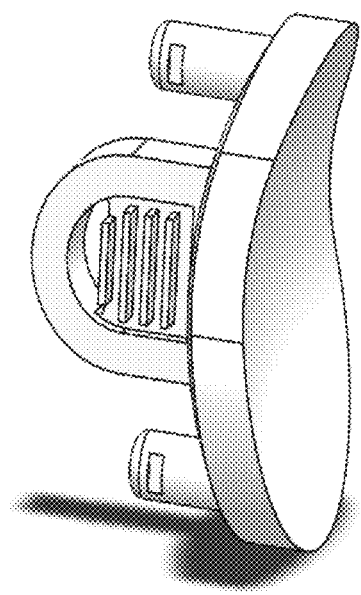
FIG. 32 shows a perspective view of an embodiment of a prosthesis articulation surface in the form of a glenoid, and a perspective view of an embodiment of a prosthesis articulation surface in the form of glenosphere.
Figure 32:
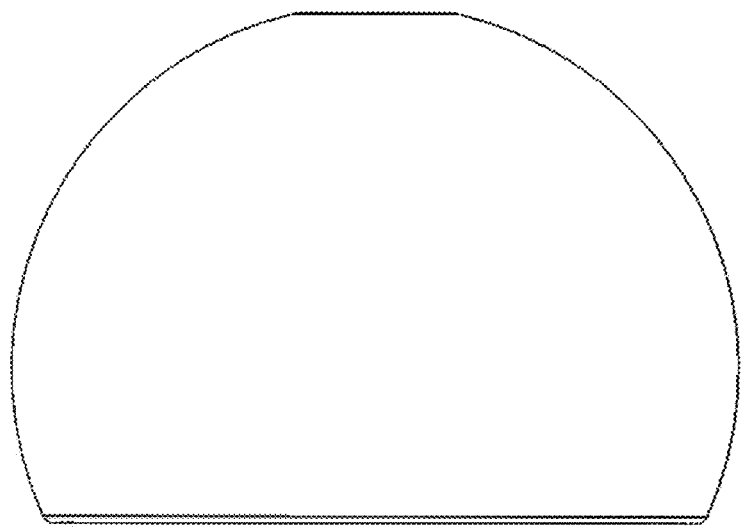
Figure 33:
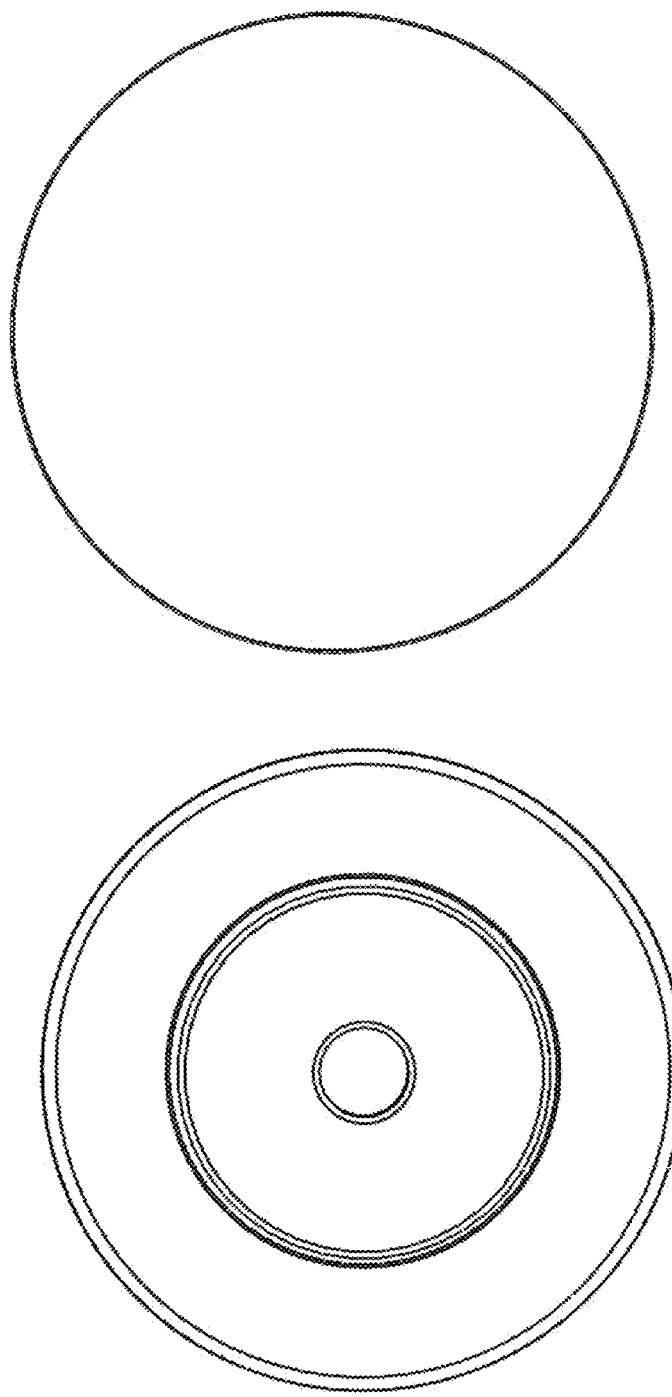
FIG. 33 shows a top view of an embodiment of a prosthesis articulation surface in the form of a spherical head, and a bottom view of an embodiment of a prosthesis articulation surface in the form of a spherical head.
Figure 34:
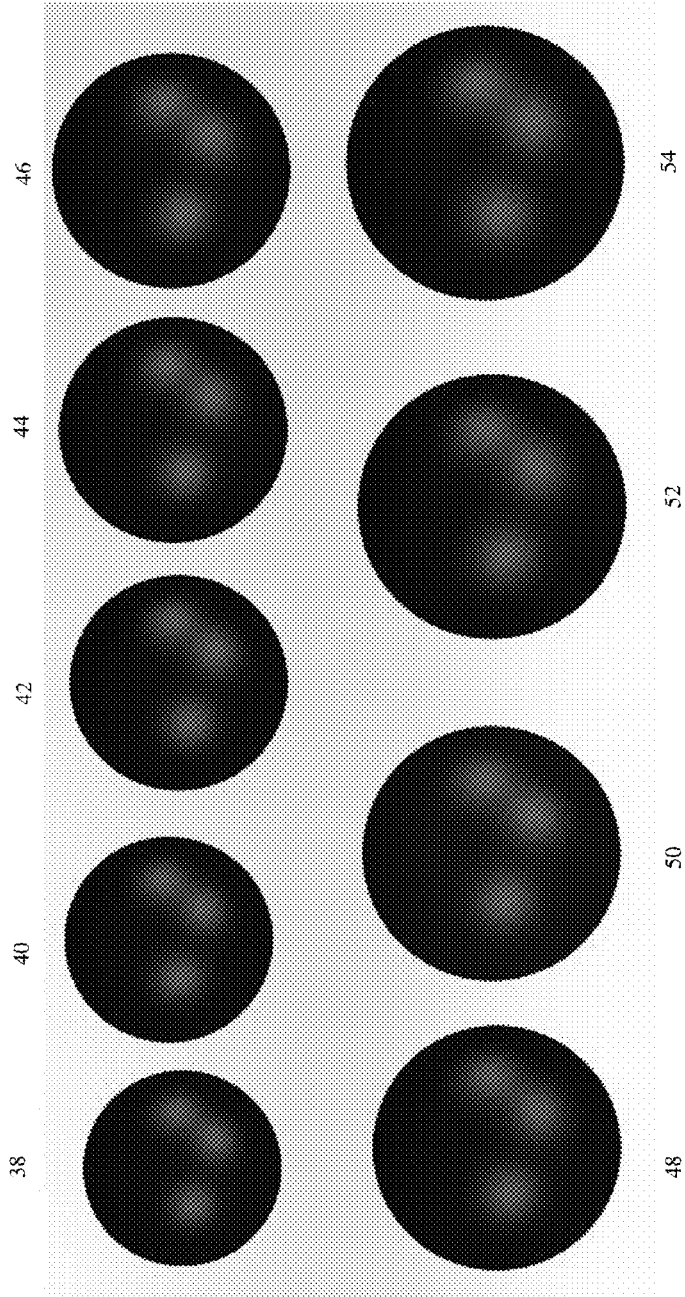
FIG. 34 is a top view of a size array of an embodiment of a prosthesis articulation surface in the form of a spherical head.

This disclosure also contemplates additional shoulder arthroplasty components that are suitable for engagement and articulation with the prostheses components of the modular arthroplasty assemblies disclosed herein. Accordingly, provided herein is an exemplary glenoid implant as depicted in FIG. 32, suitable for implantation and engagement with a humeral head prosthesis as described herein. In some embodiments, the glenoid implant is a new keel-type glenoid prosthesis that is improved over those in the art to enhance anchoring of the glenoid in the spongy part of bone, particularly during the immediate post implantation period, when mechanical engagement of the glenoid is most vulnerable. In various embodiments, the glenoid implant has two opposing surfaces. On one of its surfaces is an articulation surface adapted to cooperate with a humeral head. The opposing surface is adapted for engagement with the glenoid cavity, and includes a keel for anchoring it in the glenoid cavity of a shoulder. The keel extends from the glenoid cavity surface of the component and adapted to be immobilized in the glenoid cavity. The keel has two opposing faces, each of which face comprises at least one projecting fin that runs generally parallel to the glenoid surface and extends over at least a part of the perimeter of the keel. In alternate embodiments, the keel includes a plurality of fins aligned substantially in parallel with one another and to the surface of the glenoid and each extending over at least a part of the perimeter of the keel.

In some embodiments, the keel has fins that extend around the entire perimeter of the keel, covering both opposing faces. In alternate embodiments, the one or plurality of fins is located on one or both faces of the keel. In yet other embodiments, each face of the keel comprises a recess and the fins cover the surface of the recessed area but do not extend onto the remainder of the keel surfaces. In the various embodiments, the keel fins are flexible. It is the flexibility and arrangement of the fins on the keel faces that provide improved fixing of the glenoid in the glenoid cavity and ensure resistance of the glenoid to pull out from the cavity. The keel can be adapted for inclusion of bone growth promoters. In its various embodiments, the finned keel further provides a substrate to encourage boney growth over time to further secure the glenoid prosthesis in the glenoid cavity.

In various embodiments, the glenoid implant may incorporate one or more of the following features, in all technically permissible combinations: The body of the keel has in cross section a circular or a non-circular peripheral contour. The fin or at least one of the fins extends in a plane substantially perpendicular to a longitudinal main axis of the keel. The keel has a semicircular shaped cross section and an eccentric position relative to a central axis of the glenoid prosthesis. The fin or at least one of the fins has a substantially semicircular peripheral contour. The keel comprises a first series of substantially parallel fins. The fins are made of a deformable material chosen from materials such as polyethylene or other polymer materials. The keel may have any of varied dimensions and shapes. In some embodiments, the cross section has a non-circular peripheral contour, and for example may be generally frustohemispherical and frustoconical in shape with a substantially elliptical base, and in some embodiments may have a base which is elliptical or substantially square or rectangular. The glenoid implant may be augmented in a manner consistent with augmentation known in the art to compensate for bone loss and other defects in the surgical site.

Additional shoulder arthroplasty components include glenospheres adapted for engagement with the humeral implant system when a cupped prosthesis is engaged in the metaphyseal shell to provide a reverse shoulder configuration.

It will be appreciated that the individual components of the implant assembly may be made using a variety of materials, including metal and plastic and combinations of these. Such materials include but are not limited to: metals such as, for example, stainless steel, titanium alloys, cobalt alloys, cobalt chrome, superelastic metals, such as nitinol, polymers, such as polyester and polyethylene, polyether ether ketone (PEEK), carbon and carbon fiber materials. Porous coatings may be provided for any or a portion of the components, and specifically as described herein or as otherwise known in the art. The components may be provided with HA either dispersed on all or a portion of a surface, dispersed within all or a portion of the material of manufacture, and combinations of these.

To the extent used herein, the singular forms "a," "an," and "the" are intended to include the plural forms as well, unless the context clearly indicates otherwise. The term "proximal" to the extent used herein in connection with any object refers to the portion of the object that is closest to the operator of the object (or some other stated reference point), and to the extent used herein, the term "distal" refers to the portion of the object that is farthest from the operator of the object (or some other stated reference point). The terms "surgeon" and "operator" to the extent used herein are used interchangeably herein and each is intended to mean and refer to any professional or paraprofessional who delivers clinical care to a medical patient, particularly in connection with the delivery of care, including but not limited to a surgeon. Likewise, the terms "patient" and "subject" to the extent used herein are used interchangeably herein and each is intended to mean and refer to any clinical animal subject, including a human medical patient, particularly in connection with the delivery of care thereto by anyone, including a surgeon or operator to the extent those terms are used herein.

Spatially relative terms, such as "inner," "outer," "beneath", "below", "lower", "above", "upper" and the like, to the extent used herein, may be used herein for ease of description to describe one element or feature's relationship to another element(s) or feature(s) as illustrated in the drawings. Spatially relative terms may be intended to encompass different orientations of the device in use or operation in addition to the orientation depicted in the drawings. For example, if the device in the drawings is turned over, elements described as "below" or "beneath" other elements or features would then be oriented "above" the other elements or features. Thus, the example term "below" can encompass both an orientation of above and below. Thus, an item may be otherwise oriented (rotated 90 degrees or at other orientations) and the spatially relative descriptors used herein interpreted accordingly. With respect to any references to the extent used herein that may be made relative to an object, or to a body or subject for example that of a human patient, the terms "cephalad," "cranial" and "superior" indicate a direction toward the head, and the terms "caudad" and "inferior" and "distal" indicate a direction toward the feet. Likewise, the terms "dorsal" and "posterior" indicate a direction toward the back, and the terms "ventral" and "anterior" indicate a direction toward the front. And further, the term "lateral" indicates a direction toward a side of the body, the term "medial" indicates a direction toward the mid line of the body, and away from the side, the term "ipsalateral" indicates a direction toward a side that is proximal to the operator or the object being referenced, and the term "contralateral" indicates a direction toward a side that is distal to the operator or the object being referenced. More generally, any and all terms to the extent used herein providing spatial references to anatomical features shall have meaning that is customary in the art.

Unless otherwise indicated, all numbers expressing quantities, properties, and so forth as used in the specification, drawings and claims are to be understood as being modified in all instances by the term "about." Accordingly, unless otherwise indicated, the numerical properties set forth in the specification and claims are approximations that may vary depending on the suitable properties desired in embodiments of the disclosure. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

While the disclosed embodiments have been described and depicted in the drawings in the context of the human shoulder, it should be understood by one of ordinary skill that all or various aspects of the embodiments hereof may be used in connection with other species and within any species in any joint in the body.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts, or features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary, or representative values and ranges may be included to assist in understanding the present disclosure. However, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

I claim:

1. A modular system for long bone arthroplasty comprising:
    a generally disc shaped coupler component comprising:
        a prosthesis component side and an opposing anchor component side and a central axis;
        a lateral edge that bounds the prosthesis component and anchor component sides, the lateral edge comprising a surface treatment comprising texturing to encourage bony ingrowth or ongrowth;
        on the prosthesis component side, a recess having a substantially planar floor and a sidewall that is defined by the lateral edge and first and second prosthesis component engagement features, the first engagement feature comprising a tapered sidewall, and the second engagement feature comprising at least one circumferential tooth adjacent to a recess on the tapered sidewall;
        the anchor component side being substantially planar and comprising at least one anchor engagement feature comprising a male taper extending from a surface and radially offset from the central axis by from about 1 mm to about 8 mm; and
    an anchor component comprising a proximal portion having a planar proximal surface for contacting at least a portion of the planar surface of the anchor component side of the coupler component and a distal portion for positioning within a bone, the proximal portion comprising on its planar proximal surface a coupler component engagement feature and having an angle of inclination of from about 120 to about 145 degrees,
    wherein the generally disc shaped coupler component is configured to interchangeably engage both a convex prosthesis component and a concave prosthesis component.

2. The modular system for long bone arthroplasty according to claim 1, further comprising:
    a prosthesis component comprising on a first side a bone articulation surface that is either convex or concave and has a generally elliptical cross sectional shape, and comprising on an opposite second side an engagement feature for engagement with the coupler component.

3. The modular system for long bone arthroplasty according to claim 2, wherein the shape of the coupler component is selected from cylindrical, frustoconical, and frustohemispherical.

4. The modular system for long bone arthroplasty according to claim 3, wherein the coupler component is frustohemispherical.

5. The modular system for long bone arthroplasty according to claim 4, wherein the anchor component is a stem having an overall length, proximal portion length, distal portion length, proximal portion girth, and distal portion girth, and wherein the coupler component engagement feature comprises a female taper recessed into the planar proximal surface that is complementary to and configured for receiving the complementary male taper on the coupler component, and wherein at least a portion of the proximal portion of the stem comprises surface treatment to encourage bony ingrowth.

6. The modular system for long bone arthroplasty according to claim 5, further comprising at least a second anchor engagement feature on the coupler component that comprises a bore through the male taper for receiving a fastener adapted to engage with the anchor, wherein the female taper of the anchor component includes interior sidewalls and a base that comprises a bore adapted for concentric alignment with the bore in the coupler component, the bores adapted with fixation features for receiving a through fastener for releasable fixation of the coupler and anchor components, the system further comprising a fastener adapted for engagement within the bores of each of the coupler and anchor components and comprising a tool engagement feature for actuating fixation and release of the fastener.

7. The modular system for long bone arthroplasty according to claim 5, wherein the prosthesis component is selected from one of a convex head having an elliptical cross sectional shape that is not circular, and a concave cup having an elliptical cross sectional shape that is circular.

8. The modular system for long bone arthroplasty according to claim 7, wherein the prosthesis component comprises the convex head, and wherein the engagement features of the prosthesis and coupler components are concentrically aligned.

9. The modular system for long bone arthroplasty according to claim 8, wherein the convex head is a hemi-ellipse having a non-circular cross sectional shape that is defined by two perpendicular axes of symmetry and having an apex that has a non-circular elliptical cross sectional shape.

10. The modular system for long bone arthroplasty according to claim 9, wherein a ratio of the axes of symmetry of the convex head is at least 0.85.

11. The modular system for long bone arthroplasty according to claim 5, wherein the cross sectional shape of the anchor component at its proximal end is generally trapezoidal.

12. The modular system for long bone arthroplasty according to claim 1, wherein the at least one anchor engagement feature of the disc shaped coupler component is radially offset from the central axis at a distance selected from one of about 1 mm to about 6 mm, and from about 1 mm to about 3 mm.

13. The modular system for long bone arthroplasty according to claim 1, wherein the planar proximal surface of the anchor component has an angle of inclination from about 129 to about 139 degrees.

14. The modular system for long bone arthroplasty according to claim 1, wherein the planar proximal surface of the anchor component has an angle of inclination of about 135 degrees.

15. A modular system for long bone arthroplasty comprising:
  an array of prosthesis components, an array of anchor components and an array of coupler components, wherein a selected component of each of the arrays of prosthesis, anchor and coupler components are engageable to provide an arthroplasty assembly,
  wherein the position of the prosthesis component can be varied rotationally around a shared central engagement axis with the coupler component, and
  wherein the position of the anchor component relative to the coupler component can be varied in two dimensions on a plane that is perpendicular to the central engagement axis of the coupler and prosthesis components,
  wherein the coupler component is selected from an array consisting of a plurality of coupler components, each coupler component comprising a prosthesis component engagement side and an opposite anchor component engagement side, the sides bounded by a lateral edge that is one of cylindrical, frustoconical and frustohemispherical, and comprising a surface treatment comprising texturing to encourage bony ingrowth or ongrowth, wherein the coupler component is configured to interchangeably engage both a convex prosthesis component and a concave prosthesis component, wherein the array of coupler components has variably positioned anchor engagement features and each of at least two of the plurality of coupler components comprises at least one anchor engagement feature that is off-center from the central engagement axis of the coupler component,
  wherein the anchor component is selected from an array consisting of a plurality of anchor components each comprising a proximal portion having a proximal surface for contacting at least a portion of the coupler component and a distal portion for positioning within bone, the proximal portion having an angle of inclination of from about 120 to about 145 degrees and comprising a coupler component engagement feature, and wherein coupler component engagement feature includes a female taper recessed into the planar proximal surface that is complementary to and configured for receiving the complementary male taper on the coupler component,
  wherein the prosthesis component is selected from an array consisting of a plurality of prosthesis components each having a generally elliptical cross sectional shape and comprising on a first side a bone articulation surface that is either convex or concave, and comprising on an opposite second side an engagement feature for engagement with the coupler component, and,
  wherein, when one of each of the selected prosthesis, anchor and coupler components are engaged and the coupler and anchor components are recessed into bone, the assembly achieves alignment of the bone articulation surface of the prosthesis component with the bone that is anatomically similar to a native long bone.

16. The modular system for long bone arthroplasty according to claim 15, wherein the prosthesis component comprises a convex head that is a hemi-ellipse, and wherein the anchor engagement component of the coupler component is radially offset from the central axis by from about 1 mm to about 20 mm.

17. A modular system for long bone arthroplasty comprising:
  a generally disc shaped coupler component comprising:
    a prosthesis component side and an opposing anchor component side and a central axis;
    a lateral edge that bounds the prosthesis component and anchor component sides, the lateral edge comprising a surface treatment comprising texturing to encourage bony ingrowth or ongrowth;
    on the prosthesis component side, a recess having a substantially planar floor and a sidewall that is defined by the lateral edge and at least one prosthesis component engagement feature;
    the anchor component side being substantially planar and comprising at least one anchor engagement feature extending from a surface and radially offset from the central axis by from about 1 mm to about 8 mm, wherein the shape of the coupler component is selected from cylindrical, frustohemispherical, and frustoconical;
  a prosthesis component comprising on a first side a bone articulation surface is a convex head and has a generally elliptical cross sectional shape, wherein a ratio of the axes of symmetry of the convex head is from 0.85 to 1, and comprising on an opposite second side an engagement feature for engagement with the coupler component, wherein the at least one prosthesis component engagement feature is a tapered sidewall, and wherein the at least one anchor engagement feature is a male taper, and wherein the coupler component further comprises at least a second prosthesis component engagement feature that comprises at least one circumferential tooth on the tapered sidewall adjacent to a recess at the base, wherein the engagement features of the prosthesis and coupler components are concentrically aligned; and
  an anchor component comprising a proximal portion having a planar proximal surface for contacting at least a portion of the planar surface of the anchor component side of the coupler component and a distal portion for positioning within a bone, the proximal portion comprising on its planar proximal surface a coupler component engagement feature, wherein the anchor component is a stem having an overall length, proximal portion length, distal portion length, proximal portion girth, and distal portion girth, and wherein the coupler component engagement feature comprises a female taper recessed into the planar proximal surface that is complementary to and configured for receiving the complementary male taper on the coupler component, and wherein at least a portion of the proximal portion of the stem comprises surface treatment to encourage bony ingrowth, wherein the generally disc shaped coupler component is configured to interchangeably engage both a convex prosthesis component and a concave prosthesis component.

18. The modular system for long bone arthroplasty according to claim 17, wherein the planer proximal surface of the anchor component has an angle of inclination from about 129 to about 139 degrees.

* * * * *